(12) United States Patent
Varsavsky et al.

(10) Patent No.: US 9,943,256 B2
(45) Date of Patent: *Apr. 17, 2018

(54) METHODS AND SYSTEMS FOR IMPROVING THE RELIABILITY OF ORTHOGONALLY REDUNDANT SENSORS

(71) Applicant: MEDTRONIC MINIMED, INC., Northridge, CA (US)

(72) Inventors: Andrea Varsavsky, Santa Monica, CA (US); Xiaolong Li, Porter Ranch, CA (US); Mike C. Liu, Walnut, CA (US); Yuxiang Zhong, Pasadena, CA (US); Ning Yang, Los Angeles, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 337 days.

This patent is subject to a terminal disclaimer.

(21) Appl. No.: 14/260,948

(22) Filed: Apr. 24, 2014

(65) Prior Publication Data

US 2015/0164383 A1 Jun. 18, 2015

Related U.S. Application Data

(60) Provisional application No. 61/916,632, filed on Dec. 16, 2013.

(51) Int. Cl.
*A61B 5/00* (2006.01)
*A61B 5/1495* (2006.01)
(Continued)

(52) U.S. Cl.
CPC .......... *A61B 5/1495* (2013.01); *A61B 5/1455* (2013.01); *A61B 5/1459* (2013.01);
(Continued)

(58) Field of Classification Search
CPC . A61B 5/14532; A61B 5/1455; A61B 5/1495; A61B 5/1459; A61B 5/14546;
(Continued)

(56) References Cited

U.S. PATENT DOCUMENTS

| 4,755,173 A | 7/1988 | Konopka et al. |
| 5,391,250 A | 2/1995 | Cheney, II et al. |

(Continued)

FOREIGN PATENT DOCUMENTS

WO    WO 2013/184416 A2    12/2013

OTHER PUBLICATIONS

PCT International Search Report, International Application No. PCT/US2014/066794, dated Jun. 15, 2015, 8 pages.
(Continued)

*Primary Examiner* — Eric Winakur
*Assistant Examiner* — Chu Chuan (JJ) Liu
(74) *Attorney, Agent, or Firm* — Pillsbury Winthrop Shaw Pittman LLP

(57) ABSTRACT

Methods and systems for sensor calibration and sensor glucose (SG) fusion are used advantageously to improve the accuracy and reliability of orthogonally redundant glucose sensor devices, which may include optical and electrochemical glucose sensors. Calibration for both sensors may be achieved via fixed-offset and/or dynamic regression methodologies, depending, e.g., on sensor stability and Isig-Ratio pair correlation. For SG fusion, respective integrity checks may be performed for SG values from the optical and electrochemical sensors, and the SG values calibrated if the integrity checks are passed. Integrity checks may include checking for sensitivity loss, noise, and drift. If the integrity checks are failed, in-line sensor mapping between the electrochemical and optical sensors may be performed prior to calibration. The electrochemical and optical SG values may
(Continued)

be weighted (as a function of the respective sensor's overall reliability index (RI)) and the weighted SGs combined to obtain a single, fused SG value.

55 Claims, 63 Drawing Sheets

(51) Int. Cl.
*A61B 5/145* (2006.01)
*A61B 5/1459* (2006.01)
*A61B 5/1473* (2006.01)
*A61M 5/142* (2006.01)
*A61M 5/172* (2006.01)
*A61B 5/1455* (2006.01)
*A61B 5/1468* (2006.01)
*G01N 21/00* (2006.01)
*G01N 27/416* (2006.01)
*G01N 33/49* (2006.01)
*G01N 33/66* (2006.01)

(52) U.S. Cl.
CPC .......... *A61B 5/1468* (2013.01); *A61B 5/1473* (2013.01); *A61B 5/14532* (2013.01); *A61B 5/14556* (2013.01); *A61B 5/4839* (2013.01); *A61B 5/7221* (2013.01); *A61B 5/7278* (2013.01); *A61M 5/14244* (2013.01); *A61M 5/1723* (2013.01); *G01N 21/00* (2013.01); *G01N 27/4163* (2013.01); *G01N 33/49* (2013.01); *G01N 33/66* (2013.01); *A61B 2560/0223* (2013.01); *A61M 2005/1726* (2013.01); *A61M 2205/3306* (2013.01); *A61M 2205/3584* (2013.01); *A61M 2205/3592* (2013.01); *A61M 2205/50* (2013.01); *A61M 2205/505* (2013.01); *A61M 2205/52* (2013.01); *A61M 2230/201* (2013.01)

(58) Field of Classification Search
CPC . A61B 5/0002; A61B 5/0205; A61B 5/14551; A61B 5/14556; A61B 5/1473; A61B 5/4839; A61B 5/6849; A61B 5/72; A61B 5/7221
See application file for complete search history.

(56) References Cited

U.S. PATENT DOCUMENTS

| | | |
|---|---|---|
| 5,485,408 A | 1/1996 | Blomquist |
| 5,507,288 A | 4/1996 | Bocker et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 5,976,085 A * | 11/1999 | Kimball ............... A61B 5/1427 600/309 |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,424,847 B1 * | 7/2002 | Mastrototaro ..... A61B 5/14532 600/316 |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2004/0180391 A1 * | 9/2004 | Gratzl ............... A61B 5/14528 435/14 |
| 2007/0123819 A1 | 5/2007 | Mernoe et al. |
| 2008/0004536 A1 | 1/2008 | Baxi et al. |
| 2009/0030293 A1 | 1/2009 | Cooper et al. |
| 2009/0030334 A1 * | 1/2009 | Anderson ........... A61N 1/3702 600/528 |
| 2009/0033482 A1 | 2/2009 | Hayter et al. |
| 2009/0131773 A1 * | 5/2009 | Struve ............. G01N 33/54373 600/317 |
| 2009/0163855 A1 | 6/2009 | Shin et al. |
| 2010/0160861 A1 | 6/2010 | Causey, III et al. |
| 2011/0218489 A1 * | 9/2011 | Mastrototaro ..... A61B 5/14532 604/66 |
| 2011/0237917 A1 * | 9/2011 | Roy ................... A61B 5/14532 600/365 |
| 2011/0319734 A1 * | 12/2011 | Gottlieb ............ A61B 5/14503 600/347 |

(56) References Cited

U.S. PATENT DOCUMENTS

2012/0125075 A1* 5/2012 Gottlieb ............ A61B 5/14532
  73/1.02
2012/0262298 A1  10/2012 Bohm et al.
2013/0060105 A1   3/2013 Shah et al.

OTHER PUBLICATIONS

PCT Written Opinion of the International Searching Authority, International Application No. PCT/US2014/066794, dated Jun. 15, 2015, 15 pages.

* cited by examiner

4mm X 0.5mm

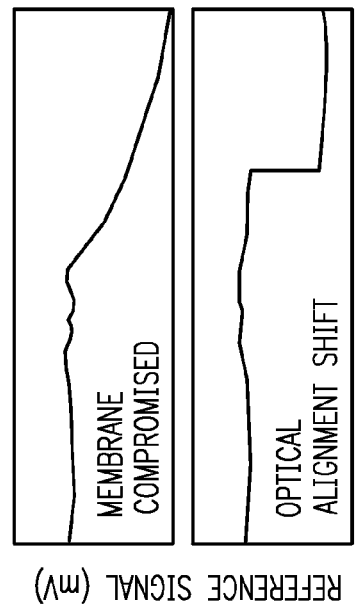
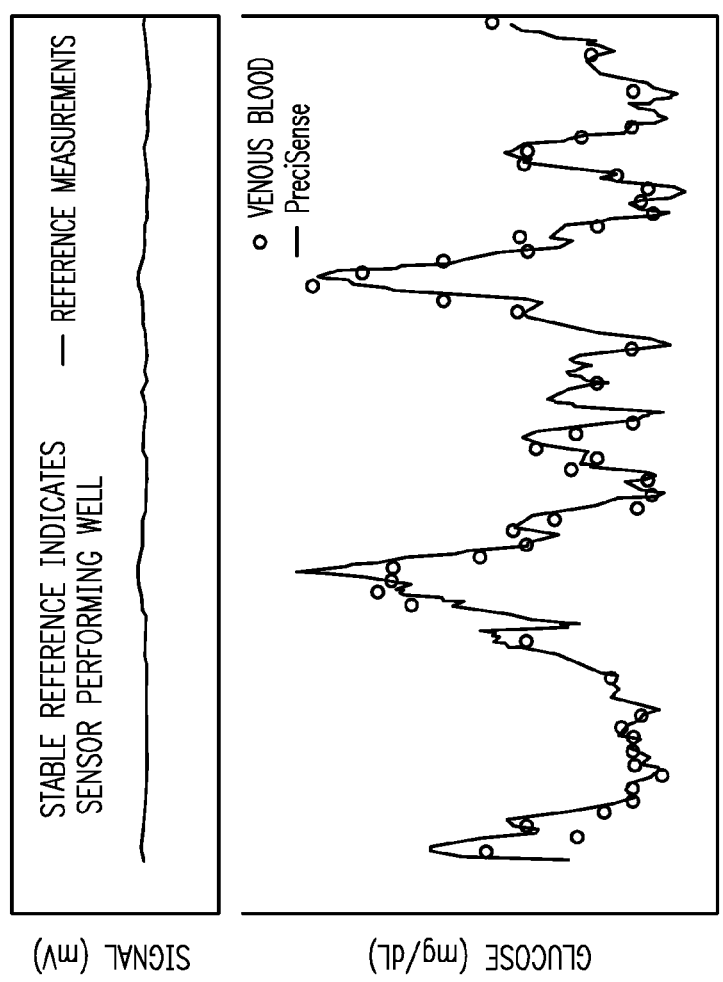
FIG. 6C
FIG. 6B

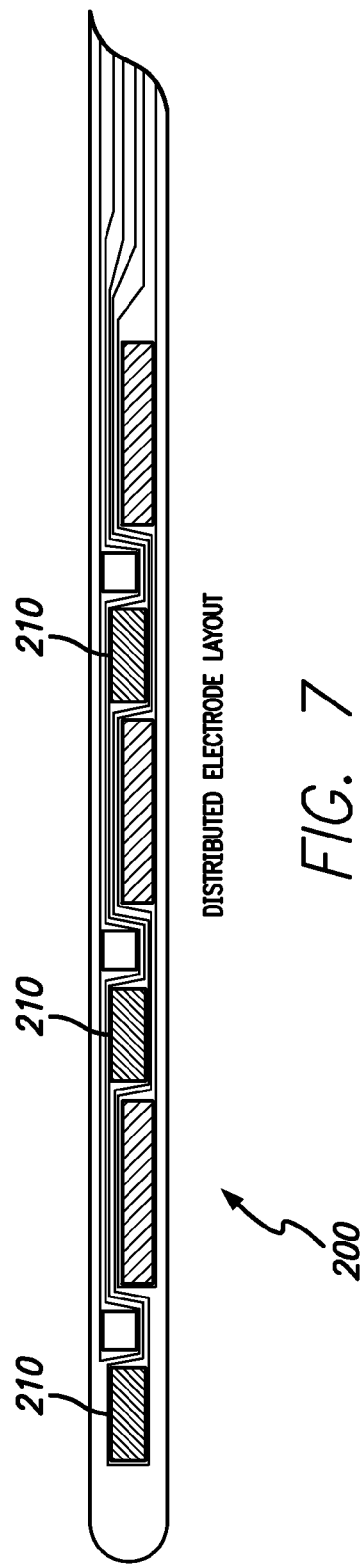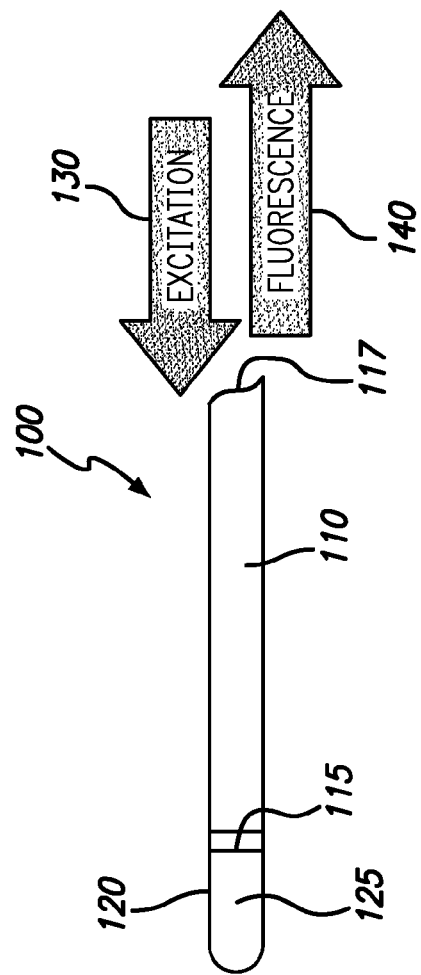

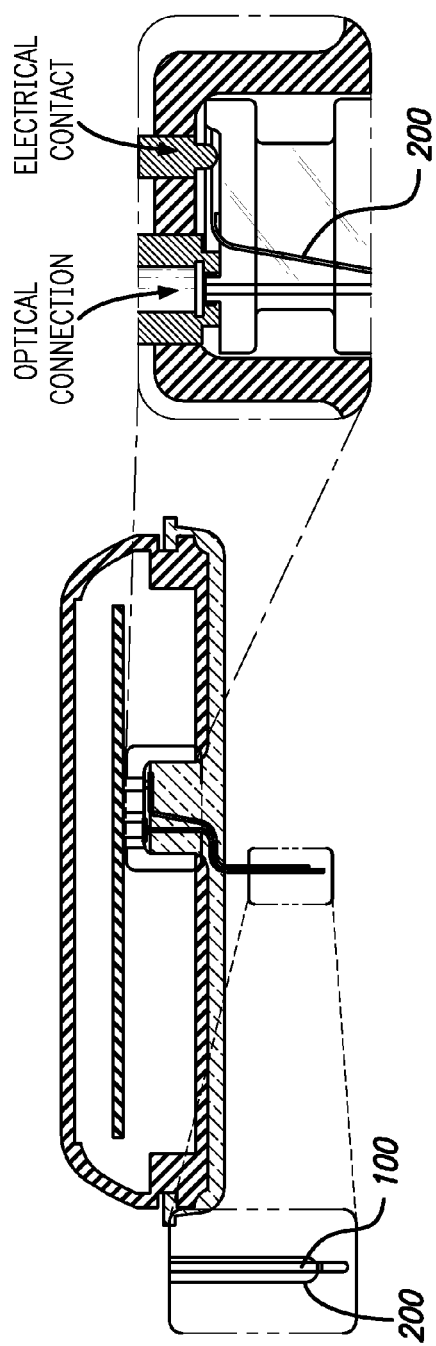
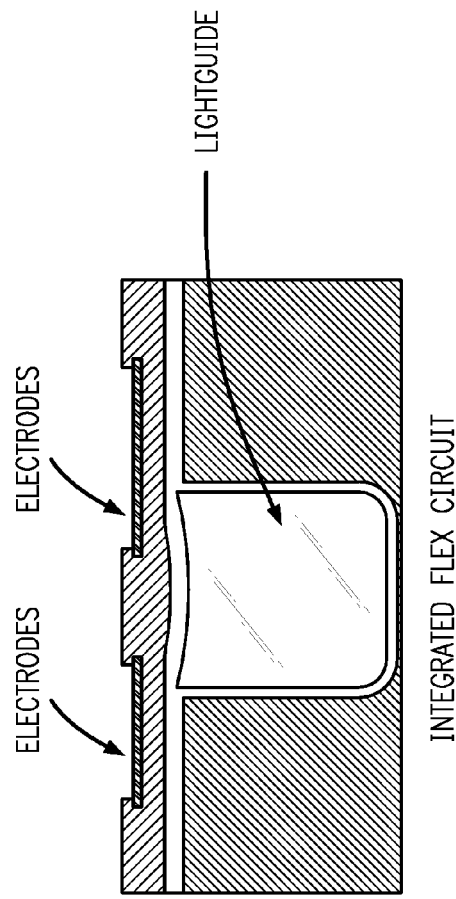
FIG. 9B
FIG. 9C

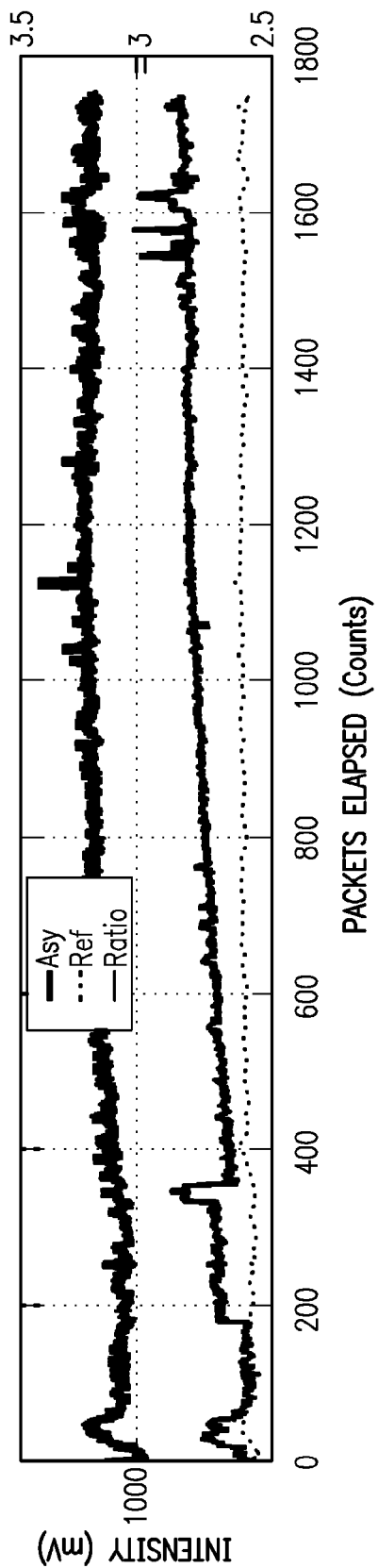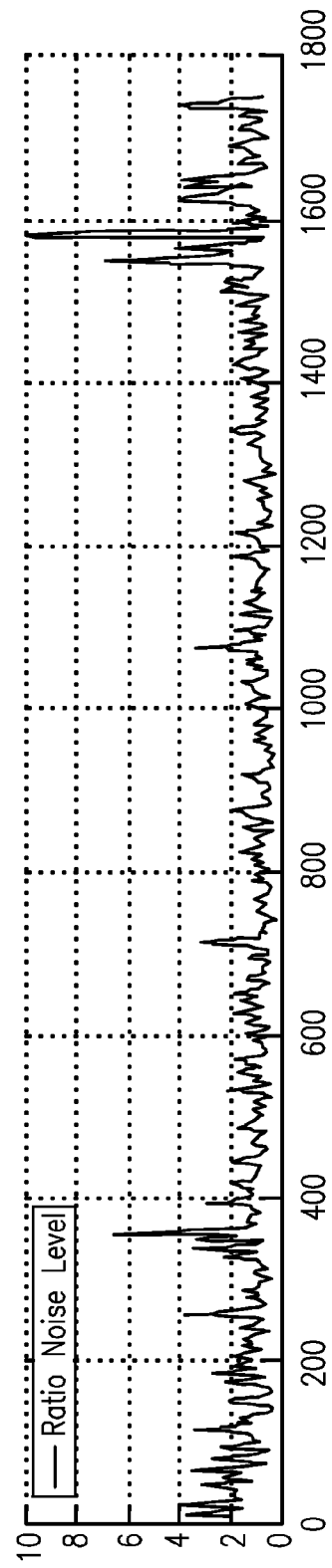
FIG. 23A
FIG. 23B

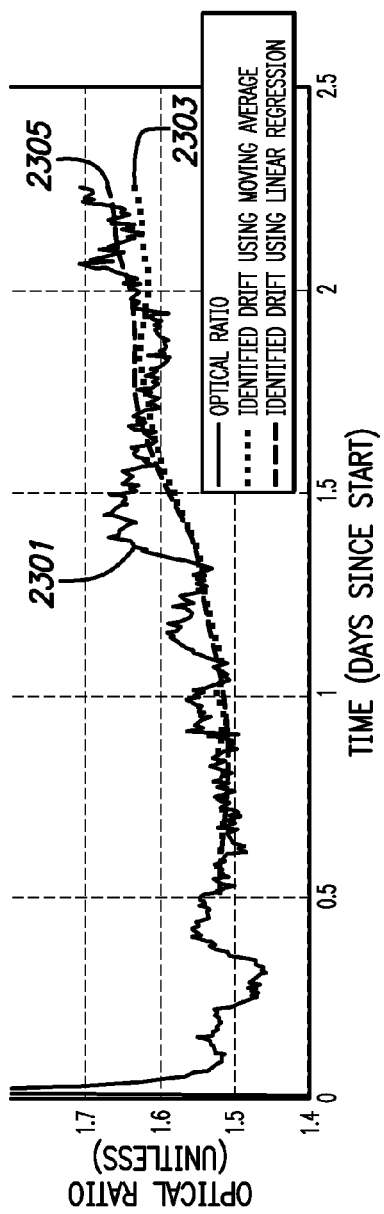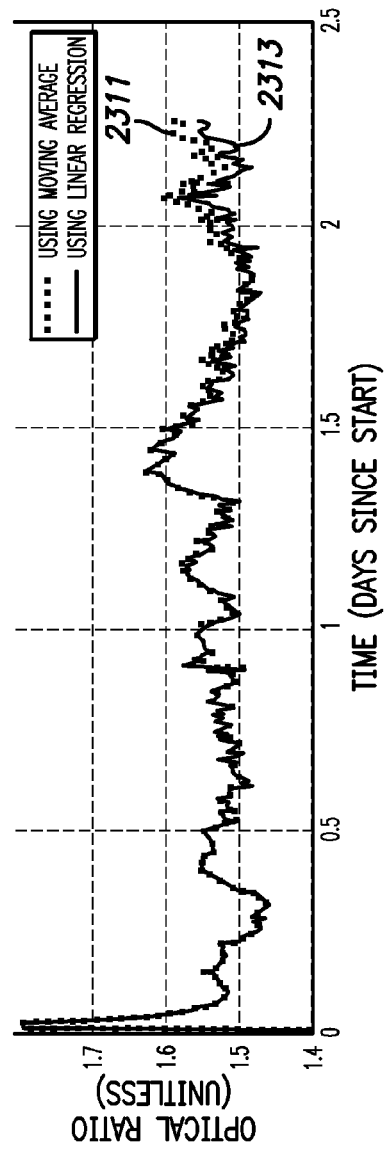
FIG. 24A
FIG. 24B

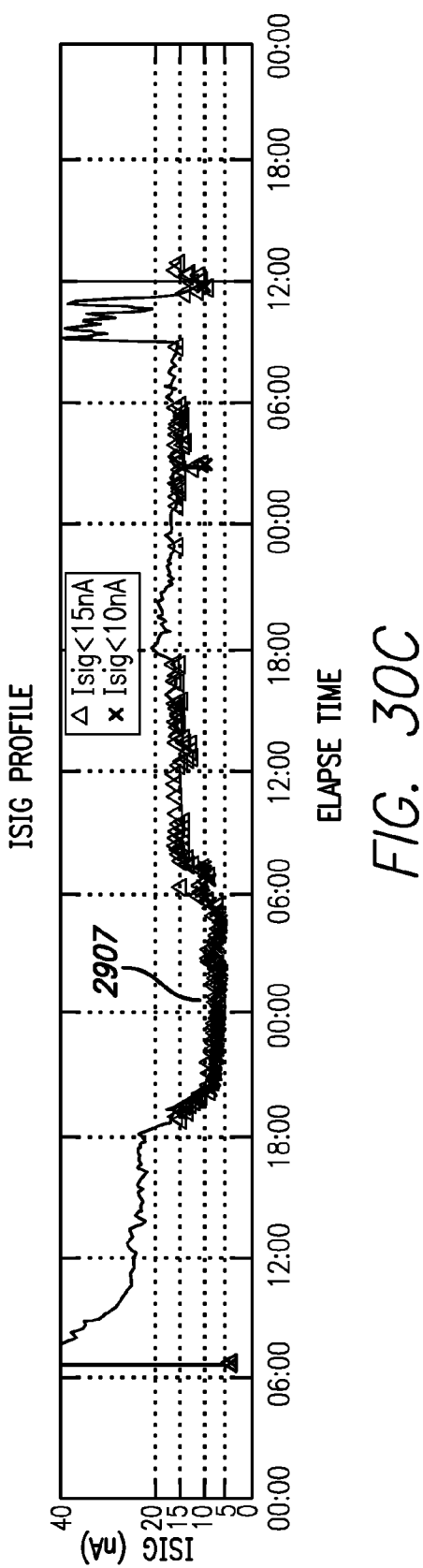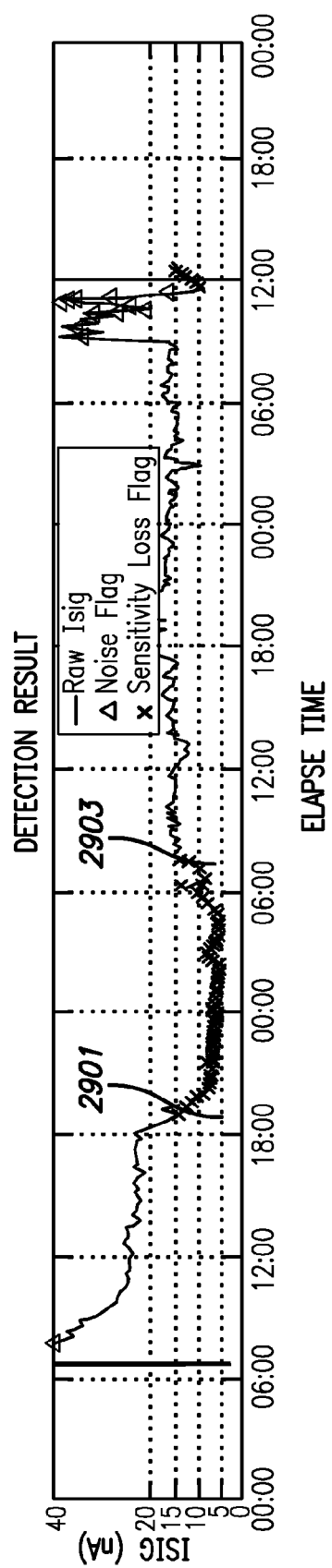
FIG. 30C
FIG. 30D

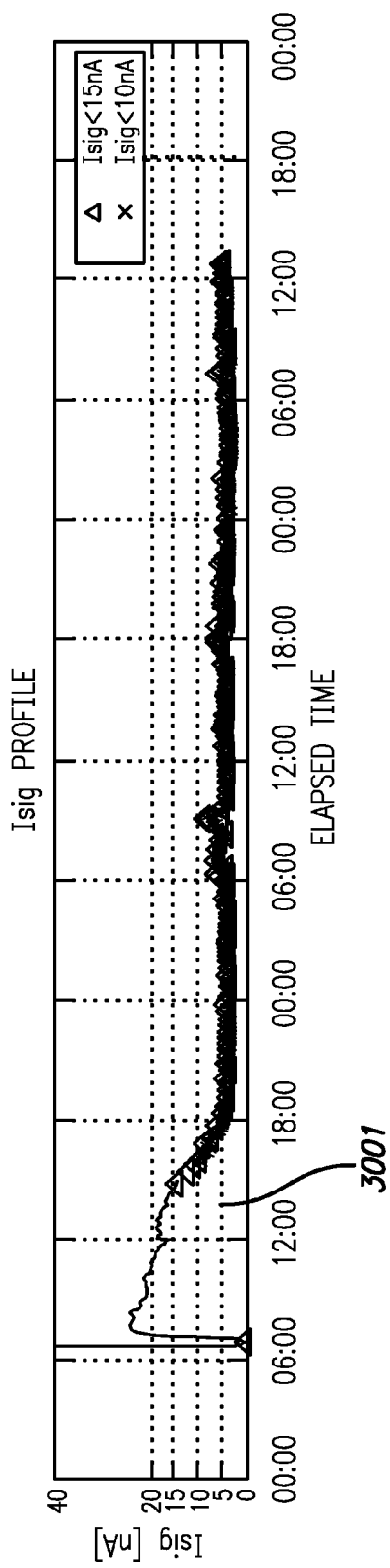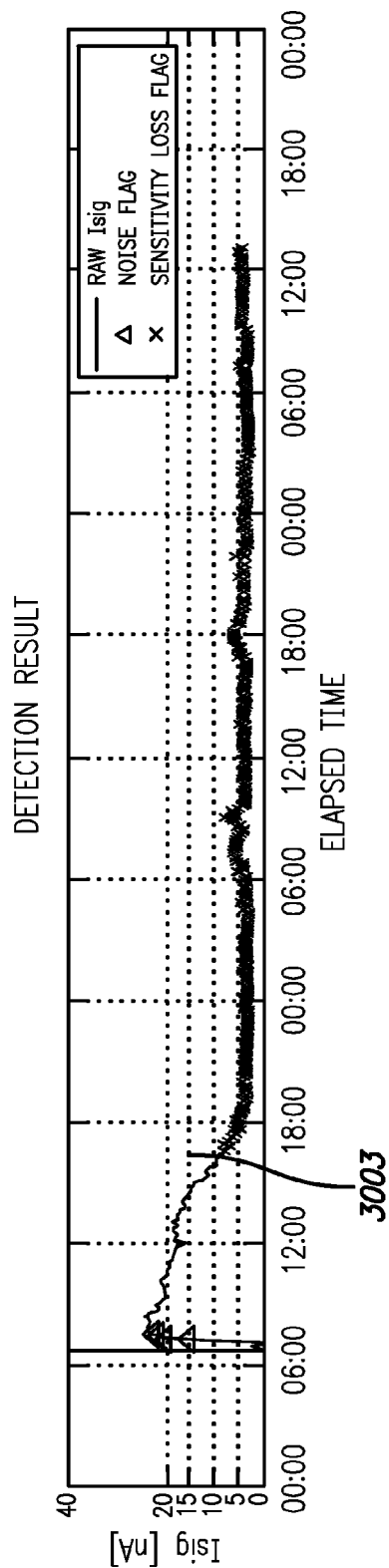
FIG. 31A
FIG. 31B

WEIGHTED LEAST SQUARE

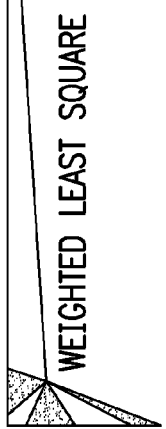

Instead of minimizing the residual sum of squares, $$RSS(\beta) = \sum_{i=1}^{n} (y_i - \vec{x_i} \cdot \beta)^2 \quad (1)$$

we could minimize the *weighted* sum of squares, $$WSS(\beta, \vec{w}) = \sum_{i=1}^{n} w_i (y_i - \vec{x_i} \cdot \beta)^2 \quad (2)$$

Weight coefficient: [.7 .2 .07 .03]

Conditions when WLS applies:
- BG range in cal buffer > 200 mg/dl
- Cal factor based upon GST3B algorithm is >=4 and >=6
- Offset based upon WLS method is >=-8 and <=-4

*FIG. 34*

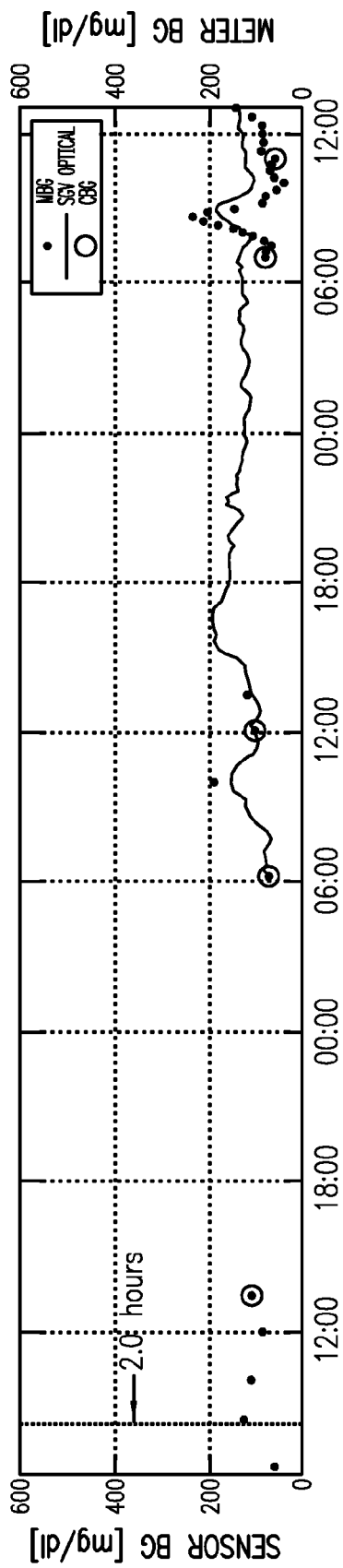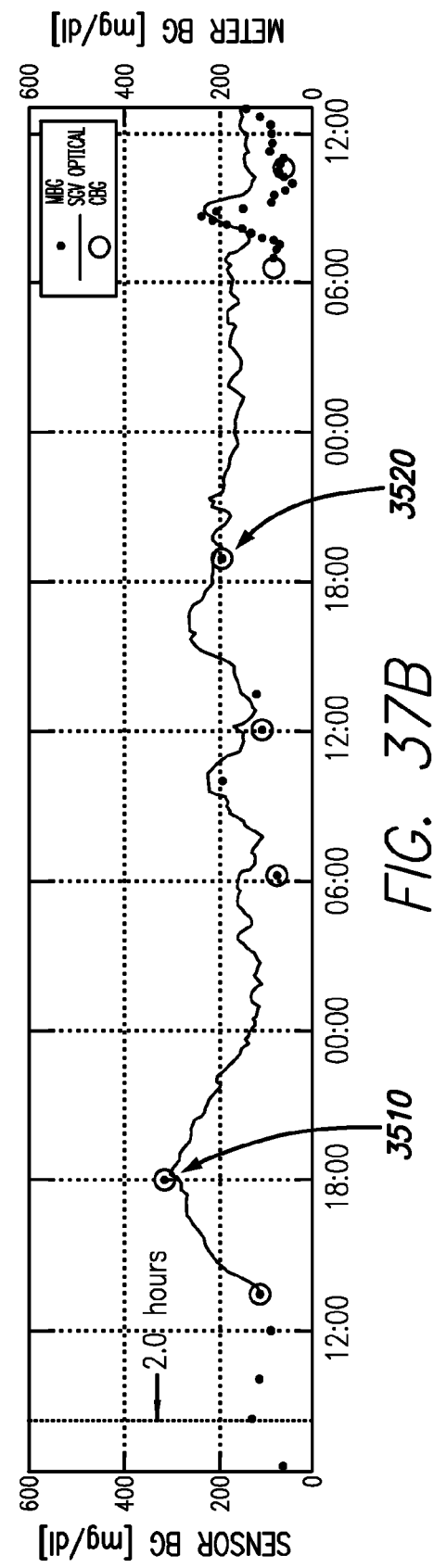
FIG. 37A
FIG. 37B

FIG. 46A

TABLE 1: Existing glucose sensor technologies, benefits, and drawbacks

| Sensing Technology | | Details | Benefits | Drawbacks |
|---|---|---|---|---|
| Electrochemical | Enzymatic | First generation | High glucose specificity and sensitivity | Interferences, high potential, added outer membranes effect response time |
| | | Second and third generation | High specificity, low overpotential prevents interferences | Toxic mediators, competition between mediators and oxygen, repeatability |
| | | Non-GO$_2$ based | No interferences from oxygen | Can oxidize other substances |
| | Nonenzymatic | | No enzyme degradation | Not specific to glucose |
| Optical | Fluorophore-based | Fluorescence or FRET intensity | Highly specific to glucose due to flurophore with glucose binding | Photobleaching, dependant on skin pigmentation and thickness |
| | | FRET lifetime | Independent of scattering and fluorophore concentration | Miniaturization of instrumentation difficult |
| | | Ocular spectroscopy | Noninvasive, uses tears to measure glucose visually | Leaching of chemicals, effected by pH and ionic strength, lag time |
| | | Optical coherence tomography | Not affected by urea, ionic strength, temperature, heart rate, and hematocrit | Affected by motion and tissue heterogeneity |
| | | Polarimetry | Can use visible light, can be miniaturized | Effected by scattering in the tissue, pH, and temperature, lack of specificity |

TO FIG. 46B →

FROM FIG. 46A 

| | | | |
|---|---|---|---|
| Nonfluorophore based | Thermal infrared spectroscopy | Can use visible light, can be miniaturized | Effected by scattering in the tissue, pH, probe position, fever, and temperature |
| | Photoacoustic spectroscopy | Not affected by ionic strength or albumins | Effected by scattering in the tissue, miniaturization difficult |
| | Raman spectroscopy | No interference from luminescence and fluorescence | Longer stabilization times, effected by tissue density, thickness, hematocrit |
| Combinatorial | Impedance spectroscopy | Can measure glucose levels in the vascular compartment, no lag time in sensor response | Temperature, disease state may affect measurements, changes in properties not specific to glucose |
| | Electromagnetic spectroscopy | Can measure glucose levels in the vascular compartment, no lag time in sensor response | Body temperature, sweating, and motion affect glucose measurements |

FIG. 46B

TABLE 2

| PERTURBATION | OPTICAL SENSOR RESPONSE | ELECTROCHEMICAL SENSOR RESPONSE |
|---|---|---|
| Endogen substances, i.e. ascorbate | No interference | Elevates glucose levels minimally |
| Exogenic substances, i.e. acetaminophen | Decreases glucose levels | Elevates glucose levels, reduced with membrane |
| Biofouling | No interference | Change in sensitivity |
| Temperature | Small change in baseline | Minimized by design |
| Oxygen | No interference | Minimized by design |

TABLE 3: Sources of sensor inaccuracy for both optical and electrochemical sensors, as well as benefit of simple and orthogonal redundancy on sensor performance. "NB" = No Benefit, "PB" = Potential Benefit, and "CB" = Clear Benefit.

| Sources of inaccuracy | Electrochemical sensor effect | Optical sensor effect | Benefit with simple electrochemical redundancy | Benefit with orthogonal redundancy | Benefit with orthogonal redundancy + predictive diagnostics | Orthogonally redundant sensor mitigation |
|---|---|---|---|---|---|---|
| Insufficient hydration | Low signal at Startup | High signal at startup | PB | CB | CB | Weighted average to estimate glucose |
| Connection issue | Loss of signal | Shift in reference signal | PB | CB | CB | Diagnose connection issue and advise patient |
| Partial pull-out signal, advise to | Decrease in signal | No effect to output | NB | CB | CB | Use optical sensor signal, advise to replace sensor |
| Low local glucose concentration* | Dip in signal | Dip in signal | NB | NB | PB | Predictive diagnostics on electrochemical sensor warn of local change |

TO FIG. 48B 

FROM FIG. 48A

| | | | | | |
|---|---|---|---|---|---|
| Low local oxygen concentration | Drift down in signal | No effect | NB | CB | CB | Weight optical sensor signal until re-calibration |
| Interference of electroactive species (i.e., acetaminophen) | Increase in signal | Slight decrease in signal | NB | CB | CB | Use magnitude of differing responses to diagnose acetaminophen |
| Interference of saccharides** | No effect | Increase in signal | CB | PB | PB | Request re-calibration based on differing signals |
| Biofouling | Decrease in signal | No effect | NB | CB | CB | Weight optical sensor signal until re-calibration |
| Compromised membrane | Decrease in signal | Reference signal gradually decreases | PB | CB | CB | Sensors will likely not experience compromised membranes at same time |

\* Failure mode of decreased glucose around sensor hypothesized to be due to attenuated perfusion to the sensor implant site.

\*\* Interference potential with maltose, used in certain hospital procedures such as peritoneal dialysis, is under evaluation to determine the extent to which this affects optical sensor response in the concentrations available in interstitial fluid.

FIG. 48B

TABLE 4

| SUB-SYSTEM | DESCRIPTION | ACCURACY DETERMINER |
|---|---|---|
| Transmitter | Powers device and samples sensor response. | Initializes the sensor with a modified pulse sequence to improve initial run-in time for the sensor to reach stability. |
| Algorithm | Software contained either within the transmitter or monitor. | Calibrates the sensor and performs fault detection diagnostics, reducing occurrence of erroneous data through additional meter points or data exclusion. |
| Monitor | Receives data from transmitter and communicates to patient. Link to the cloud. Houses a BG meter. | Performs error check to eliminate influence of bad meter points on accuracy and communicates reference factory cal values to aid transmitter diagnostics. |
| Sensor | Implanted unit and the base that adheres to patient skin. | Optimized electrode placement improves startup and removes local effects. |
| Chemistry | Enzyme and membrane deposited on top of the implanted sensor circuit. | Elimination of solvents and chemical reactions in processes improve accuracy. Thickness and layers optimized to improve Day 1, dynamic range and durability. |
| Accessories | Additional components, such as serter and overtape and patch adhesive. | Serter reduces trauma due to insertion. Overtape and patch adhesive prevent migration of the sensor that would reduce accuracy or result in early end of life. |

TABLE 5

| | Mannan Binding Lectin (MBL) | Glucose Galactose Binding Protein (GGBP) | Concanavalin A (Con A) | Antibodies (Ab's) | Boronic Acids |
|---|---|---|---|---|---|
| Description of the glucose receptor | Natural occurring human Lectin. All humans carry as a part of their innate immune system[1] | Periplasmic protein naturally occuring in e.g. E.Coli. Takes part in chemotaxis (cell movement) and metabolism | Chemical defense compound in Jack Bean. Helps to protect the bean from being eaten | Part of any higher organism's immune response. | Synthetic receptor with very simple structure, only two primary binding sites and little secondary stabilizing or selectivity creating binding. |
| Specificity and affinity | Natural selected for mannose and glucose binding in the clinical range (recognizes foreign glycosylation on intruder cells e.g. E.Coli) | Selective towards galactose and glucose. Wild type protein genetically modified to fit clinical range. | Selective towards mannose and glucose. Native and modified types fits the clinical range well | Ab's can be made to fit the clinical range by screening libraries. Ab variants created by small changes of the hyper variable regions in the Ab's[1] | Selectivity between stereoisomeric sugars (mannose and glucose) is difficult to obtain. |
| Stability | Natural selected for stability at 37C and human ion ($Ca^{2+}$=1.25mM) and metabolite (mM) concentrations | Naturally selected for body temperature[1] (E.coli is colon bacteria). Wild type optimized for low $Ca^{2+}$ (0.1 μM) and low metabolite (μM) concentration[2] | Poor at 37C[1] | Depends on the Ab, No generally information | |
| Regulatory | Phase 1[2] and Phase 2[3] clinical studies have been made using high MBL concentration and found no adverse effects. Should ease regulatory route | No literature found. Genetically modified non-human protein has no known regulatory route (but insulin is recombinant produced) | Known to cause agglutination of human cells[2] | Ab variants have been approved as drugs, but a specific AB is a new chemical entity and needs its own regulatory route[2] | New chemical entity needs testing |

TO FIG. 50B 

FROM FIG. 50A →

| | | | | |
|---|---|---|---|---|
| Sterility | Wet and dry e-beam[4] | Aseptic assembly[3] GGBP cannot be exposed to e-beam or γ-radiation (radical formation) | No information found | No information found | Aromatic boronic acid reacts with Reactive Oxygen Species (ROS) during sterilization and is eliminated and hence loses binding capability[1]. |
| Sourcing/ Production | Serum derived (hMBL)[5] or recombinant (rhMBL), Recombinant comes from mammalian cell lines to get the right glycosylation[6] | Recombinant from E.coli. A simple bacteria as E.coli cannot provide glycosylation | Extracted from Jack Bean | Expressed from E.Coli or mammalian cell lines | Chemically synthesized |
| Development time | Since 2003 | Since before 2002[4] | First publication 1982[3] | 2002 to 2005 with very limited success[3] | Since before 1998 |
| References | 1) Mol Immunol 40(2003)423<br>2) Scand J Immunol 2004 51(1) 97<br>3) Eur J Cancer 2009 45(4) 505<br>4) MDT Results<br>5) Vox Sang. 2007 92(4) 338–50<br>6) Biochem Soc. Trans. 2003 31(4):763–7 | 1) Biochem J. 2004 381(1) 97–103<br>2) J Biol Chem 262(1987)12570<br>3) Patent WO2007/022485<br>4) Biosens Bioelectron. 19(2004)653 (first manus 2002) | 1) PreciSense results<br>2) Nature 282(1979) 738<br>3) Diabetes Care. 5(1982)3245 | 1) Front Biosci. 13(2008)1117<br>2) Nat Biotechnol. 23(2005)1105<br>3) PreciSense attempts both immunizing mice and screening libraries | 1) US Pat US2011/0081727 |

FIG. 50B

TABLE 6: Individual accuracy effects on an orthogonally redundant system

| P(a) | P(b) | P(a OR b) |
|---|---|---|
| 70% | 70% | 91.00% |
| 70% | 75% | 92.50% |
| 75% | 75% | 93.75% |
| 75% | 80% | 95.00% |
| 80% | 80% | 96.00% |
| 90% | 90% | 99.00% |

FIG. 51

METHODS AND SYSTEMS FOR IMPROVING THE RELIABILITY OF ORTHOGONALLY REDUNDANT SENSORS

RELATED APPLICATION DATA

This application claim priority from U.S. Provisional Application Ser. No. 61/916,632, filed Dec. 16, 2013, which is incorporated herein by reference.

FIELD OF THE INVENTION

Embodiments of the present invention relate generally to sensor technology, including sensors used for sensing a variety of physiological parameters, e.g., glucose concentration. More particularly, embodiments of the invention relate to orthogonally redundant glucose sensors and sensor systems, including closed-loop insulin-infusion systems, and to calibration and sensor glucose (SG) fusion methods and systems for improving the accuracy and reliability of orthogonally redundant glucose sensors, devices, and systems.

BACKGROUND

The pancreas of a normal healthy person produces and releases insulin into the blood stream in response to elevated blood plasma glucose levels. Beta cells (β-cells), which reside in the pancreas, produce and secrete the insulin into the blood stream, as it is needed. If β-cells become incapacitated or die (Type I diabetes mellitus), or in some cases, if β-cells produce insufficient quantities of insulin (Type II diabetes), then insulin must be provided to the body from another source.

Traditionally, since insulin cannot be taken orally, insulin has been injected with a syringe. More recently, the use of infusion pump therapy has been increasing, especially for delivering insulin for diabetics. For example, external infusion pumps are worn on a belt, in a pocket, or the like, and deliver insulin into the body via an infusion tube with a percutaneous needle or a cannula placed in the subcutaneous tissue. Physicians have recognized that continuous infusion provides greater control of a diabetic's condition, and are increasingly prescribing it for patients.

Infusion pump devices and systems are relatively well-known in the medical arts for use in delivering or dispensing a prescribed medication, such as insulin, to a patient. In one form, such devices comprise a relatively compact pump housing adapted to receive a syringe or reservoir carrying a prescribed medication for administration to the patient through infusion tubing and an associated catheter or infusion set. Programmable controls can operate the infusion pump continuously or at periodic intervals to obtain a closely controlled and accurate delivery of the medication over an extended period of time. Such infusion pumps are used to administer insulin and other medications, with exemplary pump constructions being shown and described in U.S. Pat. Nos. 4,562,751; 4,678,408; 4,685,903; 5,080,653; and 5,097,122, which are incorporated by reference herein.

There is a baseline insulin need for each body which, in diabetic individuals, may generally be maintained by administration of a basal amount of insulin to the patient on a continual, or continuous, basis using infusion pumps. However, when additional glucose (i.e., beyond the basal level) appears in a diabetic individual's body, such as, for example, when the individual consumes a meal, the amount and timing of the insulin to be administered must be determined so as to adequately account for the additional glucose while, at the same time, avoiding infusion of too much insulin. Typically, a bolus amount of insulin is administered to compensate for meals (i.e., meal bolus). It is common for diabetics to determine the amount of insulin that they may need to cover an anticipated meal based on carbohydrate content of the meal.

Over the years, a variety of electrochemical glucose sensors have been developed for use in obtaining an indication of blood glucose levels in a diabetic patient. Such readings are useful in monitoring and/or adjusting a treatment regimen which typically includes the regular administration of insulin to the patient. Generally, small and flexible electrochemical sensors can be used to obtain periodic readings over an extended period of time. In one form, flexible subcutaneous sensors are constructed in accordance with thin film mask techniques. Typical thin film sensors are described in commonly assigned U.S. Pat. Nos. 5,390,671; 5,391,250; 5,482,473; and 5,586,553 which are incorporated by reference herein. See also U.S. Pat. No. 5,299,571.

These electrochemical sensors have been applied in a telemetered characteristic monitor system. As described, e.g., in commonly-assigned U.S. Pat. No. 6,809,653, the entire contents of which are incorporated herein by reference, the telemetered system includes a remotely located data receiving device, a sensor for producing signals indicative of a characteristic of a user, and a transmitter device for processing signals received from the sensor and for wirelessly transmitting the processed signals to the remotely located data receiving device. The data receiving device may be a characteristic monitor, a data receiver that provides data to another device, an RF programmer, a medication delivery device (such as an infusion pump), or the like.

Regardless of whether the data receiving device (e.g., a glucose monitor), the transmitter device, and the sensor (e.g., a glucose sensor) communicate wirelessly or via an electrical wire connection, a characteristic monitoring system of the type described above is of practical use only after it has been calibrated based on the unique characteristics of the individual user. Accordingly, the user is required to externally calibrate the sensor. More specifically, a diabetic patient is required to utilize a finger-stick blood glucose meter reading an average of two-four times per day for the duration that the characteristic monitor system is used. Each time, blood is drawn from the user's finger and analyzed by the blood glucose meter to provide a real-time blood sugar level for the user. The user then inputs this data into the glucose monitor as the user's current blood sugar level which is used to calibrate the glucose monitoring system.

Such external calibrations, however, are disadvantageous for various reasons. For example, blood glucose meters include inherent margins of error and only provide discrete readings at one point in time per use. Moreover, even if completely accurate, blood glucose meters are cumbersome to use (e.g., one should not operate an automobile and take a finger stick meter reading at the same time) and are also susceptible to improper use. Furthermore, there is a cost, not to mention pain and discomfort, associated with each application of the finger stick. Thus, finger stick replacement remains a goal for the next generation of glucose monitoring systems.

As sensor technology improves, there is greater desire to use the sensor values to control the infusion of insulin in a closed-loop system (i.e., an artificial pancreas system). Specifically, a closed-loop system for diabetes includes a glucose sensor and an insulin infusion pump attached to the patient, wherein the delivery of insulin is automatically administered by the controller of the infusion pump—rather than by the user/patient—based on the sensor's glucose value readings. The benefits of a closed-loop system are several-fold, including tighter glycemic control during the night when the majority of hypoglycemic events occur.

An accurate and reliable sensor has long been identified as a necessity for closed-loop realization. Glucose sensor technology has been evolving in an effort to meet the accuracy required for fingerstick replacement and the reliability needed for consistent closed-loop functionality. Several types of technology are available, with two of the most common and developed being electrochemical sensing, as noted above, and optical sensing. See FIGS. 46A and 46B.

To offer improved performance, the possibility of redundant electrodes has been explored and shown to provide a benefit. For example, previous studies in the literature have reported using two implanted glucose electrodes to simultaneously monitor glucose levels in rat tissue combined with a signal processing algorithm. These studies demonstrated that the overall glucose measurement accuracy could be improved over that of a single sensor. However, while it may provide for improved accuracy, such simple redundancy may not provide the reliability necessary for closed-loop applications.

Since the closed-loop system replaces the patient as the decision-making element, a reliable system must typically deliver reliable data and have error detecting functionality, enabling the closed-loop system to take action on erroneous data. Such data may be caused by drift, noise, or temporary or permanent malfunction of the sensor, often due to the implanted environment's effect on sensors. Actions may vary from simply prompting the patient to calibrate the system to terminating the sensor and requesting insertion of a new sensor. With identical sensor configurations, the redundant elements are similarly affected by environmental conditions and therefore could simultaneously present erroneous data.

Thus, although recent advances in continuous glucose monitoring (CGM) technology have offered several benefits for easier and more effective glycemic control in diabetes management, further improvements such as improved sensor accuracy and reliability, reduced number of blood glucose calibrations, improved specificity, and improved comfort during sensor insertion and wear are still desirable.

SUMMARY

According to an embodiment of the invention, a method of calibrating an orthogonally redundant sensor device for determining the concentration of glucose in the body of a user, where the sensor device includes at least an electrochemical glucose sensor and an optical glucose sensor, comprises receiving a first signal from the electrochemical glucose sensor; receiving a second signal from the optical glucose sensor; performing a respective integrity check on each of the first and second signals; determining whether the first signal can be calibrated, and whether the second signal can be calibrated, wherein the determination is made based on whether the first signal and the second signal pass or fail their respective integrity checks; if it is determined that the first signal can be calibrated, calibrating the first signal to generate an electrochemical sensor glucose (SG) value; if it is determined that the second signal can be calibrated, calibrating the second signal to generate an optical sensor glucose (SG) value; and fusing the electrochemical SG value and the optical SG value to obtain a single, fused sensor glucose value for the orthogonally redundant sensor device.

In a related aspect, a continuous glucose monitoring system is disclosed that comprises an orthogonally redundant glucose sensor device having an optical glucose sensor and an electrochemical glucose sensor; and a transmitter operatively coupled to the electrochemical and optical glucose sensors and having a housing, wherein the transmitter includes sensor electronics in said housing, including at least one physical microprocessor that is configured to receive a first signal from the electrochemical glucose sensor and a second signal from the optical glucose sensor; perform a respective integrity check on each of the first and second signals; determine whether the first signal can be calibrated, and whether the second signal can be calibrated, wherein the determination is made based on whether the first signal and the second signal pass or fail their respective integrity checks; if it is determined that the first signal can be calibrated, calibrate the first signal to generate an electrochemical sensor glucose (SG) value; if it is determined that the second signal can be calibrated, calibrate the second signal to generate an optical sensor glucose (SG) value; and fuse the electrochemical SG value and the optical SG value to calculate a single, fused sensor glucose value for the orthogonally redundant glucose sensor device.

In a further related aspect, a program code storage device comprises a computer-readable medium and non-transitory computer-readable program code, stored on the computer-readable medium, the computer-readable program code having instructions, which when executed cause a microprocessor to receive a first signal from an electrochemical glucose sensor and a second signal from an optical glucose sensor of an orthogonally redundant glucose sensor device for determining the concentration of glucose in the body of a user; perform a respective integrity check on each of the first and second signals; determine whether the first signal can be calibrated, and whether the second signal can be calibrated, wherein the determination is made based on whether the first signal and the second signal pass or fail their respective integrity checks; if it is determined that the first signal can be calibrated, calibrate the first signal to generate an electrochemical sensor glucose (SG) value; if it is determined that the second signal can be calibrated, calibrate the second signal to generate an optical sensor glucose (SG) value; and fuse the electrochemical SG value and the optical SG value to calculate a single, fused sensor glucose value for the orthogonally redundant glucose sensor device.

In all of the above embodiments of the invention, if it is determined that the first signal has failed its integrity check, then it is determined whether the second signal passes its integrity check and, if the second signal passes its integrity check, the second signal is used to correct the first signal via in-line sensor mapping to generate a corrected first signal. The corrected first signal is then calibrated to generate the electrochemical SG value. Similarly, if it is determined that the second signal has failed its integrity check, then it is determined whether the first signal passes its integrity check and, if the first signal passes its integrity check, the first signal is used to correct the second signal via in-line sensor mapping to generate a corrected second signal. The corrected second signal is then calibrated to generate the optical SG value. The electrochemical SG value and the optical SG value are then fused to calculate a single, fused sensor glucose value for the orthogonally redundant glucose sensor device.

In accordance with another embodiment of the invention, a method is disclosed for calibrating an optical glucose sensor of an orthogonally redundant sensor device for determining the concentration of glucose in the body of a user, wherein the sensor device further includes an electrochemical glucose sensor, and the method comprises: receiving a first signal from the electrochemical glucose sensor and a second signal from the optical glucose sensor, wherein the second signal is obtained at a first point in time; receiving a meter glucose value, the meter glucose value being indicative of the user's blood glucose (BG) level and being obtained at a second point in time; pairing the meter glucose value with the second signal if the second point in time is within a specified amount of time before or after the first point in time; performing a validity check on the paired meter glucose value and second signal; if the meter glucose value is the first meter glucose value of one or more meter glucose values, then calculating a mapped value for the second signal based on the first signal; and calibrating the mapped value of the second signal based on the first meter glucose value.

In a related aspect, a continuous glucose monitoring system comprises an orthogonally redundant glucose sensor device having an optical glucose sensor and an electrochemical glucose sensor; and a transmitter operatively coupled to the electrochemical and optical glucose sensors and having a housing, wherein the transmitter includes sensor electronics in the housing including at least one physical microprocessor that is configured to: receive a first signal from the electrochemical glucose sensor and a second signal from the optical glucose sensor, wherein said second signal is obtained at a first point in time; receive a meter glucose value, the meter glucose value being indicative of the user's blood glucose (BG) level and being obtained at a second point in time; pair the meter glucose value with the second signal if said second point in time is within a specified amount of time before or after the first point in time; perform a validity check on the paired meter glucose value and second signal; if the meter glucose value is the first meter glucose value of one or more meter glucose values, then calculate a mapped value for the second signal based on the first signal; and calibrate the mapped value of the second signal based on the first meter glucose value.

In another related aspect, a program code storage device comprises a computer-readable medium and non-transitory computer-readable program code, stored on the computer-readable medium, the computer-readable program code having instructions, which when executed cause a microprocessor to receive a first signal from an electrochemical glucose sensor and a second signal from an optical glucose sensor of an orthogonally redundant glucose sensor device, wherein the second signal is obtained at a first point in time; receive a meter glucose value, the meter glucose value being indicative of a user's blood glucose (BG) level and being obtained at a second point in time; pair the meter glucose value with the second signal if the second point in time is within a specified amount of time before or after the first point in time; perform a validity check on the paired meter glucose value and second signal; if the meter glucose value is the first meter glucose value of one or more meter glucose values, then calculate a mapped value for the second signal based on the first signal; and calibrate the mapped value of the second signal based on the first meter glucose value.

According to another embodiment of the invention, a method of calculating a single, fused sensor glucose (SG) value based on respective output signals of an electrochemical glucose sensor and an optical glucose sensor of an orthogonally redundant glucose sensor device comprises performing a status check on each of the electrochemical glucose sensor and the optical glucose sensor; calculating a first reliability index for the output signal of the electrochemical sensor; calculating a second reliability index for the output signal of the optical sensor; calibrating the output signal of the electrochemical sensor to obtain an electrochemical sensor glucose value (echem SG); calibrating the output signal of the optical sensor to obtain an optical sensor glucose value (optical SG); calculating a first weight based on the first reliability index and calculating a weighted echem SG based on the first weight; calculating a second weight based on the second reliability index and calculating a weighted optical SG based on the second weight; and calculating the single, fused sensor glucose value based on the weighted echem SG and the weighted optical SG.

In a related aspect, a continuous glucose monitoring system is disclosed that comprises an orthogonally redundant glucose sensor device comprising an optical glucose sensor and an electrochemical glucose sensor; and a transmitter operatively coupled to the electrochemical and optical glucose sensors and having a housing, wherein the transmitter includes sensor electronics in the housing, including at least one physical microprocessor that is configured to perform a status check on each of the electrochemical glucose sensor and the optical glucose sensor; calculate a first reliability index for an output signal of the electrochemical sensor; calculate a second reliability index for an output signal of the optical sensor; calibrate the output signal of the electrochemical sensor to obtain an electrochemical sensor glucose value (echem SG); calibrate the output signal of the optical sensor to obtain an optical sensor glucose value (optical SG); calculate a first weight based on the first reliability index and generate a weighted echem SG based on the first weight; calculate a second weight based on the second reliability index and generate a weighted optical SG based on the second weight; and calculate a single, fused sensor glucose value for the orthogonally redundant glucose sensor device based on the weighted echem SG and weighted optical SG.

In another related aspect, a program code storage device comprises a computer-readable medium and non-transitory computer-readable program code, stored on the computer-readable medium, the computer-readable program code having instructions, which when executed cause a microprocessor to perform a status check on each of an electrochemical glucose sensor and an optical glucose sensor of an orthogonally redundant glucose sensor device; calculate a first reliability index for an output signal of the electrochemical sensor; calculate a second reliability index for an output signal of the optical sensor; calibrate the output signal of the electrochemical sensor to obtain an electrochemical sensor glucose value (echem SG); calibrate the output signal of the optical sensor to obtain an optical sensor glucose value (optical SG); calculate a first weight based on the first reliability index and generate a weighted echem SG based on the first weight; calculate a second weight based on the second reliability index and generate a weighted optical SG based on the second weight; and calculate a single, fused sensor glucose value for the orthogonally redundant glucose sensor device based on the weighted echem SG and weighted optical SG.

In accordance with yet another embodiment of the invention, a method of correcting for a drift component of an output signal of a sensor comprises measuring the output signal of the sensor over time to obtain a plurality of output signal measurements as a function of time, wherein each of the output signal measurements comprises a true output signal component and said drift component as a function of time; calculating, as a function of time, an estimate of the drift component of the plurality of output signal measurements; and calculating an estimate of the true output signal component as a function of time based on the estimate of the drift component.

In a related aspect, a program code storage device comprises a computer-readable medium and non-transitory computer-readable program code, stored on the computer-readable medium, the computer-readable program code having instructions, which when executed cause a microprocessor to measure an output signal of a sensor over time to obtain a plurality of output signal measurements as a function of time, wherein each of the output signal measurements comprises a true output signal component and a drift component as a function of time; calculate, as a function of time, an estimate of the drift component of the plurality of output signal measurements; and calculate an estimate of the true output signal component as a function of time based on the estimate of the drift component.

In aspects of the invention, the drift component may be estimated, and corrected for, via mathematical modeling using either a moving-average approach or regression. In addition, the sensor may be a glucose sensor, such as, e.g., an optical sensor, where the measured output signal is the optical ratio of the optical sensor. The optical sensor may be part of an orthogonally redundant sensor device which, in turn, may also include an electrochemical sensor.

The above features and aspects may also be operationalized in closed-loop systems, with predictive diagnostics and minimal requirements for external calibration.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

FIGS. 6B and 6C show, in accordance with an embodiment of the invention, the use of a reference fluorophore, as a diagnostic tool for an optical sensor, indicating when, e.g., the integrity of the membrane may have been compromised or the optical connection may have been misaligned.

FIG. 7 shows a plurality of sensor electrodes distributed along the length of an electrochemical sensor in accordance with an embodiment of the invention.

FIG. 8A shows, in accordance with an embodiment of the invention, a side view of an optical fiber sensor containing an assay within a membrane coupled to the fiber's distal end, with excitation light entering, and fluorescence leaving, the fiber.

FIG. 9B is a sectional view of a transmitter, with an optical connection, an electrical contact, and co-located deployment of an electrochemical sensor and an optical sensor in accordance with embodiments of the invention.

FIG. 9C shows a sectional view of an integrated flex circuit in accordance with embodiments of the invention.

FIG. 23A shows illustrative plots of data for the optical assay, reference, and Ratio.

FIG. 23B shows a noise level evaluation curve derived based on the data points of FIG. 23A, in accordance with embodiments of the invention.

FIG. 24A shows the raw optical ratio signal measured in a diabetic dog prior to drift correction, as well as the estimated drift, calculated in accordance with embodiments of the invention.

FIG. 24B shows the drift-corrected optical ratio signal obtained by using moving average and the drift-corrected optical ratio signal obtained by using linear regression in accordance with embodiments of the invention.

FIGS. 30A-30D show failure mode detection results for temporary sensitivity loss in accordance with embodiments of the invention.

FIGS. 31A and 31B show detection results for permanent sensitivity loss in accordance with embodiments of the invention.

FIG. 34 shows details of a dynamic regression calibration method in accordance with embodiments of the invention.

FIGS. 37A and 37B show an example of using electrochemical sensor glucose values as calibration glucose points to enable dynamic regression for the optical glucose sensor in accordance with embodiments of the invention.

FIGS. 46A and 46B show a table of existing glucose sensor technologies, benefits, and drawbacks.

FIG. 47 shows a table of responses to interferents and environmental perturbations by electrochemical and optical sensors.

FIGS. 48A and 48B show a table of sources of sensor inaccuracy for both optical and electrochemical sensors, as well as the benefit of simple and orthogonal redundancy on sensor performance.

FIG. 49 shows a table describing the role and contribution of each subsystem or component of a sensor system to sensor accuracy.

FIGS. 50A and 50B show a table describing the differences between Mannan Binding Lectin (MBL) and other glucose binders employed for equilibrium-based glucose sensors.

FIG. 51 shows a table of individual accuracy effect on an orthogonally redundant system, assuming true independence between the two sensing components.

DETAILED DESCRIPTION

Figure 1A:
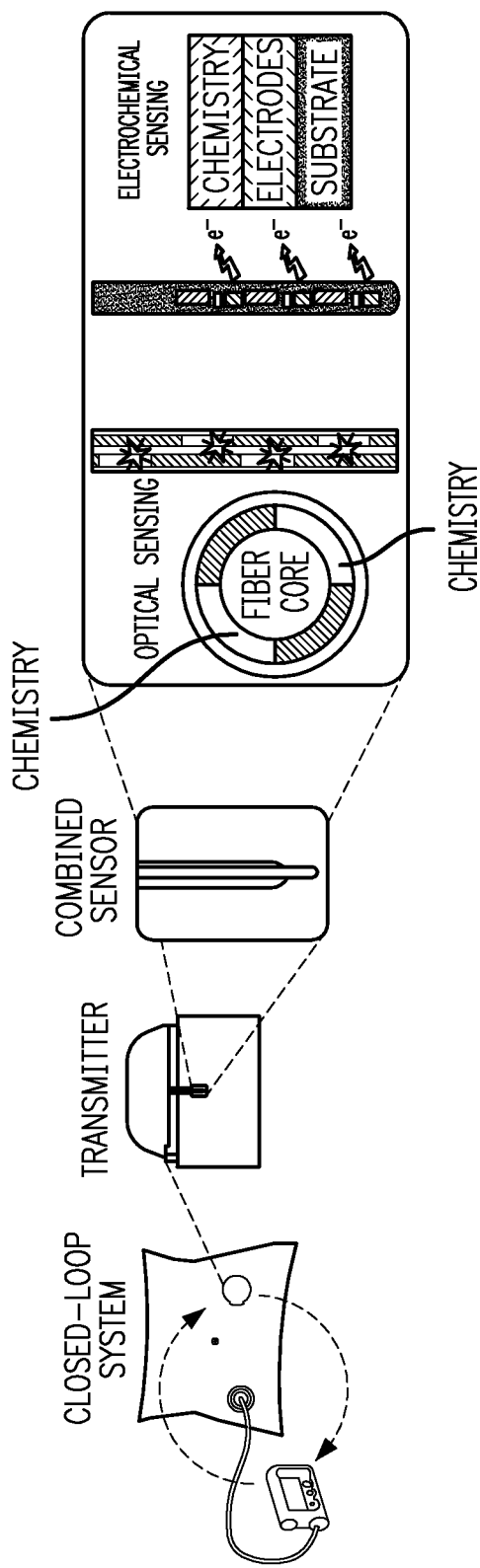
FIGS. 1A and 1B show continuous glucose monitoring systems for orthogonally redundant sensing in accordance with embodiments of the invention.

In the following description, reference is made to the accompanying drawings which form a part hereof and which illustrate several embodiments of the present invention. It is understood that other embodiments may be utilized and structural and operational changes may be made without departing from the scope of the present invention.

The inventions herein are described below with reference to flowchart illustrations of methods, systems, devices, apparatus, and programming and computer program products. It will be understood that each block of the flowchart illustrations, and combinations of blocks in the flowchart illustrations, can be implemented by programming instructions, including computer program instructions. These computer program instructions may be loaded onto a computer or other programmable data processing apparatus (such as a controller, microcontroller, or processor in a sensor electronics device) to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks. Programming instructions may also be stored in and/or implemented via electronic circuitry, including integrated circuits (ICs) and Application Specific Integrated Circuits (ASICs) used in conjunction with sensor devices, apparatuses, and systems.

As shown in the drawings for purposes of illustration, embodiments of the invention are directed to sensors that may be introduced and/or lodged transdermally, or may be implanted in and/or through subcutaneous, dermal, subdermal, inter-peritoneal, or peritoneal tissue. In the discussion herein, preferred embodiments of the devices, systems, and methods of the invention are described with reference to glucose as the analyte whose level/concentration in the blood and/or bodily fluids of the user is to be determined. However, this is by way of illustration and not limitation, as the principles, devices, systems, and methods of the present invention may be used for sensing and/or determining the level of a variety of other physiological parameters, agents, characteristics, and/or compositions.

In light of the above-noted needs in continuous glucose monitoring, embodiments of the invention are directed to a more robust solution in the form of an orthogonally redundant sensor (ORS) system. Orthogonal redundancy is defined as two devices employing two different technologies to reach the same goal, where the failure modes of the two devices are completely unique and do not intersect. This can be applied to continuous glucose sensing through the use of unique glucose detection schemes combined into a single body-worn device. The distinctive measurement technology, responses, and failure modes for each sensor provide true redundancy to ensure reliable and safe glucose measurements regardless of the environmental response or sensor anomalies.

In an embodiment of the invention, the above-mentioned orthogonal redundancy may be created by combining the technologies of optical sensing and electrochemical sensing to provide a unique solution to combat the complexities of the implanted environment. The two (i.e., optical and electrochemical) sensors are subject to different types of interferences, failure modes, and body responses, as described in FIG. 47. With this in mind, the reliability of each sensor can be calculated and weighted to provide the most robust and accurate glucose sensor measurement. Thus, as shown in FIG. 47, the unique and distinctive response to interferents and environmental perturbations by each of the sensors offers an enhanced ability to diagnose and filter environmental response.

With reference to FIG. 47, it has further been found that the interference profile of the optical sensor is very different from the interference profile for the electrochemical (also referred to as "echem") sensor. Thus, for all three of the primary electrochemical interfering substances—i.e., Acetaminophen, Uric Acid, and Ascorbic Acid—a single fluorophore optical sensor has either no interference or an interference signal that is in the opposite direction to that of the electrochemical sensor.

There are several sources of inaccuracies in glucose sensors. These inaccuracies may cause errors in sensor readings that can be corrected by a calibration, or they may be more serious errors from which the sensor cannot recover. The most common sources of error and the impact on the individual sensors are listed in FIGS. 48A and 48B.

It is known that acquiring signals from multiple electrochemical sensors can provide improved performance in the form of simple redundancy, accomplished through either multiple electrodes on the same probe, or by utilizing spatial separation and two separate probes. For example, Medtronic, Inc. sells hospital glucose sensors that include two probes, with two working electrodes on each probe, resulting in four independent glucose signals.

Systems utilizing multiple electrochemical sensors are also being developed by Medtronic, Inc. However, these systems still do not provide true redundancy through alternate sensing technologies with separate and distinct failure modes. As an example, studies have shown that, as the electrochemical sensor is pulled from the subcutaneous region into the dermal layers, the sensor signal goes to zero. In comparison, optical sensors perform well in both the dermis and the subcutaneous region, which allows the optical sensor to maintain functionality even as the sensor is partially explanted, providing the patient with a measurement until the patient is able to replace the sensor. Simple redundancy with electrochemical sensors would result in inaccurate data from both sensors in the event of partial explanation. See FIGS. 48A and 48B.

In short, in order to achieve the reliability required of continuous glucose monitoring systems, including closed loop, orthogonal redundancy is necessary. With orthogonally redundant sensing, the advantages of simple redundancy are maintained, with the additional benefit of having different susceptibilities and interferers between optical and electrochemical sensors. Thus, in certain embodiments, an orthogonally redundant sensor may include an optical sensor and an electrochemical sensor, wherein the latter may include up to, e.g., 5 independent sensing electrodes.

Figure 1B:
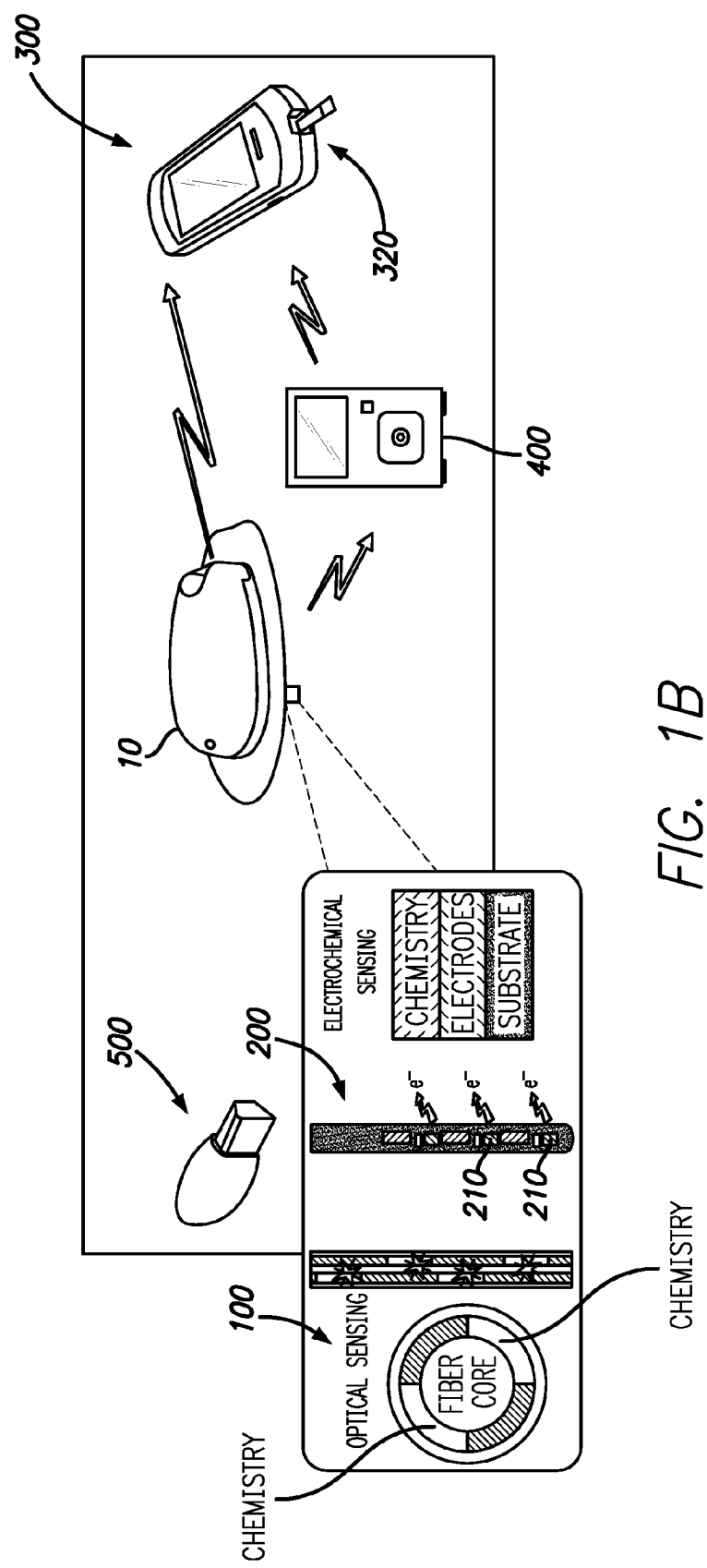

FIGS. 1A and 1B show components of a continuous glucose monitoring system for orthogonally redundant sensing in accordance with an embodiment of the invention. With reference to FIG. 49, in developing sensor systems, the role of the entire system on accuracy is considered, and a system-based approach to design is employed. Thus, as detailed in FIG. 49, each subsystem or component plays an integral role in contributing to the accuracy.

Figure 2:
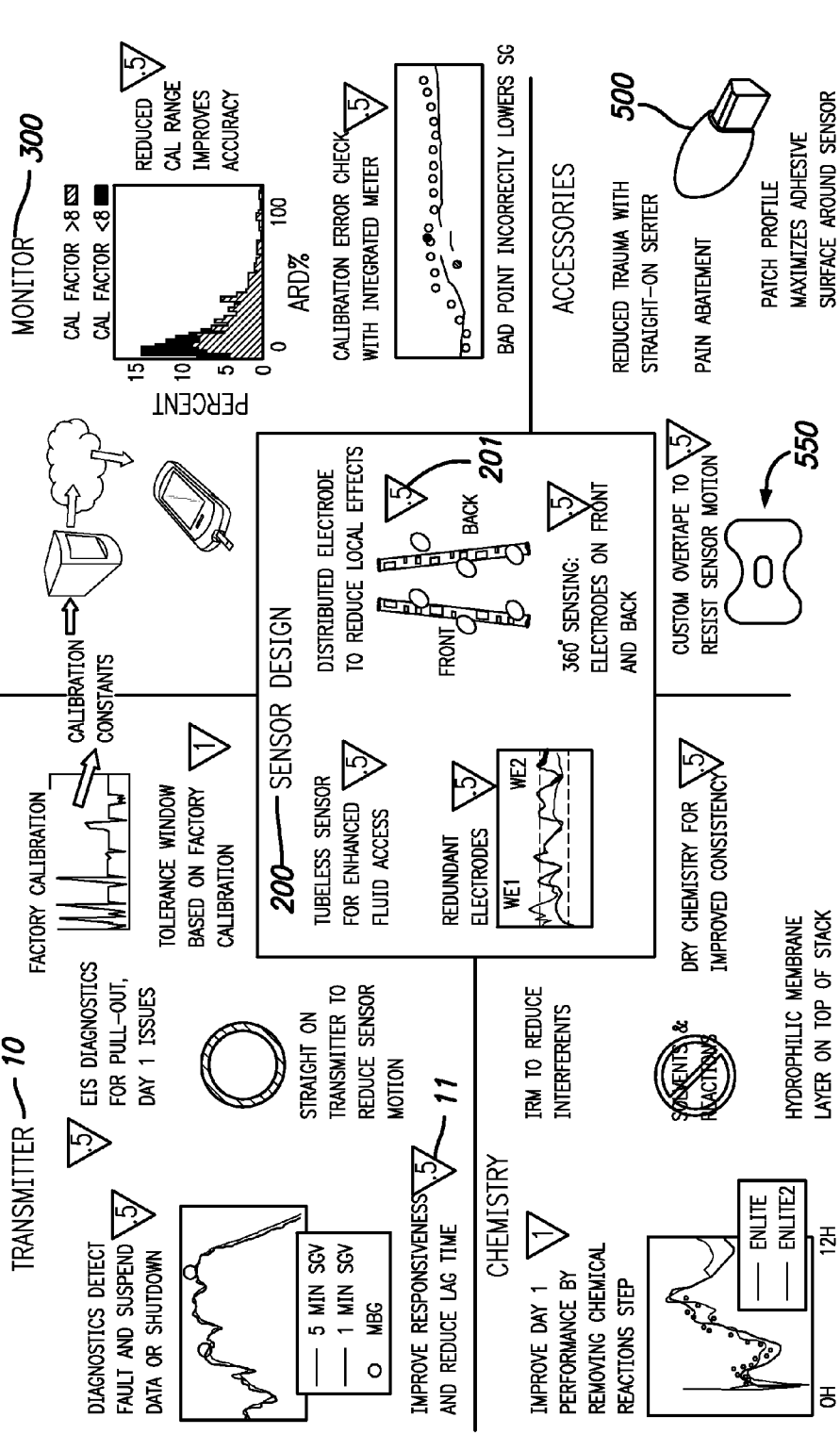
FIG. 2 shows a system-based approach to targeted electrochemical sensor improvements.

As will be described in more detail below, one goal of embodiments of the present invention is to continue to simultaneously improve both performance and usability. Thus, within each of the sub-systems described in FIG. 49, electrochemical sensor performance advancements have focused on reduction of variation through targeted improvements. These targeted improvements are designed to improve day 1 performance, durability, and hypo- and hyper-glycemic performance and are detailed in FIG. 2. Targeted improvements drive the electrochemical sensor to a predictable sensitivity across sensors, glucose ranges and over time. The sensor anomalies that remain as outliers can be reduced through predictive sensor diagnostics, which proactively detect faults or failures and recalibrate or shut down the sensor before it results in inaccurate glucose measurements.

It is understood that, for a given sensor or sensing system, the lower the Mean Absolute Relative Difference/Deviation (MARD) value, the higher the accuracy of the sensor or sensing system. As noted in FIG. 2, the system-based approach (to targeted sensor improvements) reduces the MARD value for an electrochemical sensor from about 16% to about 9%, and preferably less. For example, with respect to the transmitter 10, MARD is reduced by 0.5% by improving responsiveness and reducing lag time (reference numeral 11). Similarly, with regard to the design of the electrochemical sensor 200, MARD is reduced by an additional 0.5% by effecting a distributed-electrode design in order to reduce local effects (reference numeral 201).

Figure 3A:
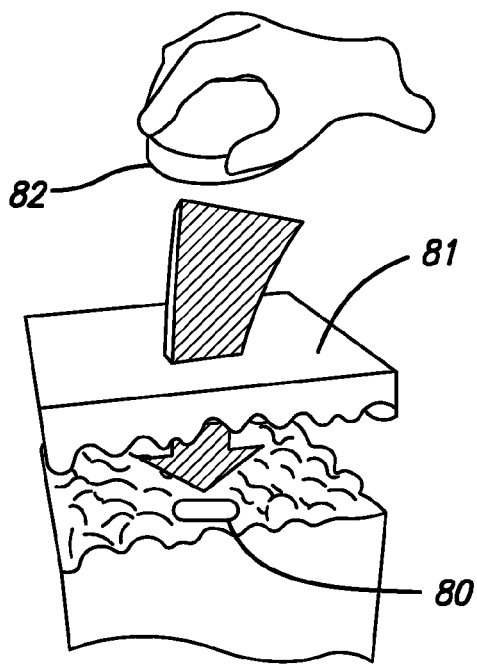
FIGS. 3A-3C show a capsule-based optical sensor implanted under the skin in accordance with an embodiment of the invention.
Figure 3B:
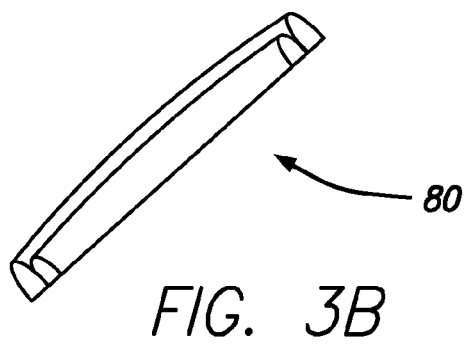
Figure 3C:
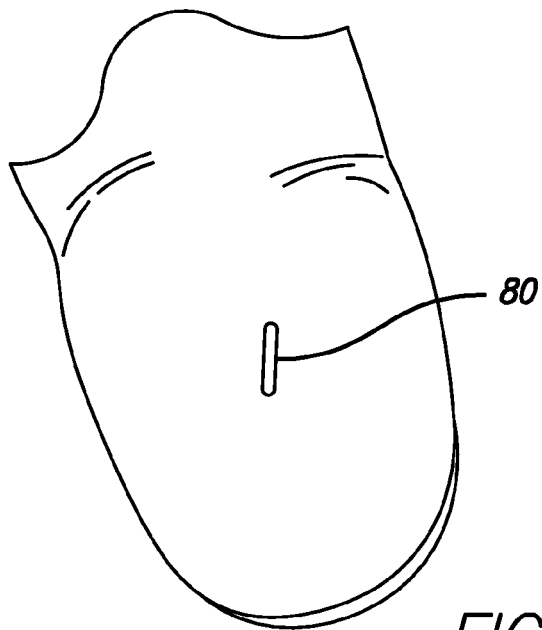

With the above in mind, embodiments of the present invention are directed to an orthogonally redundant glucose sensor that includes an optical based sensor and a non-optical sensor. Thus, within the context of the present invention, in an orthogonally redundant glucose sensor, the above-mentioned electrochemical (i.e., non-optical) glucose sensor may be complemented with an optical based glucose sensor. In one embodiment shown in FIGS. 3A-3C, the optical sensor may be a sensor capsule 80 that is inserted under the skin 81 in the dermal layer, with a reader device 82 positioned above the skin. Light is transmitted between the reader device 82 and sensor 80 through the dermal layer in order to excite the sensing element under the skin, and the resultant fluorescence is measured in the reader device. FIG. 3C shows the relative size of an exemplary optical sensor capsule 80.

Figure 4:
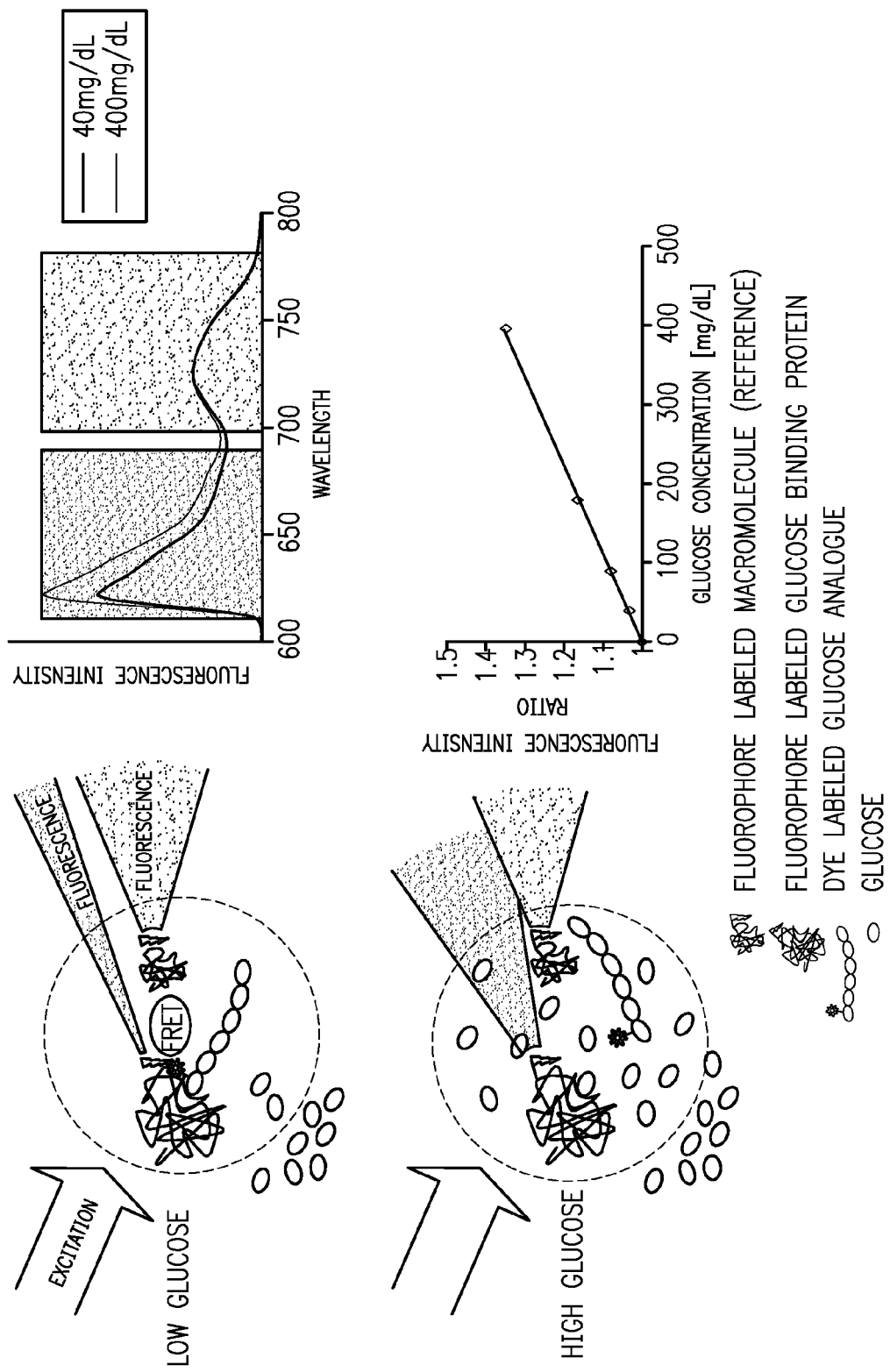
FIG. 4 shows a glucose binding competitive affinity fluorophore-labeled assay, including an internal reference, in accordance with embodiments of the invention.
Figure 5:
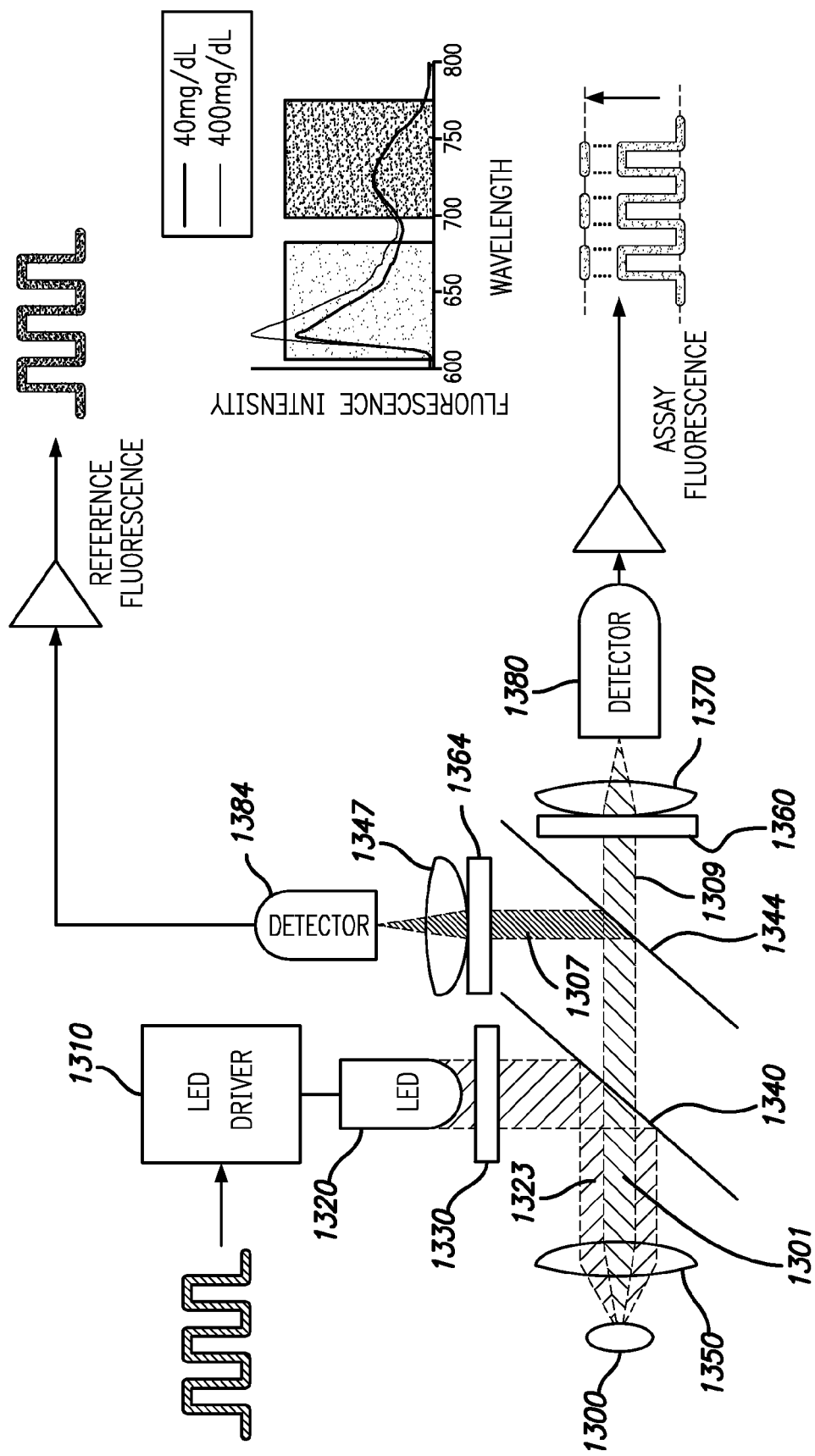
FIG. 5 shows an optical interrogating system for interrogating a fluorophore-labeled assay with an internal reference used for intensity measurement in accordance with an embodiment of the invention.

In an alternative embodiment, shown in FIGS. 4 and 5, the optical sensor may be implemented by employing a transcutaneous optical fiber. Here, the fiber serves as a light guide with the sensing element attached to the distal tip of the fiber. The fiber extends through the skin where it is aligned with the reader device. Light is transmitted between the reader device and the sensing element through the optical fiber.

In one embodiment, the sensing element includes a glucose binding competitive affinity assay surrounded by a glucose-permeable membrane, allowing the glucose within the assay to equilibrate with the glucose present in the surrounding tissue. The assay, in turn, includes a glucose analog (e.g., dextran) and a glucose receptor (e.g., Mannan Binding Lectin ("MBL")) which is fluorophore-labeled to impart fluorescence. The equilibrium between MBL bound to glucose and dextran, respectively, determines the fluorescence intensity in response to illumination of the assay. A non-glucose sensing macromolecule labeled with another fluorophore serves as an internal reference (i.e., a reference fluorophore), wherein the latter emits its own fluorescence in response to illumination. The ratio of the assay-fluorescence and reference-fluorescence intensities is converted into a glucose concentration.

An optical glucose sensor having an assay compartment may be formed, e.g., by including a glucose permeable membrane containing the assay at the distal end of an optical fiber. The optical fiber may then be inserted transdermally into the user's body, thereby situating the assay compartment in the user's tissue, while leaving at least a part of the optical fiber outside the body such that it can be accessed by (i.e., optically coupled to, or aligned with) an interrogating system. Alternatively, the optical sensor may be implantable, e.g., as part of an implantable glucose monitor including an interrogating optoelectronic system and a power source. The assay compartment may be formed between a glucose permeable membrane and an optical interface to the optoelectronic system. The glucose-permeable membrane may preferably be biodegradable.

As noted above and shown in FIG. 4, an optical glucose sensor may be based on a competitive glucose binding affinity assay including a glucose receptor (e.g., MBL) and glucose analog/ligand (e.g., 110 kDa dextran) contained in an assay compartment. The binding between MBL and glucose-like molecules (e.g., dextran) is reversible. When no glucose is present, MBL and dextran will predominantly be bound together. When glucose is added to the assay, it will compete off a part of the dextran population, such that the assay enters a new equilibrium state. The equilibrium state at all times corresponds to the glucose concentration. In order to determine this equilibrium state, MBL is labeled with a donor fluorophore (e.g., Alexa Fluor 594, or AF594), and the dextran is labeled with an acceptor dye (e.g., hexamethoxy crystalviolet-1 (HMCV1)—a proprietary crystal violet derivative manufactured by Medtronic, Inc.). The donor fluorophore and the acceptor dye together form a Förster Resonance Energy Transfer (FRET) pair—i.e., the emission spectrum of the fluorophore and the absorption spectrum of the dye overlap.

The occurrence of FRET affects the lifetime of the excited state and the intensity of the emitted fluorescence and can only occur when the fluorophore and the corresponding dye are in close proximity (i.e., in the range of about 50 Å). Thus, the FRET mechanism permits interrogation of the equilibrium state optically by illuminating the assay and measuring either the lifetime of the excited state ("lifetime interrogation"), and/or the intensity of the emitted fluorescence from the donor fluorophore (intensity interrogation). In some embodiments, the latter approach is preferred, as it exposes the assay to 25 times less light than with the lifetime interrogation.

The FRET mechanism offers several advantages. First, it works transdermally, within an appropriate wavelength range, so that interference from the skin is minimized. Second, FRET fluorescence lifetime measurements are generally insensitive to the relative position of the sensor and the reader unit as long as they are within optical reach of each other, and are also insensitive to changes in the environment, which helps make the system virtually calibration free. Lastly, FRET it considered very sensitive if the appropriate donor-acceptor ratio and suitable donor-acceptor geometry are obtained.

In selecting the FRET pair, the donor fluorophore and the acceptor dye are preferably water soluble, as they are to function in an aqueous environment. In addition, since the sensor is implanted or resident in the body, both FRET components should be non-toxic, as well as stable at 37° C. for at least 2 weeks in the interstitial fluid (ISF). Moreover, fluorescence emission from the FRET pair should be in the red/far-red spectrum to minimize interference from substances in the skin and/or tissue auto-fluorescence.

Resistance to photo-bleaching, i.e., the photostability of both the dyes and the MBL and dextran, is also important. The photostability of the protein originates from its resistance towards Radical Oxygen Species (ROS) generated by the excited dyes, and is an important feature in the stability of the assay. As will be discussed further hereinbelow, this is also a reason why MBL is relatively more resistant to e-beam radiation (wet or dry) than other proteins.

Finally, the donor fluorophore and the acceptor dye must work with a coupling chemistry suitable for protein (preferably amine) conjugation. As discussed above, the MBL molecule may be labeled with a donor fluorophore via the e-amino group on lysine residues using N-hydroxy succinimide (NHS) derivatives of the fluorophore, since this chemistry generates a very stable amide bond between the protein and the fluorophore, and works well in aqueous buffers at pH values that do not compromise the protein.

From an optical point of view, a number of different fluorophores, such as, e.g., Alexa Fluor fluorophores, Texas Red, and Cy5 may be used as fluorophores. However, it has been found that the Alexa Fluor fluorophores work best as they exhibit and/or facilitate several practical advantages, e.g., coupling chemistry, water solubility, photo stability, and quantum yield. Alexa Fluor 594 (AF594), in particular, works well in the conjugation process with MBL; it is commercially available as an NHS derivative and, as such, is ready to be coupled to lysine residues on the MBL molecule.

The single MBL polypeptide has 19 lysine residues which are all potential conjugation sites. The polypeptide organizes in triplexes, each having 3 carbohydrate recognition domains (CRD), that again form higher complexes, usually with 9, 12, or 15 CRDs. It has been found that a degree of labeling (DOL) with AF594 of about 0.8-1 AF594/CRD gives optimal dose-response, with dextran labeled with HMCV1 as ligand. A DOL value that is too high would lead to self-quenching, while a DOL value that is too low would compromise the signal magnitude. It should be noted that, when using NHS as conjugation chemistry, AF594 will be more or less randomly coupled to the 19 lysine residues per polypeptide chain. This means that AF594 sitting on lysine residues in the collagen like domain of MBL, distant to the CRD, may not participate in the FRET, unless the dextran molecule (size 110.000 Da), due to its linear conformation, is able to reach, with an HMCV1 dye, into the Förster space of such an AF594.

As noted, the ligand in the sensor is preferably dextran supplied with amino groups in order to be able to use NHS coupling chemistry for labeling with the acceptor dye. For the latter acceptor dye, hexamethoxy crystalviolet-1 (HMCV1) is preferred over commercially-available acceptor dyes because it is "non-fluorescent"—i.e., it has an absorption spectrum overlapping AF594's emission spectrum, without overlapping AF594's absorption spectrum too much—and works with NHS, i.e., it has a carboxylic group. The above-mentioned non-fluorescence is important, as it helps reduce not only the amount of optical interference with the donor emission, but also the amount of optics instrumentation that is required. In addition, HMCV1 is versatile, such that it can also be used with other fluorophores, e.g., AF647, which is discussed more fully below in connection with use of a red laser diode as a light source.

For certain embodiments, it has been found that approximately 5 HMCV1 molecules per dextran molecule produce optimal dose-response, with the fluorophore-labeled glucose receptor MBL-AF594. Here, a DOL value that is too low would result in inefficient quenching, which would compromise the magnitude of dose-response, while a DOL value that is too high would compromise excitation of AF594, since HMCV1 also absorbs at AF594's excitation wavelengths.

Figure 6A:
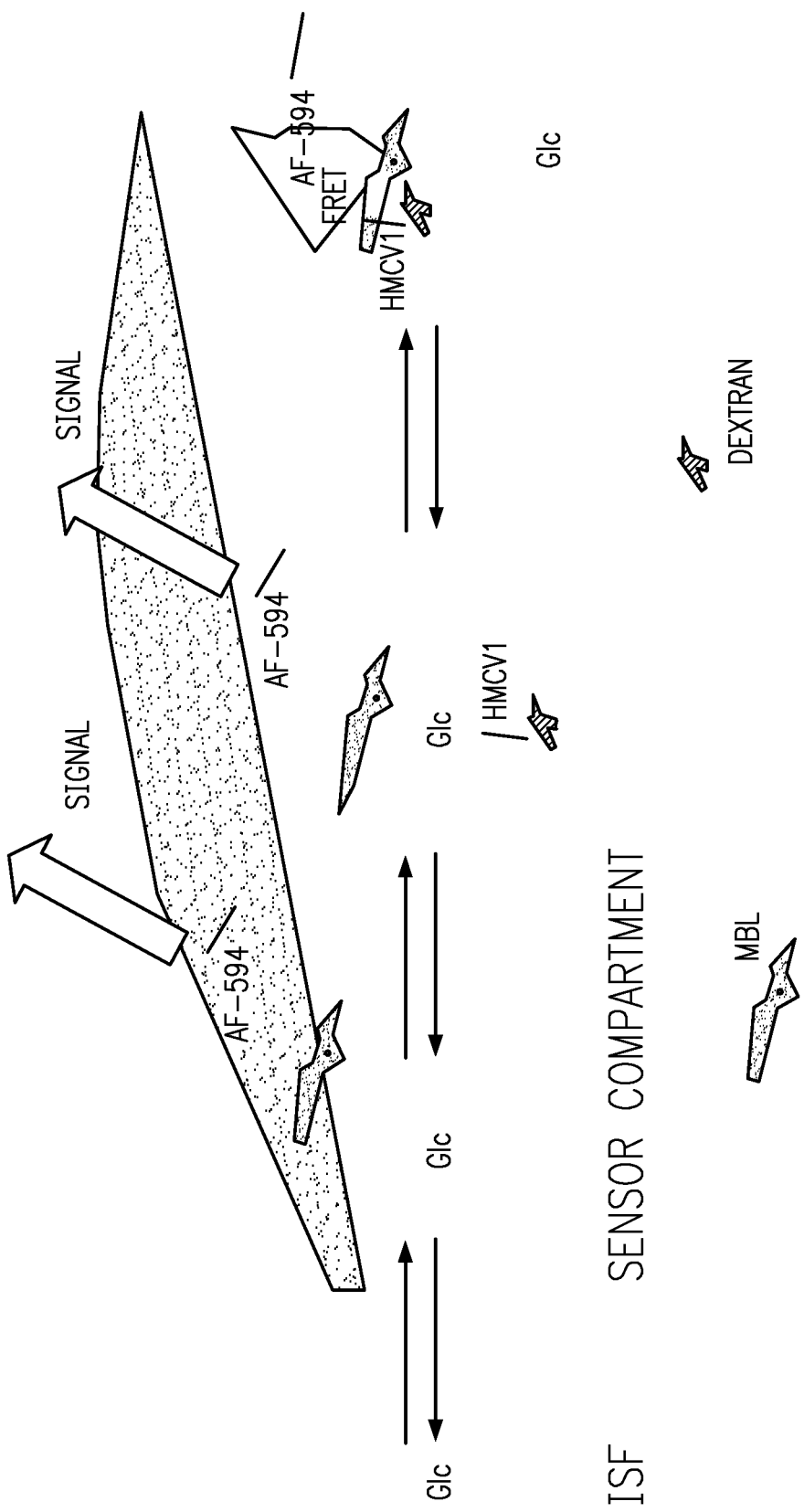
FIG. 6A shows the various equilibria and the non-glucose consuming feature of an optical glucose sensor in accordance with embodiments of the invention.

With reference to FIG. 6A, it is noted that there are actually three separate equilibria involved in the operation of the optical sensor described above. The first equilibrium is the one between glucose in the interstitial fluid and glucose inside the sensor compartment, which is regulated by osmotic pressure, i.e., the difference in glucose concentration in the ISF and inside the sensor compartment. The second equilibrium is the one between the glucose interacting with MBL and free glucose, which is mainly regulated by the affinity between glucose and MBL. The third equilibrium is the one between MBL and dextran, which is regulated by the affinity between dextran and MBL and the concentration of glucose inside the sensor compartment.

All three equilibria are dynamic and reversible. What this means is that the same glucose molecule may at one moment interact with a MBL molecule, and in the next moment be non-interacting with MBL, and in a third moment cross the sensor membrane, leaving the sensor compartment and entering into the ISF. The interaction between the assay chemistry components (MBL-AF594 and dextran-HMCV1) reflects at any time the concentration of glucose in the sensor compartment. Fouling of the sensor—which may potentially compromise the permeability of the sensor—may extend the response time to changes in glucose concentration in the ISF, but does not interfere with the glucose measurement in the sensor. That is, the assay chemistry always measures the correct glucose concentration inside the sensor compartment. In short, fouling of the sensor has no influence on the equilibria inside the sensor. Moreover, all equilibria that involve glucose are fully reversible and, as such, glucose is not consumed in the measuring process.

In contrast with optical glucose sensors, electrochemical glucose sensors are glucose consuming enzyme kinetics based systems. Since the latter reactions consume glucose, sensor response is dependent on glucose diffusion across the outer membrane of the sensor. This can be described by the following mass transfer equation:

$$j = -D\frac{dC}{dX} \qquad \text{Eq. (1)}$$

where j is the glucose flux, D is the diffusion constant, C=[Glu], and X is distance. Bio-fouling changes the thickness of the sensor membrane (dX), thus reducing the glucose flux and measured sensor response. Hence, a sensor re-calibration would be required.

However, since optical glucose sensor technology is not glucose consuming, i.e., it is based on reversible glucose binding to a glucose receptor protein, as detailed above, sensor response depends on the concentration of glucose inside the sensor (assay) compartment. The glucose levels inside the compartment will always be in equilibrium with glucose levels outside the membrane regardless of the thickness of the outer membrane and/or bio-film, because glucose is not being consumed. This equilibrium system can be described by the following equation:

$$K=([MBL-Dex][Glu])/([MBL-Glu][Dex]) \qquad \text{Eq. (2)}$$

Since MBL and Dextran concentration is fixed inside the sensor, K is only dependent on glucose concentration. Since bio-fouling occurs outside the membrane, the equilibrium of the reaction is not affected. Empirical data confirm the above-noted outcome.

Returning to FIG. 5, an optical system used to interrogate the above-described sensing element (assay) is essentially a modified epi-fluorescence set-up with one light source to excite (i.e., illuminate) the assay and two detectors to detect the fluorescence emitted from the assay and the internal reference, respectively. As noted, the intensity of the emitted fluorescence correlates to the glucose concentration. Here, the measured intensity of the emitted fluorescence is affected by the intensity of the light source and the coupling between the assay and the optical system. Therefore, the intensity measurement requires an internal reference fluorophore to be incorporated into the assay.

The reference fluorophore must differ from the assay fluorophore in a way that the emitted fluorescence from the assay and that from the reference may be separated from one another, e.g., by having different absorption spectra or emission spectra. The reference fluorophore may be, e.g., Alexa Fluor 700 (AF700) labeled onto Human Serum Albumin (HAS) or another macro molecule, which largely does not bind to the glucose receptor. Alexa Fluor 700 may be excited simultaneously with the Alexa Fluor 594 as their absorption spectra spectrally overlap. The emission spectrum from Alexa Fluor 700 is slightly red shifted with respect to Alexa Fluor 594, which makes it possible to detect their respective fluorescence emissions in separate wavelength regions.

The excitation, as well as the detection, of the emitted fluorescence for the assay and the reference follow the same optical path from the optical system to the assay. As such, the detected signal from the reference serves as a measure for the optical coupling between the optical interrogating system and the assay. Any effect originating from changes in the optical coupling, such as alignment, may be cancelled out.

With reference to FIG. 5, a driver circuit 1310 modulates a LED 1320 at a low frequency—solely with the purpose of eliminating the 1/f noise and canceling out ambient light—with a wavelength range capable of simultaneously exciting the assay and reference fluorophores. The LED output is filtered using a multilayer dielectrical filter 1330 to select a distinct wavelength region. The filtered LED output is reflected by a first dichroic beam splitter 1340 and focused onto the sensor 1300, which includes the assay and the reference, by a lens 1350.

The assay and the reference emit fluorescence. The emitted fluorescence 1301 and the reflected excitation light 1323 are picked up and collimated by the lens 1350. The first dichroic beam splitter 1340 transmits the fluorescence 1301. However, it reflects the majority of the back reflected excitation light 1323. A second beam splitter 1344 reflects the reference fluorescence at a 90° angle 1307, but it transmits the assay fluorescence 1309. A first emission filter 1360 with a distinct wavelength region red shifted with respect to, and not overlapping, the pass band of the excitation filter and matching the desired part of the assay fluorescence spectrum then blocks the remaining part of the excitation light and transmits the assay fluorescence.

Similarly, a second emission filter 1364 with a distinct wavelength region red shifted with respect to, and not overlapping, the pass band of the excitation filter and matching the desired part of the reference fluorescence blocks the remaining part of the excitation light and transmits the reference fluorescence 1307. Thus, in effect, only the fluorescence from the assay and the fluorescence from the reference are focused onto their respective photo detectors 1380, 1384 using respective lenses 1370, 1374. The ratio between the detected assay fluorescence and the detected reference fluorescence correlates with the glucose concentration in the assay.

The above-described optical sensor technology offers several advantages over other available technologies. For example, as noted previously, due to the non-consuming and stable nature of the assay, the measurement technique is insensitive to bio-fouling. As such, it offers the possibility of one single point calibration throughout the entire lifetime of the sensor. Furthermore, the assay contains a reference dye, which remains stable with changing glucose concentrations, but is affected by many non-glucose induced changes. Therefore, it serves as a sensor diagnostic tool for the optical sensor, indicating when the integrity of the membrane has been compromised or the optical connection is misaligned. See, e.g., FIGS. 6B and 6C. In addition, as will be described further below, the assay may comprise a protective formulation, which is suitable for radiation sterilization, a common sterilization technique for glucose sensors.

Moreover, the glucose receptor, MBL, is a human derived protein. As such, there is no immune response. Moreover, MBL may be derived from plasma or produced recombinantly. In addition, compared to other proteins that may be used for equilibrium-based glucose sensing, MBL has proven biocompatibility and is used clinically for pharmaceutical purposes. FIGS. 50A and 50B show the known differences between MBL and other glucose binders employed for equilibrium-based glucose sensors.

Returning to the continuous glucose monitoring system for orthogonally redundant sensing, the several elements/components shown in FIGS. 1A and 1B will now be described in more detail.

The electrochemical sensor 200 is a state-of-the-art electrochemical sensor, such as, e.g., Enlite3 (third generation Enlite sensor, Medtronic, Inc.). As shown in FIG. 7, the Enlite3 implanted sensor features a distributed sensing electrode design, wherein the sensing electrodes 210 are distributed along the length of the sensor to reduce local tissue effects on sensor performance, as well as optimized solvent-free chemistry to improve consistency. In some embodiments, the electrochemical sensor may consist of a flexible polyimide material with no plastic tubing.

As described previously, and shown in FIGS. 8A and 8B, the orthogonally redundant sensor includes a fiber optical sensor 100. The fiber optical sensor 100 has a fiber 110 with a glucose-permeable membrane 120 attached at/proximate the fiber's distal end 115. The optical fiber 110 may be made of plastic having tensile and fatigue properties that ensure robustness. The glucose permeable-membrane 120 may, e.g., be heat sealed on the distal end 115 of the fiber. In embodiments of the invention, the membrane 120 may preferably be made of a biocompatible, biodegradable polymer such as, e.g., PolyActive™ (Integra Orthobiologics, Irvine, Calif.).

Figure 8B:
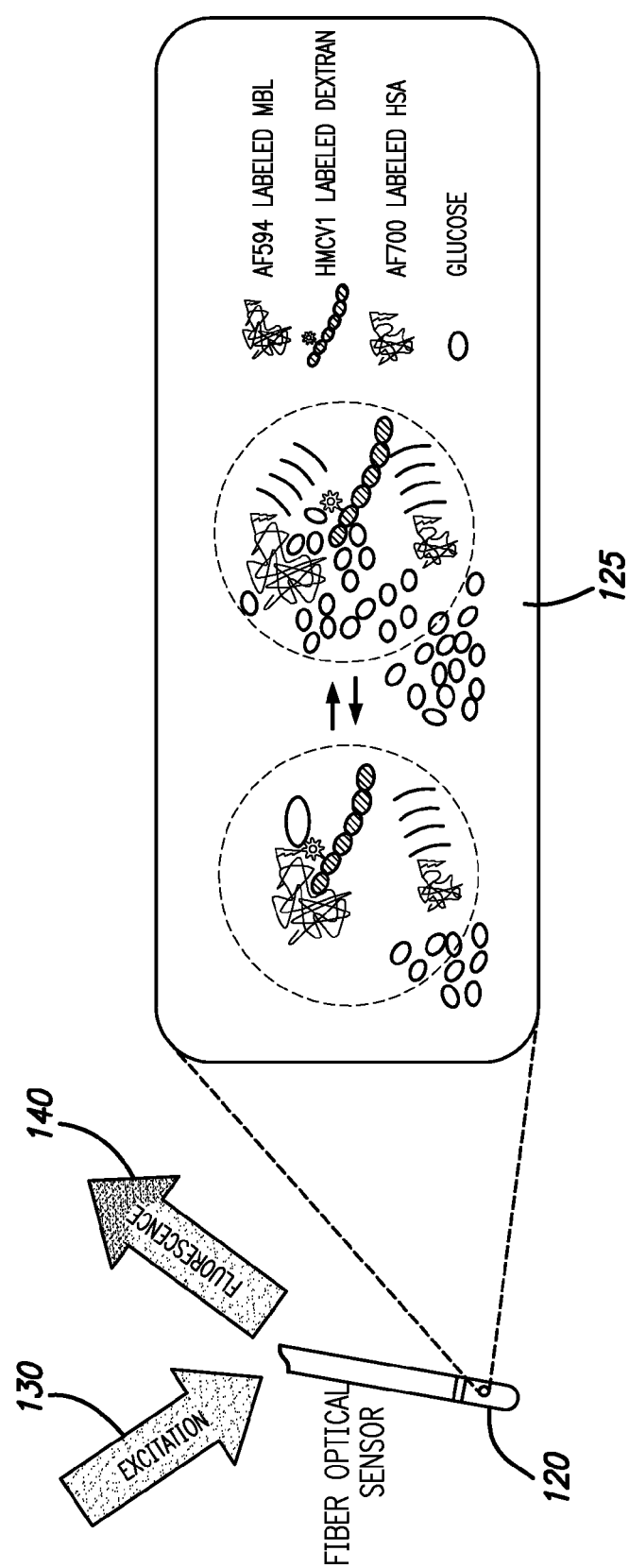
FIG. 8B shows the optical fiber glucose sensor of FIG. 8A, with the details of the assay shown, in accordance with an embodiment of the invention.

The glucose permeable-membrane 120 houses the assay chemistry 125. The size of the optical fiber 110 is optimized so as to improve hydration and response time, as well as to reduce the size of the implant and needle that is used to introduce the fiber into the patient's body. As is also shown in FIGS. 8A and 8B, excitation light 130 travels from the proximal end 117 of the fiber to the assay chemistry 125, and the fluorescence response 140 travels back up the fiber to an optical interrogating system that may be located, e.g., in the transmitter 10 shown, e.g., in FIGS. 1A and 1B.

Figure 9A:
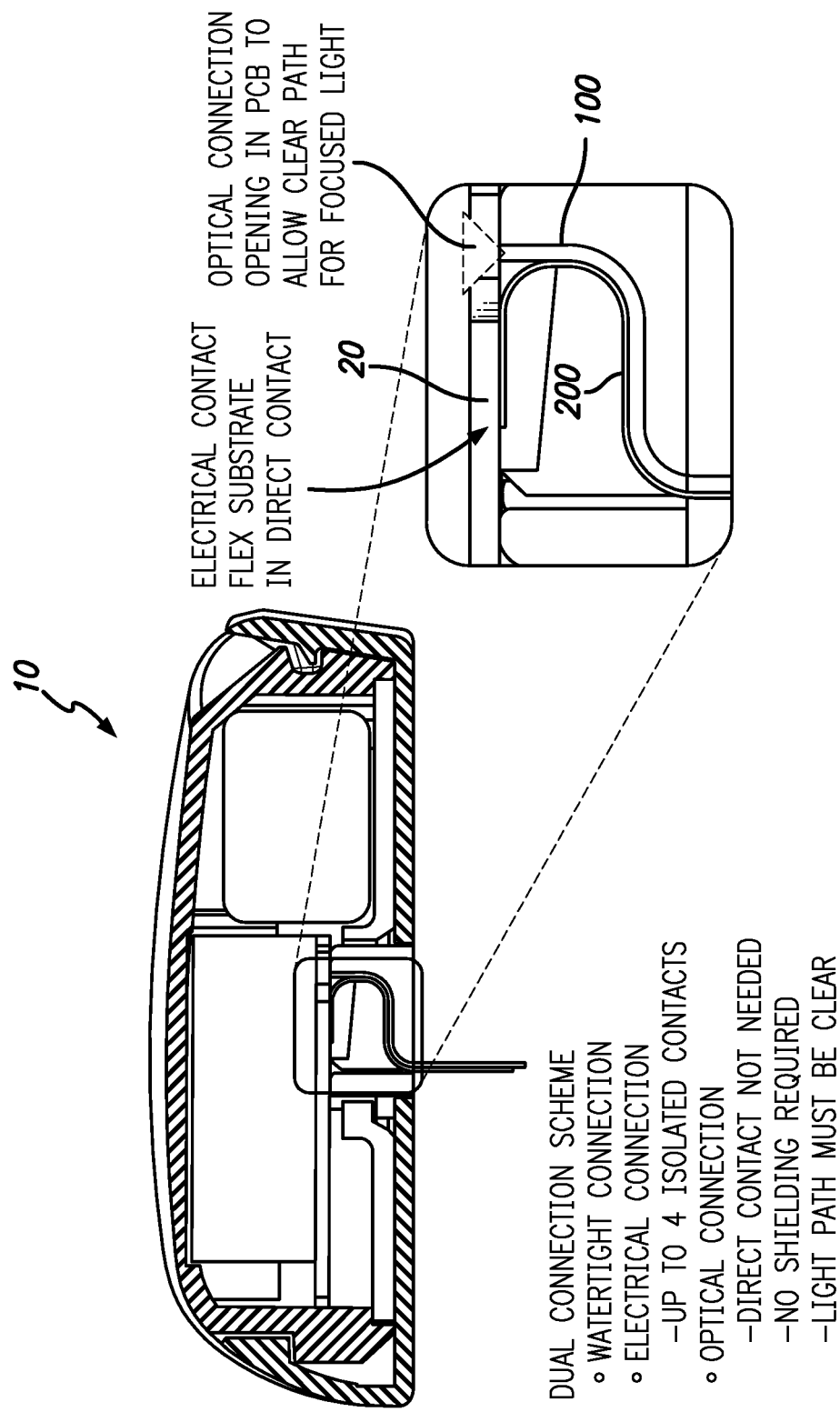
FIG. 9A is a sectional view of a transmitter having a dual connector for connecting to both an electrochemical sensor and an optical sensor in accordance with embodiments of the invention.

The transmitter 10 may include sensor electronics/instrumentation for the optical sensor 100 and the electrochemical sensor 200. For the optical sensor, such instrumentation may include, e.g., a light source, detector(s), optical drive electronics, and other elements/components of an optical interrogation system (discrete or integrated). For the electrochemical sensor, the instrumentation may include, e.g., a potentiostat and other related components (also discrete or integrated). As shown in FIGS. 9A and 9B, the transmitter 10 may also include a dual connector 20 that allows the two sensor elements 100, 200 to separately connect to the required instrumentation. Within the dual connection, the electrochemical connection may allow for, e.g., up to four isolated contacts, and may be watertight. Similarly, the optical connection may be watertight and/or provide for consistent index matching between optical surfaces. Here, while direct contact may not be needed, the light path must be clear.

In addition, the transmitter may house diagnostics, one or more microprocessors and/or digital signal processors (DSPs), memory, a RF communication chip (using, e.g., 2.4 GHz TelD protocol), and a battery to support the measurement functionality of the sensors, the conversion of signals received from the sensors to glucose values, and wireless communication, including transmission of the glucose values (or an averaged, weighted, or otherwise modified version thereof) to, e.g., a monitor 300, an infusion pump 400, a display device, etc.

The transmitter 10 may also house the algorithms that utilize predictive diagnostics and signal comparison to assess signal reliability. The algorithms feature intelligent startup and calibration schemes so that the sensor performance dictates when calibrations are needed. Additionally, the algorithms operationalize the conversion of the individual signals into a calculated glucose number, which is communicated to one or more of the devices noted above.

The transmitter 10 is a durable device and, as such, the associated battery may be rechargeable. In these embodiments, the transmitter may require intermittent recharging of the contained battery. Therefore, in preferred embodiments, a charger may be included for use in conjunction with the transmitter (battery). Additionally, the charger may test the transmitter for proper functionality when required. It is noted that, in some embodiments, some or all of the elements/components that are described herein as being housed in the transmitter 10 may be integrated in order to miniaturize the device. In this regard, a printed circuit board assembly (PCBA) may be used. In some embodiments, at least some of the above-mentioned elements/components may be contained in the monitor 300, the infusion pump 400, a display device, etc.

An insertion device 500 is used to implant the sensors 100, 200 in such a way as to minimize trauma and maximize patient comfort and consistency of sensor delivery. See FIG. 10. The insertion device relies on a disposable, automatically retracting needle 510 that is designed with the sensor base to deliver the sensors 100, 200 through the user's skin. Specifically, the optical sensor 100 and the electrochemical sensor 200 are co-located inside the needle and, as such, are inserted simultaneously.

The electrochemical sensor 200 generally comprises a thin and wide flex substrate. As such, it may be located between the opening of the needle 510 and the optical fiber sensor 100 to aid in retention. The diameter of the fiber sensor may be as large as about 500 µm, but is preferably less than 200 µm. It is noted that, in FIG. 10, the needle 510 is shown at 0° (i.e., horizontally). However, in practice, the needle 510 is inserted at 90°.

Figure 10:
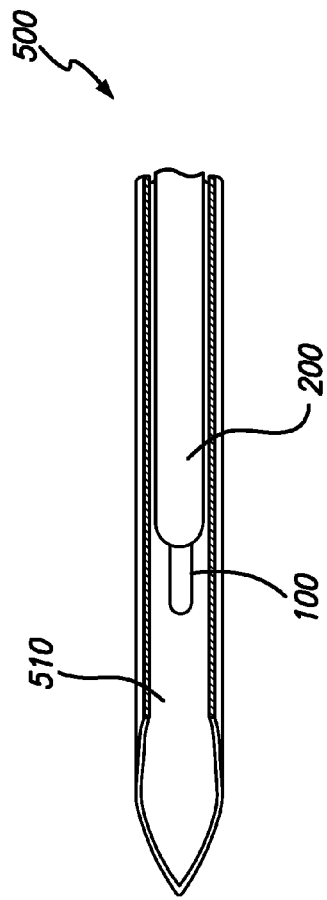
FIG. 10 is a side view of a needle for housing and simultaneously deploying both an electrochemical sensor and an optical sensor in accordance with embodiments of the invention.

As is clear from FIGS. 9A, 9B, and 10, the substrates for the electrochemical sensor and the optical sensor may be fabricated separately and assembled individually into a single base of a single sensor housing (e.g., the transmitter 10). The two sensors are then inserted within a single insertion device 500. However, although the insertion device deploys both sensor substrates together, the substrates are not connected in the implant area.

The electrochemical sensor (probe) and the optical sensor (probe) may, nevertheless, be co-located in vivo. In this regard, it has been discovered that the performance of one of the sensors is not affected by the presence of the other sensor within close proximity. For example, the presence of an optical sensor probe does not shadow or prevent glucose from reaching the electrochemical sensor (probe). Similarly, peroxide, which is produced as a byproduct of the electrochemical sensor reaction with glucose, does not affect performance of the optical sensor. Even at high concentrations of peroxide, such as 12 ppm (i.e., equivalent to a 400 mg/dL glucose response for an electrochemical sensor), peroxide has been found to have no effect on the optical sensor response.

FIG. 9C shows an alternative embodiment, where the substrates for the electrochemical sensor and the optical sensor are integrated so as to form an integrated flex circuit.

Figure 11:
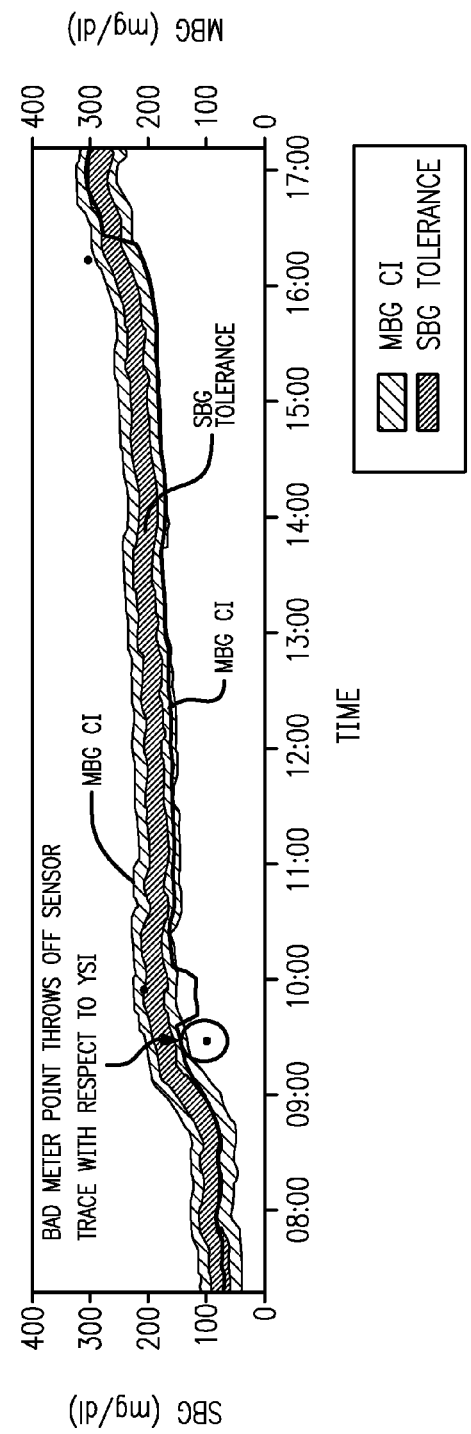
FIG. 11 shows a graphical illustration of an error-check feature based on a meter value obtained from a hand-held monitor with integrated meter in accordance with embodiments of the invention.

The handheld monitor 300, which may also be referred to as "the On Body Controller" or "the On Body Communicator" (OBC), may include an integrated blood glucose meter 320 utilized for calibration. Algorithms within the handheld monitor 300 provide an error check to ensure that inaccurate blood glucose readings are not communicated. Inclusion of this error check has the potential to decrease MARD—and, therefore, increase accuracy—significantly as an incorrect meter point used for calibration can falsely raise or lower calculated glucose levels. See, e.g. FIG. 11.

Accuracy

In the continuous glucose monitoring (CGM) system described above, orthogonal redundancy using two unique sensing technologies provides for increased accuracy and reliability while enabling environmental effects to be accounted for. Specifically, with respect to accuracy, embodiments of the inventions described herein enable a MARD of about 13%. In this regard, it is understood that existing blood glucose meters (i.e., finger-stick) in-home use models are expected to have generally high accuracy; that is, a MARD approximating 9%, with 95% of all points expected to be accurate in terms of ISO 15197:2003. Under the latter standard, a meter is deemed accurate if it meets the following criteria for at least 95% of samples tested: (1) For blood glucose levels below 75 mg/dL, the monitor reading must be within 15 mg/dL of the reference; and (2) for readings of 75 mg/dL or higher, the monitor reading must be within 20% of the reference reading.

For closed-loop ready sensing systems, meter equivalency is not a necessity. Here, the literature has suggested a much looser system accuracy requirement with a MARD of 15% (see, e.g., Hovorka R., "Continuous glucose monitoring and closed-loop systems," Diabetic Medicine 2005(23)). In fact, current-generation CGM systems have published accuracies meeting the 15% requirement, but are accompanied by a large reduction in percentage of samples considered accurate according to the ISO 15197 standard noted above. This deviation in system accuracy may be attributed to multiple factors (e.g., calibrating meter inaccuracy, sensor delay, etc.); however, it is noted that the requirement treats blood samples as independent, discrete events. Contextual (trending, historical) data provided by CGM systems should allow for a relaxation of what is deemed an "accurate" reading.

Reliability

Orthogonal redundancy also allows for a combined reliability that far exceeds the individual reliability of either sensing component. Specifically, as will be discussed further below, two orthogonal sensors with an ISO accuracy of 75% would theoretically be accurate 93.75% of the time when combined. The redundancy increases both accuracy and percent of time data is displayed.

A reliable system requires (1) data to be displayed as often as possible while (2) only displaying data when it is accurate. It is noted that, with improvements to sensor technology and failure detection algorithms, the accuracy of sensor systems will improve significantly. However, failure detection algorithms that are too sensitive might reduce the amount of displayed data to an extent that is unacceptable to the user. In this respect, the reliability of the sensing platform described herein may include the following two components: (1) data display (% of time); and (2) accuracy (% of time).

An embodiment of the system described herein meets the following reliability requirements for 94% of sensors: (1) It displays sensor data 90% of sensor wear "calibrated" time; and (2) it meets ISO 15197:2003 requirements on 93.75% of displayed sampled points. It is noted that some existing sensor technologies may currently meet the first criterion above, but, with regard to the second requirement, significant improvements would be needed in order to achieve near-meter equivalency in terms of ISO 15197:2003.

Existing sensor technology has published accuracy roughly on the order of 70%, meaning that 70% of all evaluated CGM points are deemed accurate according to the ISO 15197:2003 standard. Therefore, assuming two sensing components of roughly equivalent accuracy with random distributions of sensor error occurrence (i.e., assuming that both sensing components will not always be reading inaccurate at the same time), significant gains in accuracy may be realized provided that the system is able to quickly identify possible faults in one or the other sensing component.

Probabilistically, this may be shown as follows:

Let:
S1 be the set of all evaluation points for sensing component 1 (e.g., an optical sensor).
S2 be the set of all evaluation points for sensing component 2 (e.g., a non-optical sensor).
S1 and S2 be independent, normally distributed variables (due to sensor orthogonality).

Then, the probability that for any sample in time either S1 or S2 will be accurate is derived from the additive rule for non-mutually exclusive events:

$$P(a \text{ OR } b) = P(a) + P(b) - P(a) \times P(b) \qquad \text{Eq. (3)}$$

Where
a, b represent whether a point in S1, S2 is accurate (as defined by ISO 15197:2003); and
P(a), P(b) represent the probability that any such point is considered to be accurate.

Using two sensors with P(a)=P(b)=0.7, P(a OR b)=0.7+0.7−(0.7×0.7)=0.91 (i.e., accurate on 91% of points). Thus, any increase in accuracy performance of either sensing component over this baseline increases the accuracy of the overall system as well. FIG. 51 shows individual accuracy effect on an orthogonally redundant system, assuming true independence between the two sensing components.

As noted, the expected combined accuracy is based on anticipated improvements in accuracy to one or both sensing components in order to achieve 93.75% accuracy without sacrificing usable sensor lifetime, and assuming complete independence. In a preferred embodiment of the present invention, where one of the two sensor components is an optical glucose sensor, and the non-optical sensor is an electrochemical glucose sensor, some of the factors that may influence complete independence of the optical and electrochemical sensing technologies include, e.g., the following: (1) sensor co-location within a single implant does not account for physiological effects (i.e., decreased interstitial fluid glucose concentration as a result of increased pressure on the insertion site); and (2) simultaneous calibration of both sensing components relies on an expectation of accuracy from the reference point (e.g., meter finger-sticks) such that, if not correctly identified by the system, a sizeable error from the reference point may propagate into sensor glucose calculation, resulting in distortions of sensor accuracy for both sensing components.

Hypoglycemia Performance

Figure 12:
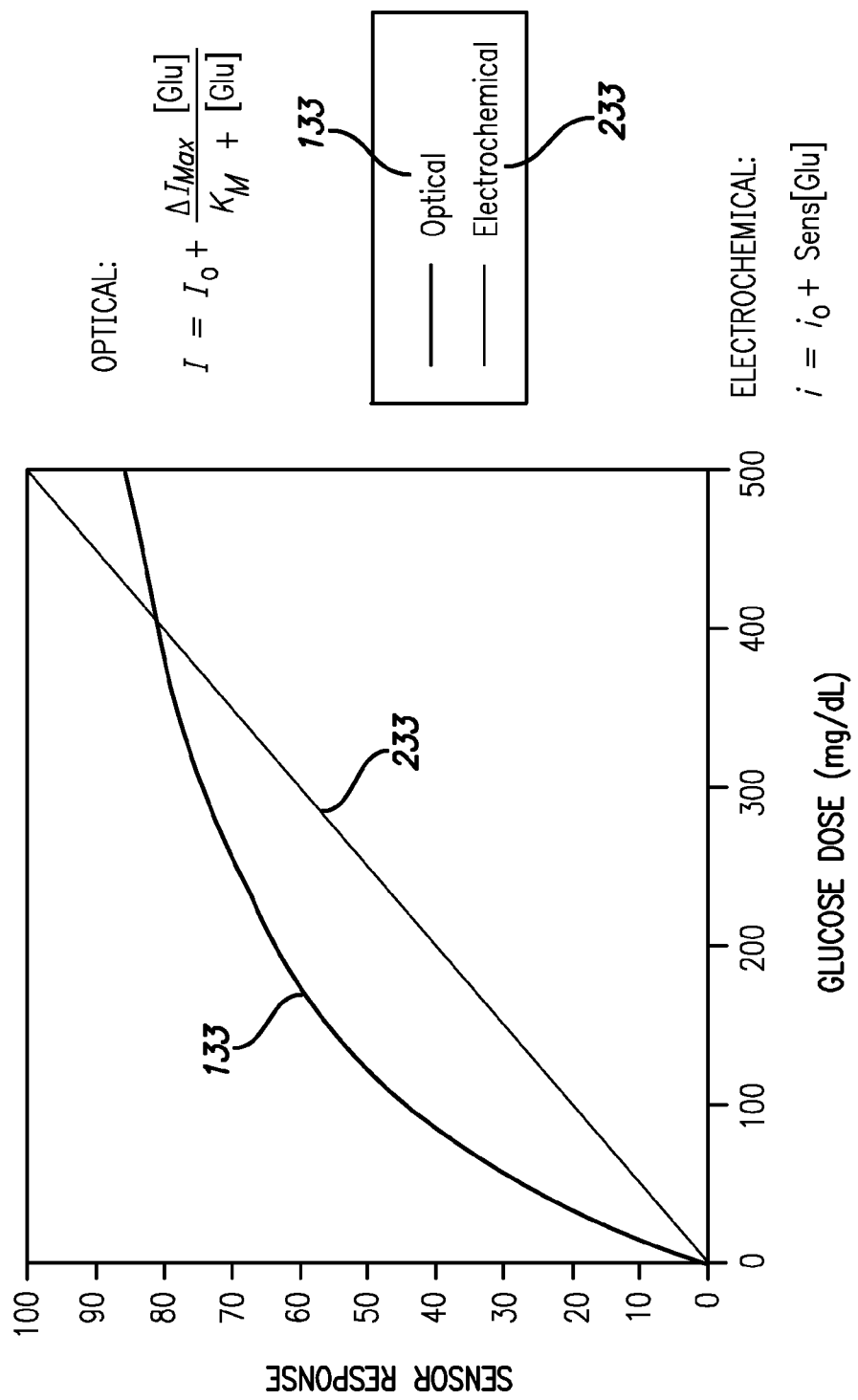
FIG. 12 shows theoretical response functions for an optical equilibrium glucose sensor and an electrochemical glucose sensor in connection with embodiments of the invention.

Combining the optical sensor and the electrochemical sensor yields a sensing system with high precision both in the hypoglycemic and the hyperglycemic range due to the individual dose responses. FIG. 12 shows dose response functions (i.e., the correlation between sensor output and glucose dose) for an optical equilibrium glucose sensor and an electrochemical glucose sensor. The optical sensor features a steeper slope 133 in the hypoglycemic region, leading to higher precision, while the electrochemical sensor has a linear slope 233, resulting in higher precision in the hyperglycemic region.

The established accuracy standards for glucose monitoring devices allow for higher percentage error in the hypoglycemic regions because the clinical treatment decision remains the same regardless of hypoglycemic severity. In closed-loop systems, sensor performance in regions of glycemic excursion (either hypo- or hyper-glycemic ranges) becomes increasingly important, as such systems rely not only on excursion accuracy, but also on contextual trending data as crucial feedback input for control algorithms.

Embodiments of the orthogonally redundant sensor described herein offer benefits in terms of hypo- and hyperglycemic performance. The two glucose sensors have different dose response curves that may improve hypoglycemia and hyperglycemia performance. Equilibrium sensors' dose response function is not a linear function, but a curved shaped function with the steepest slope when approaching a glucose concentration of 0 mg/dL. The steeper the slope in dose response, the higher the precision of the sensor is. Therefore, the affinity-based glucose sensors generally have better hypo sensitivity than hyper sensitivity as opposed to electrochemical sensors, where the dose response function is a linear function resulting in equivalent hypo and hyper sensitivity. Combining the optical sensor and the electrochemical sensor, therefore, yields a sensing system with precision both in the hypo range and in the hyper range.

As noted previously, Hovorka has suggested that, for closed-loop applications, a MARD between 10-15% would be desirable with a preference toward underestimation rather than overestimation. Moreover, the Clinical and Laboratory Standard institute (POCT05-P, "Performance Metrics for Continuous Glucose Monitoring; Proposed Guideline," CLSI) has proposed definitions for home-use hypoglycemic sensitivity, specificity, and false alert rates (for continuous interstitial glucose monitoring) as follows: (1) Sensitivity: for any meter reading below 70 mg/dL, a sensitive CGM system shall also read 70 mg/dL or below within +/−30 minutes of the reference sample; (2) specificity: for any euglycemic meter reading (not hypo- or hyperglycemic), a CGM reading also within this range is considered a true negative; and (3) false alert: for any meter reading above 85 mg/dL, any CGM reading which at that time reads at 70 mg/dL or below will be considered a false alert. The sensitivity/specificity metric allows for consideration of the contextual data provided by the CGM system most relevant to closed-loop control.

In embodiments described herein, the orthogonally redundant sensing system meets a hypoglycemic MARD of 13% with sensitivity and specificity of at least 95% and false alert occurrence rate below 10%. The independent accuracy of each sensor in the orthogonally redundant system meets this requirement in the majority of situations, especially given that orthogonal redundancy allows for elimination of signals that are on the edge, further improving sensitivity/specificity and false alerts.

Reduced Warm Up

Embodiments of the orthogonally redundant sensing system described herein also provide reductions in warm-up time through optimization of individual sensor warm-up time. The overall system start-up time, which is defined as the time until sensor signal is stable enough for performing the first calibration, may be reduced by utilizing predictable run-in behavior and start-up diagnostics as inputs to the algorithm to create an adaptive warm up. Reducing sensor start-up time is important for accuracy and reliability of the system, as well as the user's convenience, as it allows the patient to complete finger-stick calibration soon after inserting the sensor.

With respect to minimization of the individual sensor start-up times, the chemistry layers for the electrochemical sensor may be optimized, and new initialization schemes may be employed in the orthogonally redundant sensor. For the optical sensor, the hydration of the (assay) chemistry may be sped up, and the design may be optimized for a maximized surface area to volume ratio. Hygroscopic agent(s) or chemical(s)—such as, e.g., sugar, honey, and certain salts, which attract and retain water molecules from the atmosphere—may also be added to the assay.

One of the major obstacles to obtaining a fast startup time is to remove air from inside the optical fiber sensor. In this regard, it has been discovered that adding a combination of sugars, bicarbonate, and an enzyme to (the assay of) the sensor gets about 90% of the air out of the sensor within about 30 minutes. Further reduction of start-up time may be possible by optimizing the proportional make-up of the above-identified combination.

Similarly, it has been discovered that smaller-diameter optical fiber sensors provide a reduction in run-in time. For example, replacement of a 500 µm-diameter fiber with a 250 µm-diameter fiber has been shown to reduce run-in times from about 3-4 hours to about 2 hours.

In addition to optimizing the individual sensors, the combined operation of both sensors in one system may also facilitate faster start-up. Predictable run-in characteristics may be incorporated in the algorithm, which helps lower the perceived start-up time, thereby also reducing the number of finger-stick calibrations during this time. Also, as will be discussed further below, intelligent algorithms could compensate for the startup characteristics of each sensor element and any sensor anomalies through a reliability index approach.

In fact, the initial profile of sensors is an important input to early-life sensor diagnostic algorithms. The post-initialized behavior is evaluated by the system to (1) determine the times at which sensors will be ready for initial calibration (adaptive warm up) and (2) identify sensors that are not adequately sensitive to glucose fluctuations (non-critical fault detection).

Advanced Algorithms

In embodiments of the invention, advanced algorithms combine reliability information from each sensor and exploit features of the orthogonally redundant sensors to reduce lag, improve start-up time, and improve accuracy. By comparing signals, faults can be confirmed and self-calibrations can be performed, thereby reducing the number of glucose meter calibrations required.

Figure 13A:
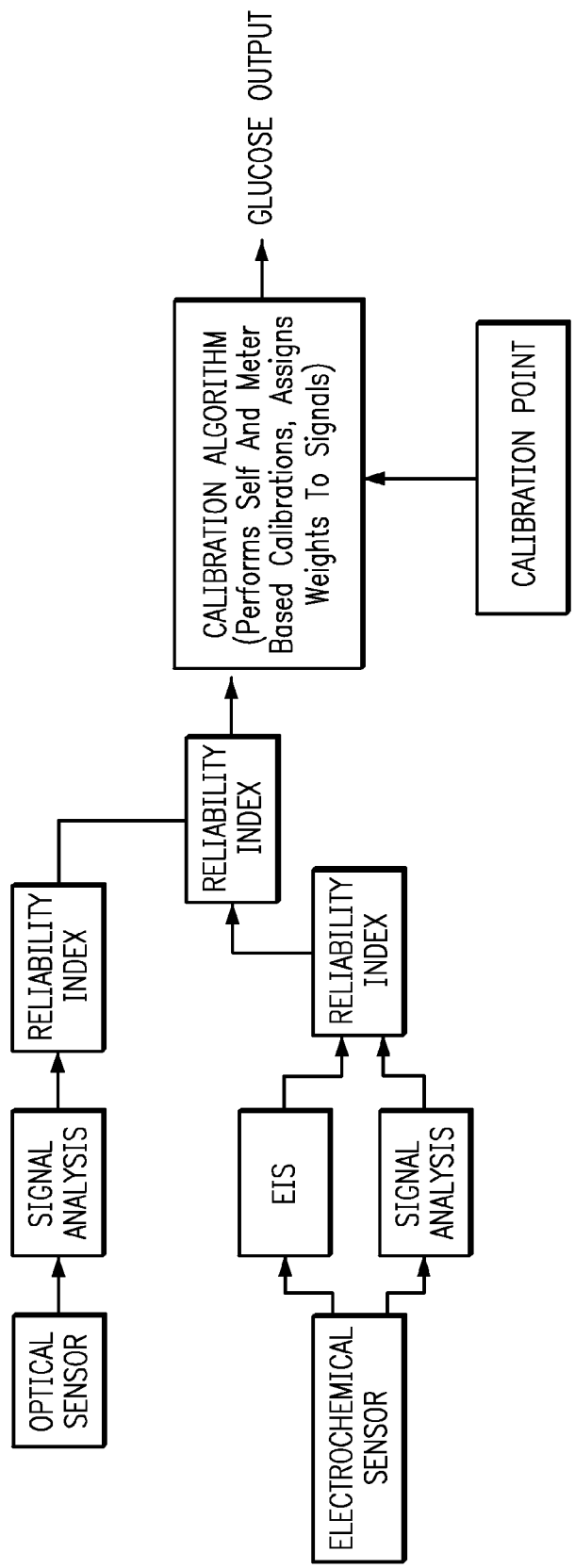
FIGS. 13A and 13B show algorithms for analyzing signals and performing diagnostics to assess reliability of individual signals and assign weights through calibration in accordance with embodiments of the invention.

As shown in FIG. 13A, in one embodiment, an algorithm may take the signals and fault detection of each sensor into account, and then determine the reliability of each signal and weigh them appropriately. The algorithm may also take advantage of the specific benefits of each sensor. For example, the optical sensor generally has a more stable signal compared to the electrochemical sensor, which is known to have a gradual change in sensitivity over time, requiring re-calibrations. With Electrochemical Impedance Spectroscopy (EIS) measurements, or by comparing large recent periods of the electrochemical sensor's signal, instances can be identified where the sensitivity of the electrochemical sensor has changed. The optical sensor will then allow an immediate confirmation of possible sensitivity changes and, if the signal is deemed reliable enough, the electrochemical sensor can be re-calibrated based on the optical sensor. This self-calibration feature reduces the required number of external calibrations, which are typically necessary to maintain high accuracy. In the optimal scenario, calibrations will be needed to maintain confidence in the signal.

While the optical sensor is generally more stable, the electrochemical sensor has other advantages. For example, during the first few hours of start-up, the electrochemical sensor is expected to reach a semi-stable point more quickly, but have a slight increase in sensitivity over the next few hours. As previously described, predictable run-in characteristics can be incorporated in the algorithm.

Figure 13B:
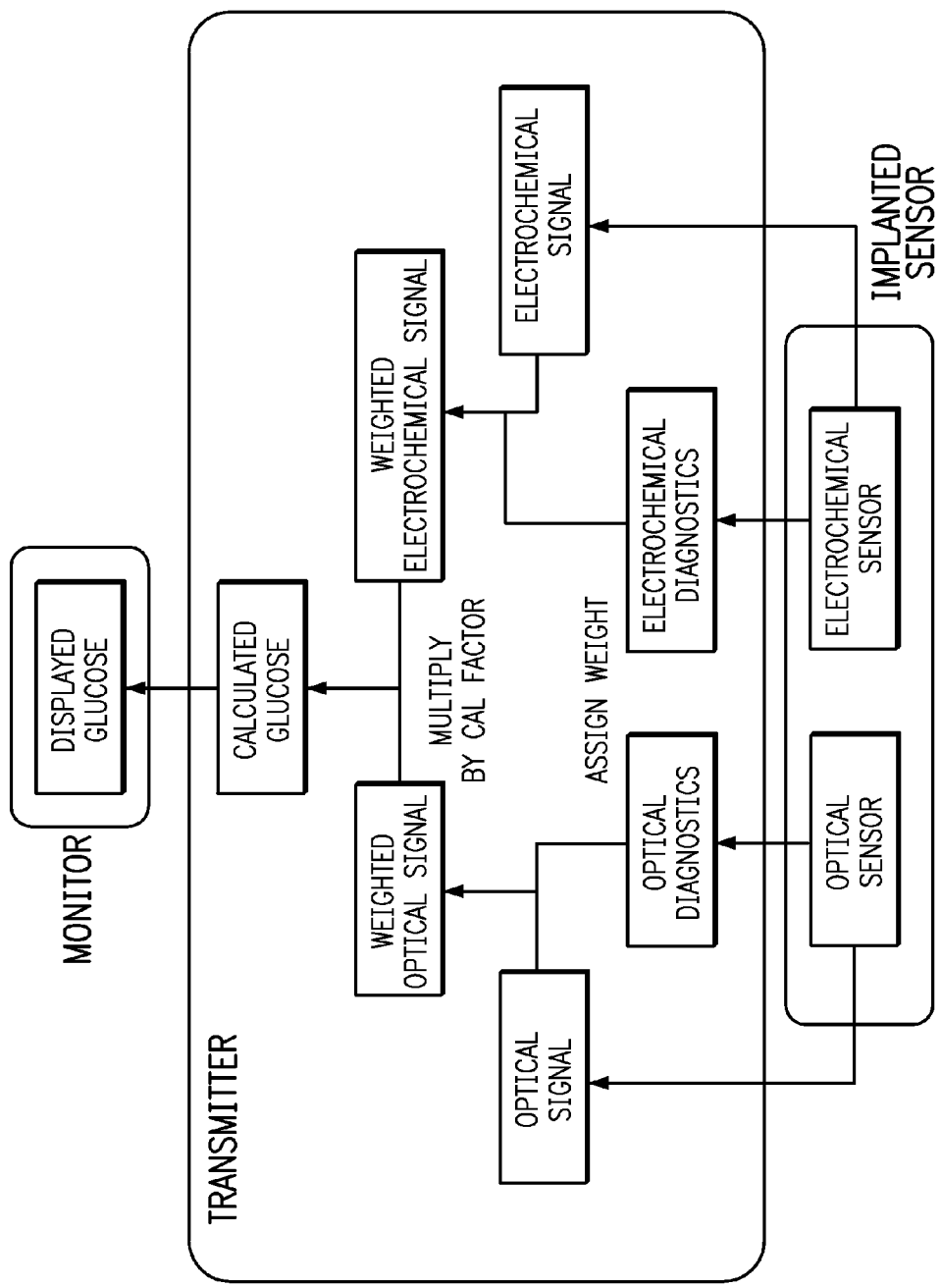

FIG. 13B shows an embodiment in which diagnostics may be used to determine the reliability of individual signals, which signals are then weighted accordingly. The individual weighted signals may then be combined and multiplied by a calibration factor to determine a calculated glucose value. As used herein, the terms "calibration factor", "cal factor", or "cal ratio" may refer to the ratio of blood glucose (BG) to sensor signal. In embodiments of the invention, the "sensor signal" may be further adjusted by an offset value. Thus, for the electrochemical sensor, e.g., the cal ratio may be equal to (BG)/(Isig−offset).

Figure 14:
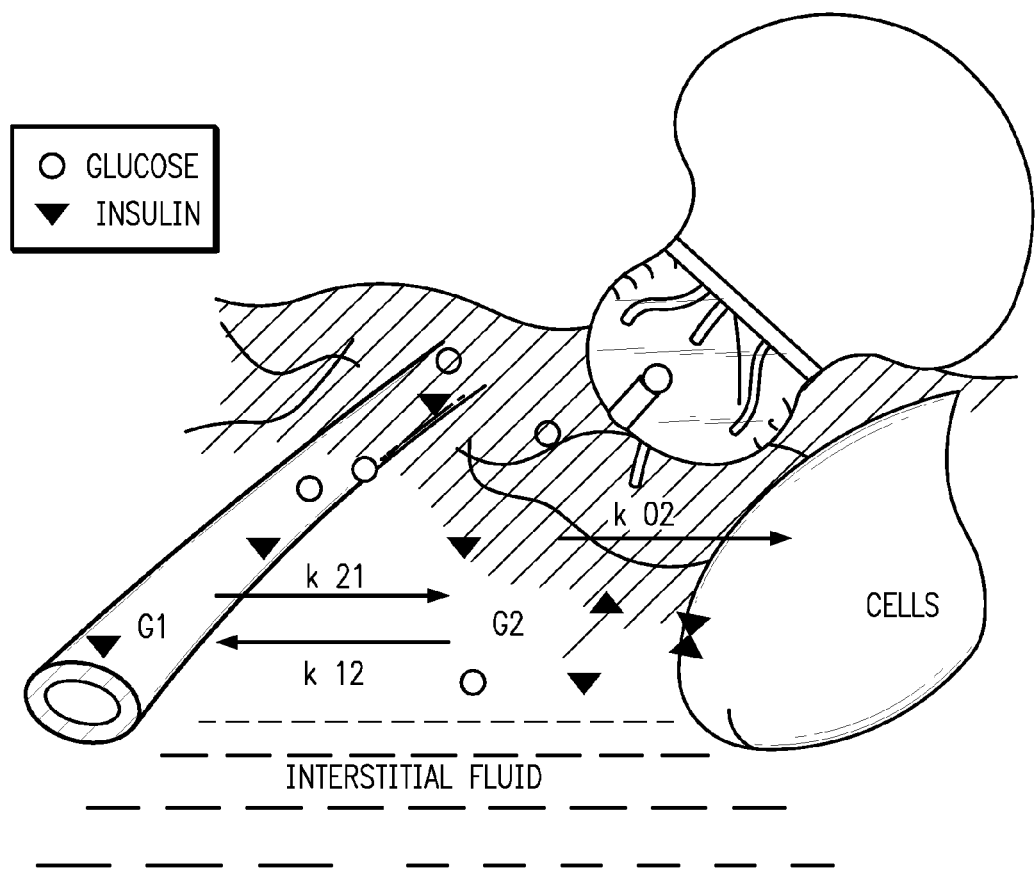
FIG. 14 shows a two compartment model utilized in algorithms for transforming sensor signals into blood glucose values in accordance with embodiments of the invention.

In another aspect, the algorithm may include a model for transformation of the sensor signal to match blood glucose concentration. See FIG. 14. This is done by a two-compartment model, which presumes the sensor is in a different compartment than the calibration measurements. The model accounts for the diffusion of glucose between blood, where calibration measurements take place, and the interstitial fluid space, where the sensor is located. The model also accounts for glucose uptake by cells.

It is expected that the optical sensor may have a slightly longer response time than the electrochemical sensor. The advanced algorithms herein can compensate for this lag by examining each signal's rate of change, and comparing the two signals. Depending on various factors, the electrochemical sensor may detect changes more rapidly. The algorithm needs to detect the change, and if it is unable to compensate for the change, the system may weigh the electrochemical sensor more. Thus, while certain current sensors may perform better when calibrations are taken during more stable periods, incorporation of the two compartment model enables the use of calibrations taken at all times.

Figure 15A:
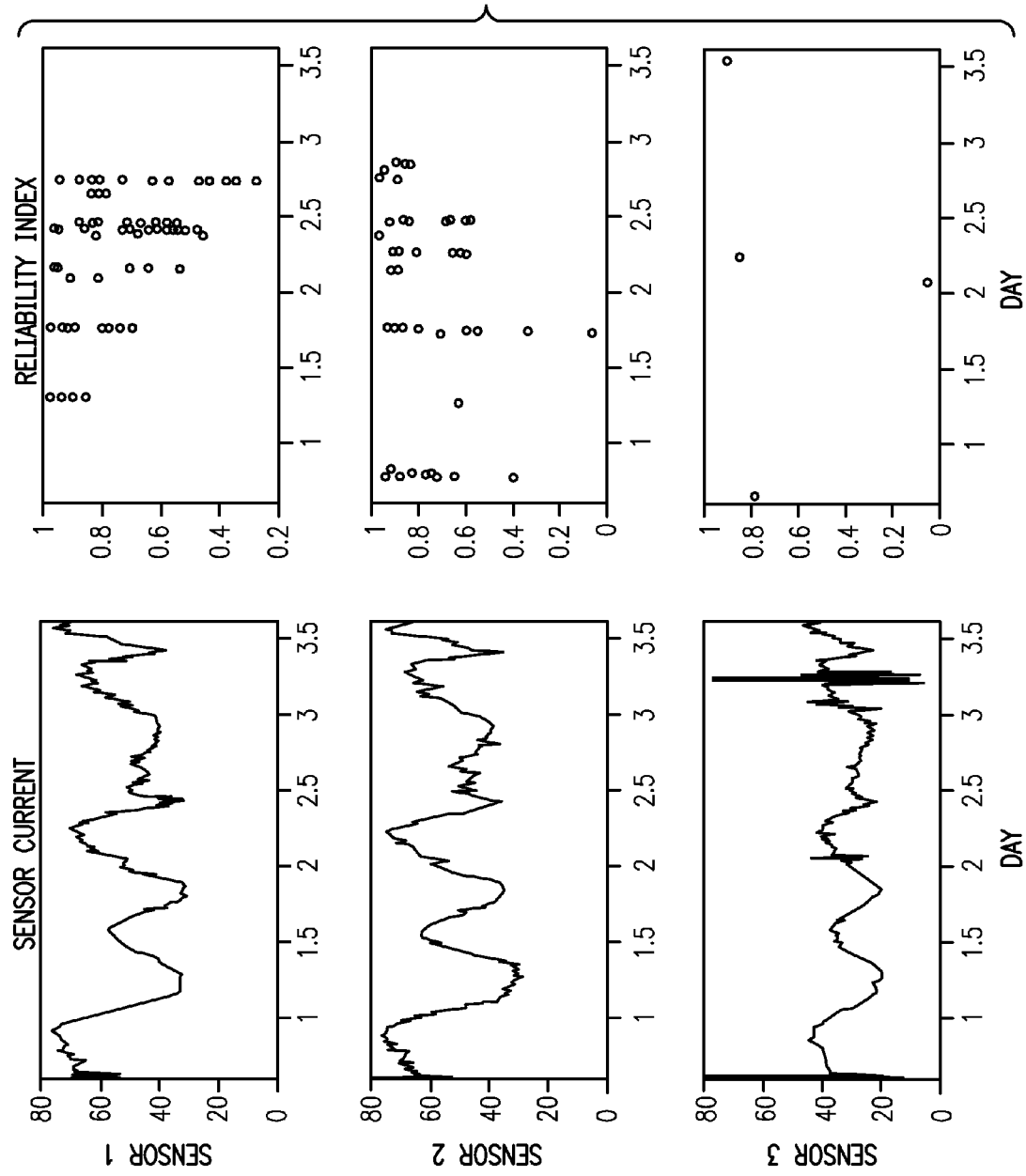
FIGS. 15A and 15B show an illustration of improving sensor accuracy through assessing each individual sensor current with its reliability index (a) and creating a weighted average (b) in accordance with embodiments of the invention.
Figure 15B:
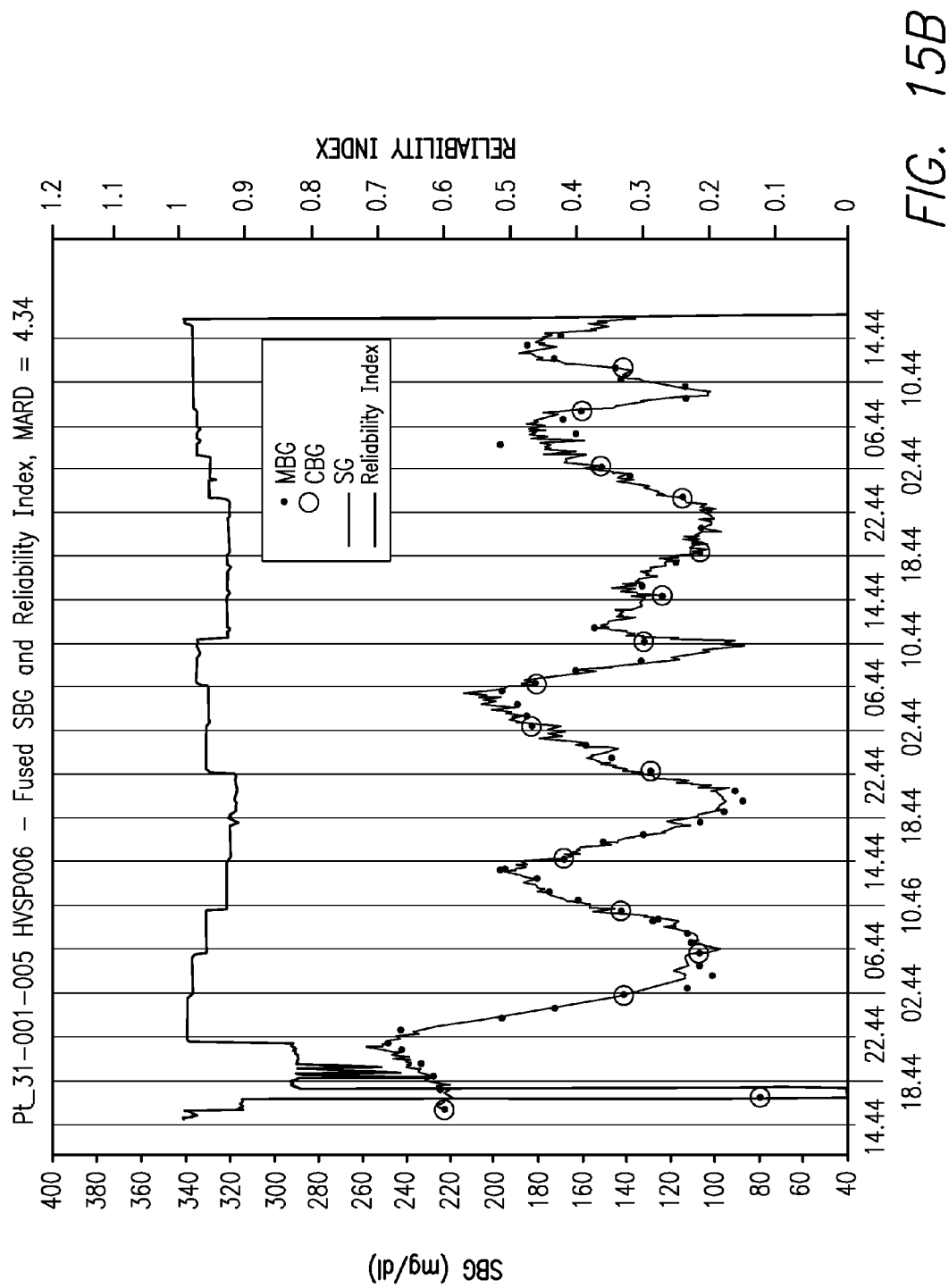

As noted previously and shown in FIG. 13A, a sensor in accordance with embodiments of the present invention may incorporate the benefits of redundancy and sensor weighting using a reliability index. In an exemplary embodiment of the system, multiple electrochemical sensors are evaluated individually, and a reliability index is created for each. In FIG. 15, three sensors are sending data. Individually, each of these sensors would result in an accuracy of about 8%. However, when combined, the accuracy improves to about 4.4%. Thus, sensor accuracy is improved through assessing each individual sensor current with its reliability index (FIG. 15A), and creating a weighted average (FIG. 15B). It is noted that the inventive sensor, sensing system, and associated algorithms herein may be adapted for use at home and/or in a hospital setting.

Figure 16:
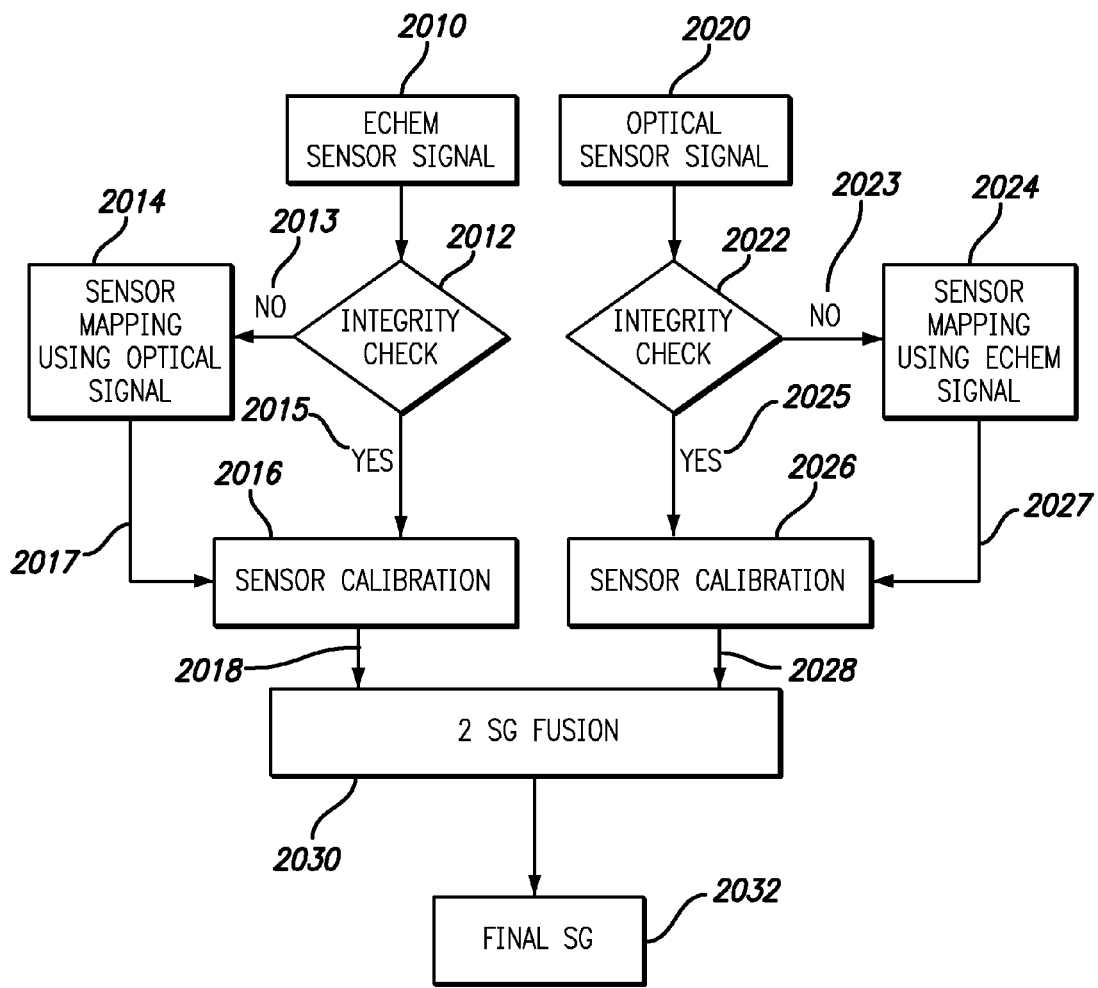
FIG. 16 shows the overall architecture of a calibration and fusion algorithm in accordance with an embodiment of the invention.

FIG. 16 shows the overall architecture of a calibration and fusion algorithm in accordance with an embodiment of the invention. Specifically, the algorithm starts with an electrochemical sensor signal ("echem Isig") 2010 and an optical sensor signal 2020 as inputs on parallel tracks. At step 2012, 2022, an integrity check (to be discussed in detail hereinbelow) is performed for the respective signals. Generally speaking, each integrity check 2012, 2022 may include checking for sensitivity loss (which may be detected as a permanent downwards signal drift), noise, and drift (including an upwards drift, which usually occurs in optical sensors). The latter drift up may be detected by, e.g., comparing the optical sensor glucose (SG) value to the echem SG (assuming the echem sensor is functioning properly), or by checking/monitoring the past history of cal factors and determining that the (optical) sensor is drifting when the cal factor is significantly lower than the historical values.

With each integrity check, if the respective signal is found to be behaving normally, i.e., if it exhibits an amount of noise, drift (either upwards or downwards), and/or instability that is within acceptable limits 2015, 2025, then the signal is calibrated 2016, 2026. If, on the other hand, the signal from one of the redundant sensors (e.g., the echem sensor) exhibits a significant amount of noise, drift, and/or instability, an integrity check on that sensor's signal will fail 2013. However, if the signal from the other sensor (e.g., the optical sensor) is behaving normally, then the latter may be used to correct the unstable (echem) signal via in-line sensor mapping 2014. Similarly, if the optical sensor signal exhibits a significant amount of noise, drift, and/or instability, an integrity check on that sensor's signal will fail 2023. However, if the echem Isig 2010 is behaving normally, then the latter may be used to correct the optical sensor signal using in-line sensor mapping 2024. The mapped (i.e., corrected) signals 2017, 2027 are then calibrated at 2016, 2026.

For the mapping steps 2014, 2024, the mapping parameters may be determined by regressing the optical sensor signal with the echem sensor signal, and the echem sensor signal with the optical sensor signal, as follows:

$$\text{echem\_signal\_buffer}_n = a \times \text{optical\_signal\_buffer}_n + b \qquad \text{Eq. (4)}$$

where "a" and "b" are the mapping parameters and may be determined by using a least square method to minimize any error. Given the time dependence of the data, larger weights may be assigned to the latest data following an exponential decay, where the data may be weighted with a weight of either "0" or "1". In an embodiment of the invention, the buffer sizes of the echem and optical signals in Eq. (4) may be initially (i.e., during the start-up period) set at 3 hours, and then extended to 6 hours once the sensors have been stabilized.

Referring back to FIG. 16, either the echem sensor signal 2015 or the mapped (i.e., corrected) echem sensor signal 2017 is calibrated at step 2016 to produce an echem sensor glucose (SG) value 2018. Similarly, either the optical sensor signal 2025 or the mapped (i.e., corrected) optical sensor signal 2027 is calibrated at 2026 to produce an optical SG value 2028. Thus, for each echem sensor signal 2010, the algorithm will generate a single calibrated SG value as indicated by 2018. Similarly, for each optical sensor signal 2020, the algorithm will generate a single calibrated SG value as indicated by 2028. Finally, a fusion algorithm 2030 (to be described in further detail hereinbelow) is used to fuse the calibrated SG value from the echem sensor with the calibrated SG value from the optical sensor to generate a single (final) SG value 2032.

As noted previously, in the inventive orthogonally redundant sensor system, the optical sensor generates both an assay-fluorescence (i.e., assay signal) through an "assay channel", and a reference-fluorescence (i.e., reference signal) through a "reference channel". The ratio of the assay signal and reference signal intensities (i.e., the "optical ratio") is then used in calculating a glucose concentration. In this regard, the optical sensor signal 2020 is actually the ratio of the assay signal to the reference signal, which ratio is used as a single trace for calibration purposes (to be discussed hereinbelow). The reference channel, however, may also be used advantageously in mitigating noise introduced by optical component misalignment, LED power adjustment, and other potential turbulence in the assay channel from mechanical noise sources.

Figure 17:
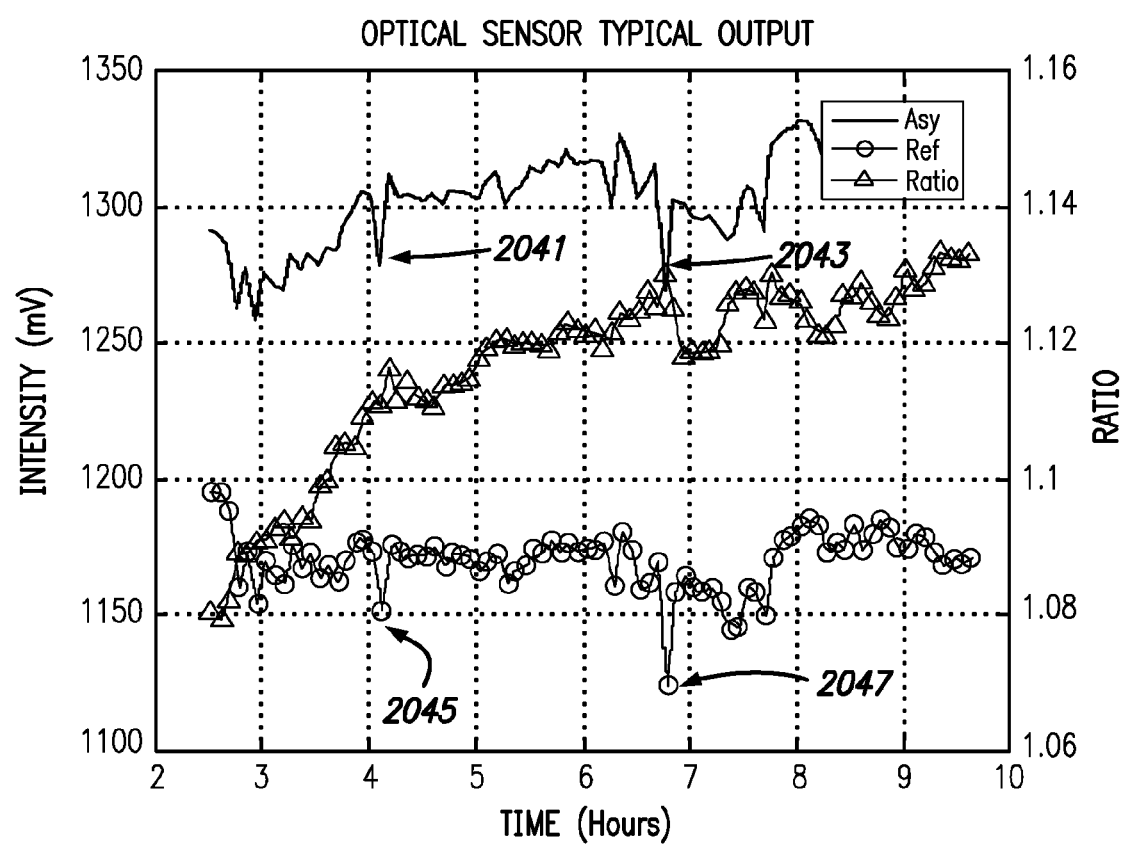
FIG. 17 shows, in accordance with embodiments of the invention, an illustrative example of the signal from a reference channel of an optical sensor tracking the signal from an assay channel of the optical sensor, thereby resulting in a clean ratio trace.

FIG. 17 shows an example of how the signal from the reference channel tracks the signal from the assay channel, thereby resulting in a clean ratio trace. As can be seen from this diagram, the optical sensor output shows two abrupt changes in the assay channel at around 4 hours after insertion (2041) and around 7 hours after insertion (2043). However, because there are similar and corresponding abrupt changes (2045, 2047) in the reference channel, any artifacts are cancelled out, thereby providing a smooth ratio trace.

Figure 18:
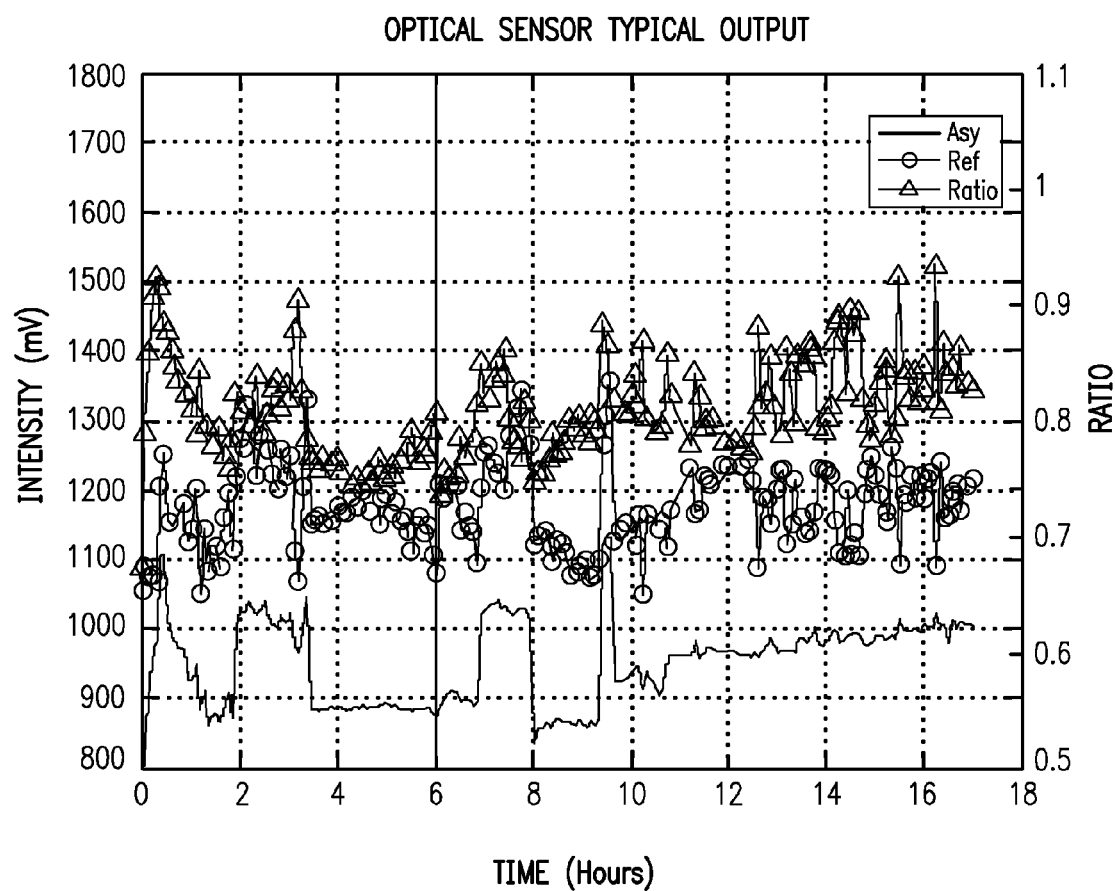
FIG. 18 shows and illustrative example of the impact of noise from the reference channel on the optical ratio.

Nevertheless, there are instances where the reference signal can have a negative impact on the ratio by adding more noise into the ratio (i.e., noise on top of the original noise carried in the assay channel). In general, the major component of noise from the reference channel is severe downwards signal drop, as shown, e.g., in FIG. 18. In the diagram of FIG. 18, no strong noise is present on the assay channel. However, the noise in the reference channel results in a ratio curve with multiple upwards artifacts.

Figure 19:
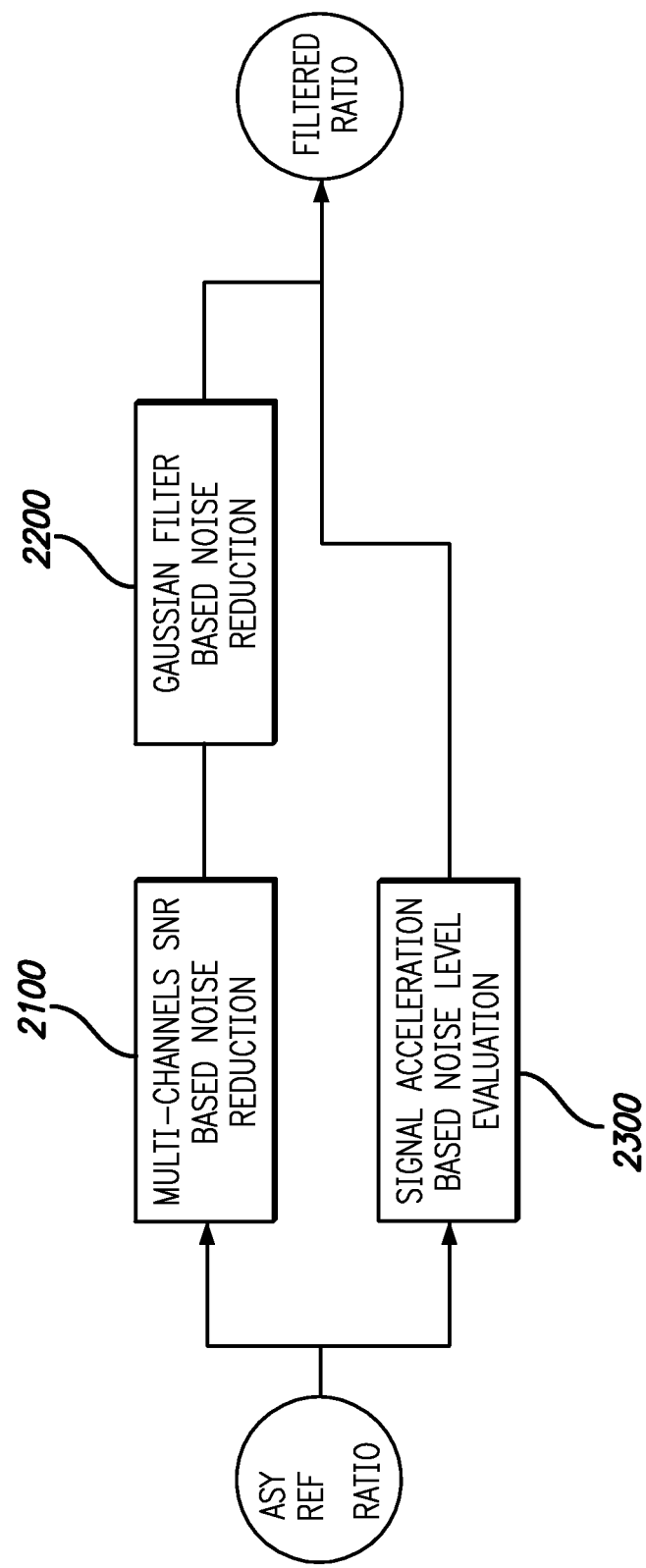
FIG. 19 is a flowchart of in-line noise filtering methodologies in accordance with embodiments of the invention.

To address the above-mentioned noise, embodiments of the present invention utilize noise reduction methods that take advantage of the two-channel setup for the orthogonally-redundant sensor system, using a two-stage noise filtering model to reduce the noise selectively (see 2100 and 2200 in FIG. 19). For instances where the noise is too strong to be used for calibration and tracking glucose, a signal acceleration rate-based noise level estimation method may also be introduced, whose output may subsequently be used as an input for system reliability and failure mode assessment (see 2300 in FIG. 19).

Figure 20:
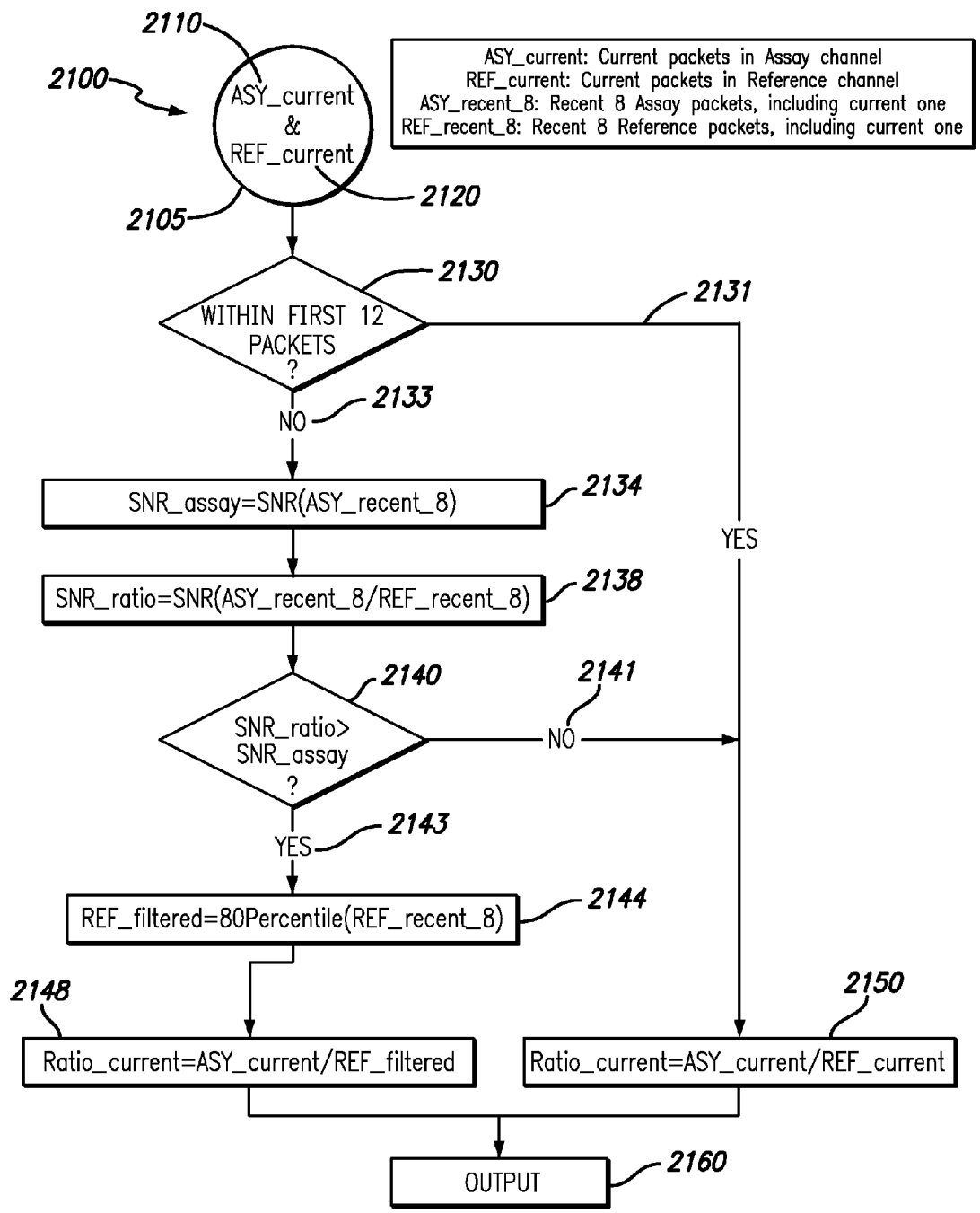
FIG. 20 is a flowchart illustration of a multi-channel signal-to-noise-ratio (SNR)-based noise reduction methodology in accordance with embodiments of the invention.

The flowchart of FIG. 20 shows details of the multi-channel signal-to-noise ratio (SNR)-based noise reduction process (2100) of FIG. 19 in accordance with an embodiment of the invention. In general, during this stage of the process, the SNR of the calculated ratio and the original assay channel are compared. The algorithm continues to use the simple ratio (i.e., assay/reference) if it has less noise than the assay channel, thereby indicating the reference channel's positive impact on the system. On the other hand, once a SNR in the ratio is detected that is higher than the SNR of the assay channel, an 80% weighted outlier filter is applied to the reference channel in order to mitigate the effect of any signal dips, etc. from the reference channel.

Specifically, the logic of the flow chart of FIG. 20 starts at step 2105, where the current (data) packets from the assay channel (2110) and the current (data) packets from the reference channel (2120) are used as inputs. At step 2130, a determination is made as to whether the current assay channel packets and the current reference channel packets 2110, 2120 are among the first 12 packets in the process. If it is determined that the current assay channel packets and the current reference channel packets are, in fact, within the first 12 packets (2131), then the current ratio is calculated as the ratio of the current assay channel packets to the current reference channel packets (2150), and the result is used as the output 2160 of the process.

If, on the other hand, it is determined that the current assay channel packets and the current reference channel packets are not within the first 12 packets (2133), then the signal-to-noise ratio (SNR) of the assay channel is set equal to the SNR of the (most) recent 8 packets, including the current packet, from the assay channel (2134). Next, at step 2138, the SNR of the ratio is calculated as the SNR of the ratio of the recent 8 packets (including the current packet) from the assay channel to the recent 8 packets (including the current packet) from the reference channel. A determination is then made at step 2140 as to whether the SNR of the ratio (2138) is larger than the SNR of the assay channel (2134).

At this point, if it is determined (2141) that the SNR of the ratio is not larger than the SNR of the assay channel, the logic follows the path of 2131, such that the current ratio is calculated as the ratio of the current assay channel packets to the current reference channel packets (2150), and the result is used as the output 2160 of the process. However, if it is determined (2143) that the SNR of the ratio is larger than the SNR of the assay channel, then an 80% weighted outlier filter is applied to the reference channel so as to mitigate the effect of any signal fluctuations from the reference channel. Thus, at step 2144, the filtered value of the reference channel packets (REF_filtered) is taken as the $80^{th}$ percentile of the recent 8 packets, including the current packet, from the reference channel. Finally, the current ratio is calculated as the ratio of current packets in the assay channel to REF_filtered (2148), and the result is used as the output 2160 of the process.

It is noted that, in embodiments of the invention, the SNR is calculated as the reciprocal of the coefficient of variation, i.e., the ratio of mean to standard deviation of the signal or measurement—in this case, assay channel and ratio measurement. However, different mathematical calculations can also be used with regards to different sensor conditions.

Figure 21A:
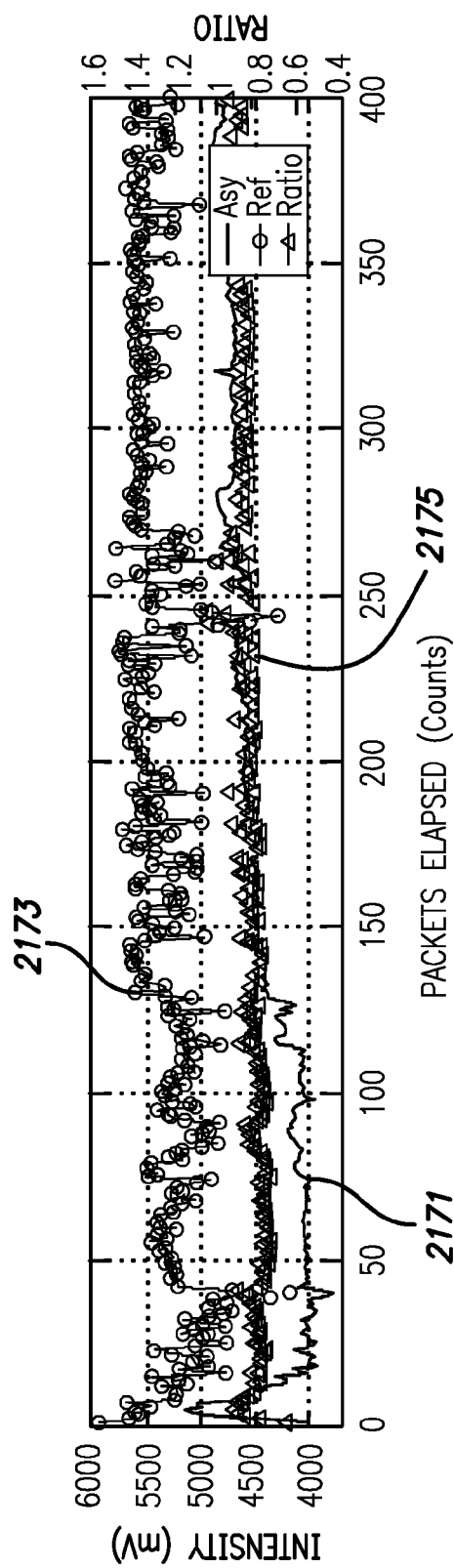
FIG. 21A shows plots of the assay signal (ASY), the reference signal (REF), and the optical ratio (Ratio) based on an optical sensor's raw output signal.
Figure 21B:
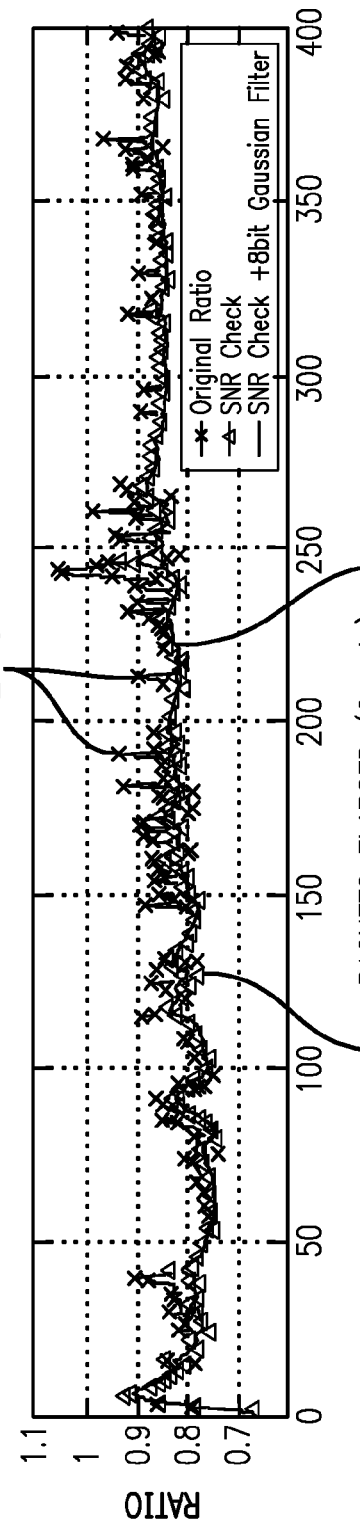
FIG. 21B shows plots of the original optical ratio of FIG. 21A and of the noise-reduced optical ratio in accordance with embodiments of the invention.

As shown in FIG. 19, the output 2160 from the first stage (2100) is next fed into a $7^{th}$ order (i.e., 8 bit) Gaussian Smoothing FIR filter (2200) in order to further reduce the noise. FIGS. 21A and 21B show the results of this filtration process on system performance during periods of heavy system noise. In FIG. 21A, the raw assay signal (Asy) 2171, the raw reference signal (Ref) 2173, and the raw ratio signal 2175 are shown. FIG. 21B shows the noise-reduced optical ratio plotted over a range of ratios between 0.6 and 1.1. In this regard, the plot of FIG. 21A is somewhat more compressed, as the data is plotted over a range of ratios between 0.4 and 1.6 (see right ordinate of FIG. 21A).

Returning to FIG. 21B, the original (raw) ratio 2175, the SNR check 2177 in accordance with the procedure shown in FIG. 20, and the SNR check in combination with an 8 bit Gaussian filter 2179 are shown. As can be seen, the SNR-based method of the first stage of noise filtration reduces most of the upward noise during the first half of the sensor life while keeping the signal envelope complete. In the second stage, use of the Gaussian filter results in further reduction of the noise originating mainly from the assay channel.

In general, high levels of noise suggest unsatisfactory working condition for a glucose sensor, irrespective of the source of the noise (e.g., external environment, internal biology environment, sensor itself, etc.). In certain extreme conditions, the ratio trace shows little or no tracking of glucose when high levels of noise exist. In these situations, an in-line noise evaluation metric may be used in order to determine whether a specific (current) sensor signal is reliable, such that further calculations based on the signal may be performed.

Figure 22:
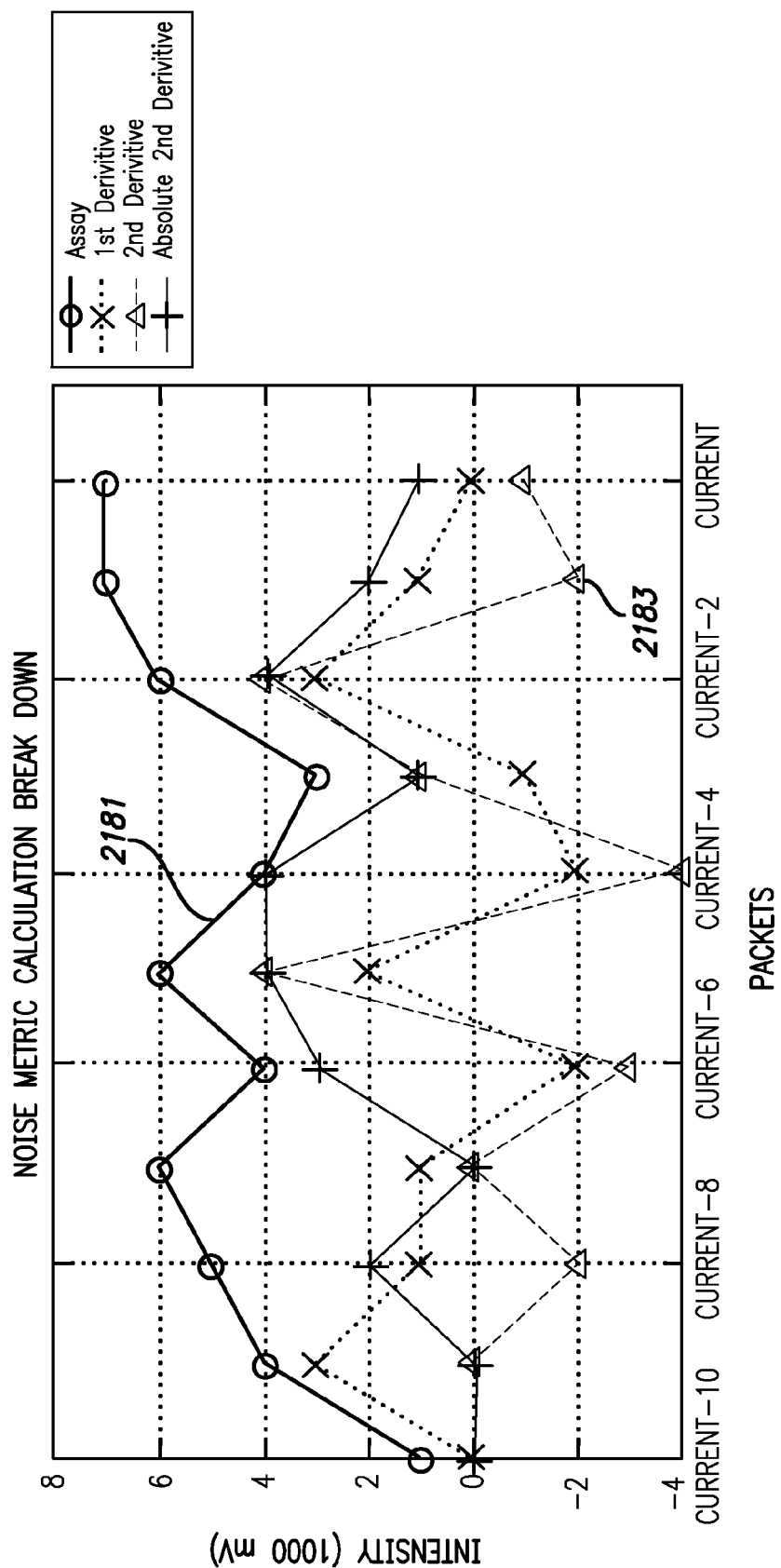
FIG. 22 shows an illustrative example of a noise metric calculation based on the absolute second derivative of the optical sensor assay signal in accordance with embodiments of the invention.

Specifically, in signal acceleration based noise level evaluation 2300 (see FIG. 19), a metric is calculated based on the absolute second derivative (2183) of the assay signal 2181, as shown, e.g., in FIG. 22. For each assay packet with the previous 7 packets available, the metric calculates the average acceleration rate of the previous 7 packets. The calculation is then repeated for 6 packets, 5 packets, 4 packets, and 3 packets. Next, the maximum value among the results of the latter calculations performed with each of 7, 6, 5, 4, and 3 packets is determined, and scaled by a factor, which may be determined from empirical observations. In a preferred embodiment, the factor is 9000. The resultant scaled value is then clipped within 0 to 10. The same calculation is then repeated for all assay packets.

A noise level evaluation curve derived in accordance with the above procedure is shown in FIG. 23B, using the values of FIG. 23A as input data. As shown in FIG. 23B, two particularly noisy periods can be identified: (1) between the $350^{th}$ and the $380^{th}$ packets; and (2) between the $1550^{th}$ and $1600^{th}$ packets. In this particular example, a noisy period has been defined as one in which the ratio noise level is greater than, or equal to, 4. Depending on the specific sensor and application, a different threshold value may be used.

It is important to note that the noise evaluation curve can subsequently be used as a system reliability indicator in formulating a signal compensation strategy, a sensor termination strategy, or both. In this regard, the reliability index can be calculated, e.g., based simply on the percentage of packets, or region under curve integration, for which the noise level is higher than a certain threshold. As mentioned previously, the threshold may be based on empirical observation or derived from user or system based sensor behavior characteristics.

Sensor Drift Detection and Correction

In one aspect, the orthogonally redundant system of the instant invention increases confidence in drift detection by providing an internal reference from which the system is able to verify suspected drifts and confirm sensor deviations without the need for action from the user.

Sensor drift is a characteristic of all sensing systems, and occurs over time or in response to other environmental conditions such as temperature, bio-fouling, etc. Such improvements in sensor design as, e.g., thermal stabilizers, membrane changes, and electrode treatments may be shown to reduce signal drift to levels on the order of 5-10% per day. While a relatively small drift represents an improvement over existing sensors, system requirements for calibration frequency and accuracy must allow the system to account for these deviations.

In embodiments, the inventive system and related algorithms herein identify cases of significant sensor drift (in both sensors), and either account for the detected drift or halt glucose display to the user until the potential fault is resolved, e.g., by calibration. In this way, drift detection is realized through signal analysis and is one parameter that is fed into the system reliability index (see, e.g., FIG. 13A and FIG. 38).

Independently, the electrochemical and optical glucose sensing systems are able to do some amount of self-diagnosis of sensor drift simply by evaluating periodic sensor behavior and how it changes over the course of sensor life. As discussed previously, the non-glucose consuming nature of the optical sensor chemistry offers the benefit of being insensitive to bio-fouling. Since the glucose sensitivity is not dependent on diffusion rate across the membrane, sensor drift through bio-fouling is generally not a concern.

In one aspect of embodiments of the invention, the drift component of a signal may be determined or estimated, and corrected for, via mathematical modeling using either a moving-average approach or regression. Specifically, a measured signal y(t) at discrete time t is known to drift over time, so that it is composed of the true signal x(t) plus a drift component z(t).

$$y(t)=x(t)+z(t) \quad \text{Eq. (5)}$$

Using the following definitions, the aim is to identify z(t) from y(t), under the assumption that z(t) is a relatively smooth and slowly varying low order polynomial. The error between the estimated drift $\hat{z}(t)$ and the real drift z(t) should be minimized so that x(t) can be reconstructed most accurately:

y(t)—measured signal (including drift) at time t.
z(t)—the real drift at time t.
$\hat{z}(t)$—an estimate of the drift z(t) at time t.
x(t)—true signal (without drift) at time t.
$\hat{x}(t)$—an estimate of the original signal x(t) at time t.

By obtaining an estimate $\hat{z}(t)$ of the drift component, the real signal can be reconstructed as:

$$\hat{x}(t)=y(t)-\hat{z}(t) \quad \text{Eq. (6)}$$

It is assumed that changes in z(t) occur over time, but that these changes are slow. Two methods of obtaining $\hat{z}(t)$ are discussed immediately below: moving average and regression.

Moving Average

Computing a moving average assumes that z(t) can be explained by its average signal level—that is, high rates of drift will exhibit higher average signal magnitude than those with low rates of drift. A moving average is computed at each time t by sliding a window of observation of length $T_0$ over time. That is, $$\hat{z}(t) = \frac{1}{T_0} \sum_{T=t-T_0}^{t} y(T) \quad \text{Eq. (7)}$$

In Equation 7, configurable parameters include the length of the window $T_0$, as well as the overlap between successive windows. The value of $T_0$ should be made sufficiently large so as to average out fluctuations in x(t), but short enough to react to time-dependent changes in z(t). In the case of glucose sensing for monitoring diabetes, it may be assumed that the drift is much slower than typical swings observed in diabetic blood glucose levels. For this application, values of $T_0$ may be, e.g., about 0.5 days and larger, up to several days long.

The overlap between successive estimates of $\hat{z}(t)$ determines how often the computation is made. Thus, there is a design trade-off between computational expense, on the one hand, and more-frequent tracking of changes in drift, on the other. In a glucose sensor, it is generally not expected that drift will change dramatically. As such, overlap in successive computation windows can be decreased (e.g., up to 2 hours or more, depending on the level of drift). If computational expense is not an issue, then $\hat{z}(t)$ can be computed at every available sample of (t).

In embodiments of the invention, depending on the specific application, it may be appropriate to modify the estimate of $\hat{z}(t)$ by applying greater weight to some data than to others. For example, more-recent data may be more relevant to the estimate of drift than older data if, e.g., a sharper-than-normal or nonlinear change in drift occurred at some point in the past. To account for this, the values of y(t) within the computational window may be multiplied with an exponentially (or linear, or any other) decaying function of time, prior to computing $\hat{z}(t)$.

As another example, some data may be more useful in estimating drift than others if, e.g., there is a sensor malfunction and abnormally low currents are being generated. This may be accounted for by applying, prior to estimating $\hat{z}(t)$, a weighting function that emphasizes currents within a normal range. The weights may be used to give greater importance to values within normal ranges, or to exclude values outside a specific range altogether.

It is noted that the above-described weighting schemes are illustrative, and not restrictive, as other forms of weighting may be used, depending on the specific sensor, environment, application, etc.

Regression

To estimate $\hat{z}(t)$ using regression, a choice must be made about the underlying model that best describes z(t). When a moving average is used, the assumption is, effectively, a single parameter model—that is, that a single constant can describe the characteristics of the drift during the window of observation. More complex models can be assumed—for example, a linear relationship, where two parameters need to be estimated, or more complex higher-order polynomials where several parameters must be estimated.

Regression is used to estimate the parameters that best fit the data. For a linear model, it is assumed that a relationship of the type z(t)=mt+c exists, and regression is used to estimate the values of m and c that minimize the difference between the measured z(t) and the estimated $\hat{z}(t)$. Various standard algorithms exist for estimating optimal parameters of an assumed model (such as, e.g., least mean squares or LMS, maximum likelihood estimation, and Bayesian linear regression), as well as ensuring that the estimates are robust (e.g., robust LMS). Thus, for purposes of the ensuing discussion, it is assumed that robust estimates can be made when sufficient data is available.

Where, as here, there exists a measurement of y(t) rather than z(t), it is still possible to obtain the estimate $\hat{z}(t)$, so long as the characteristics of z(t) and x(t) are separable. This can occur, for example, when the frequency content of x(t) is much higher than that of z(t); in other words, when changes in z(t) occur at much larger timescales than x(t). If frequency content is not sufficiently distant from each other, then fluctuations in x(t) can affect the estimate $\hat{z}(t)$. The level of crosstalk will depend on the nature of the data under consideration.

To account for changes of z(t) over time, regression is applied over a window of observation of length $T_0$, as was done previously for the example using moving average methodology. The window is shifted in time and a new regression is performed using this updated data. Here, the configurable parameters include the length of the window $T_0$, as well as the overlap between successive windows. As with moving average, the value of $T_0$ should be made large enough to average out fluctuations in x(t), but short enough to react to time-dependent changes in z(t). Possible values of $T_0$ and overlap are the same as those discussed for moving average. In addition, weighting can also be applied in the same way(s).

With the above in mind, an illustrative example is presented herein using the optical ratio of the orthogonally redundant sensor described hereinabove, which sensor is known to exhibit drift over time. For purposes of the illustrative example, drift is assumed to be a linear function, and the regression is estimated using Robust Least Mean Squares methods. For both moving average and linear regression, the estimate of ẑ(t) started at t=0.5 days, and data before t=0.2 days was excluded. The computation window length was initially $T_0$=0.3 days, and was allowed to grow up to $T_0$=1.5 days. When more than 1.5 days of data became available (at t=0.2+1.5=1.7 days), the window was shifted in time with maximum overlap—that is, ẑ(t) was recomputed at every new available sample (in this case, every 5 minutes). No weighting function was used; that is, all values within the computational window were given equal weight.

FIG. 24A shows the raw optical ratio signal 2301 measured in a diabetic dog prior to drift correction. Also shown in FIG. 24A is the identified (estimated) drift when both moving average (2303) and linear regression (2305) algorithms are applied to this data. FIG. 24B shows the drift-corrected ratio for each of these methods. Moving average (2311) and linear regression (2313) both identify the upward drift, although moving average appears to be more affected by swings in glucose.

Figure 25A:
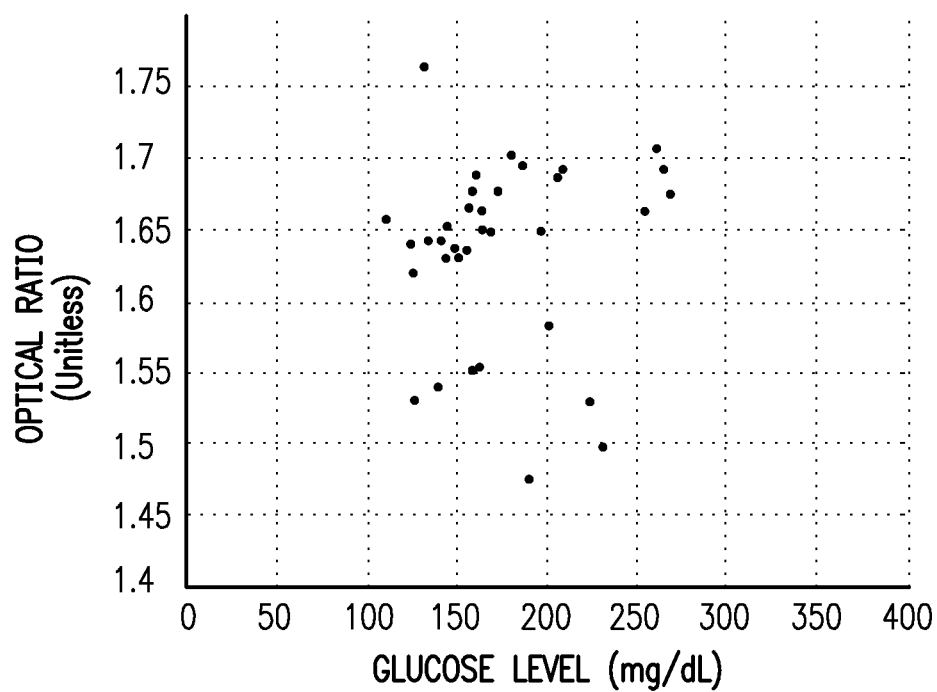
FIGS. 25A-25C show the effects of drift correction on the optical ratio in accordance with embodiments of the invention.
Figure 25B:
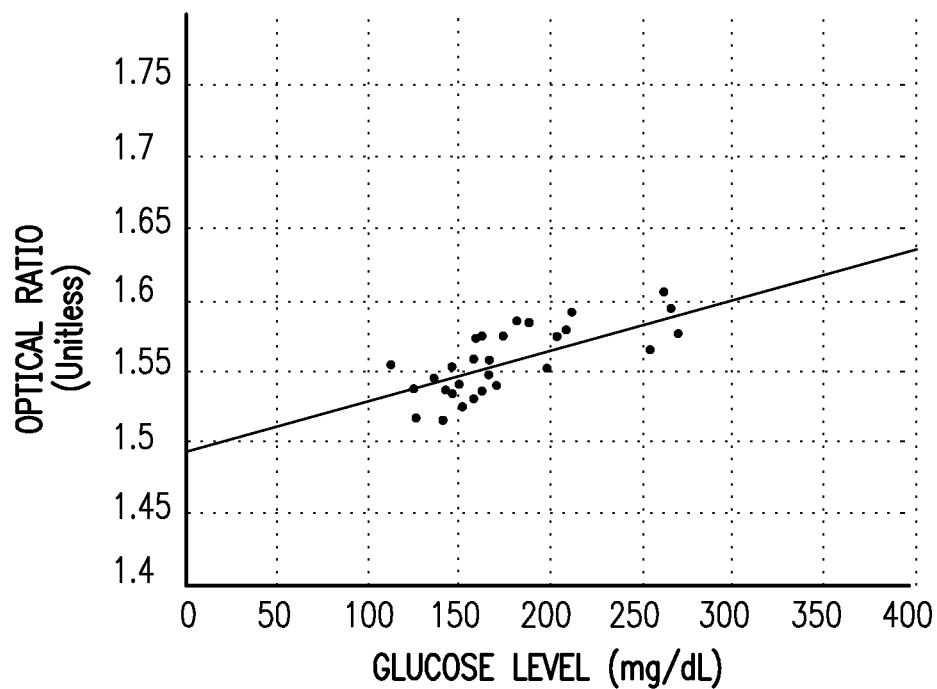
Figure 25C:
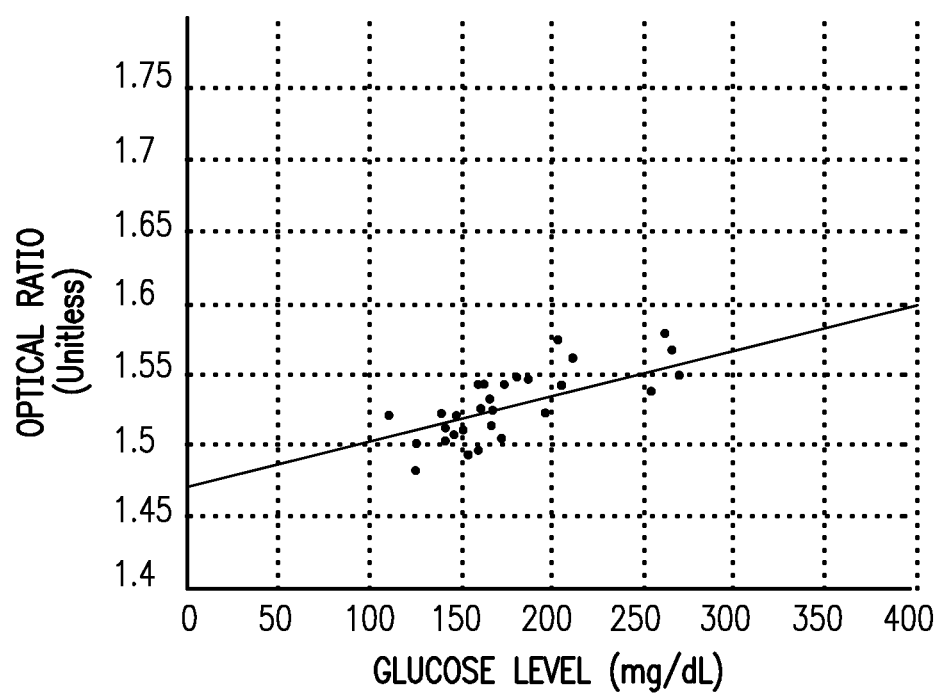

To demonstrate efficacy, FIGS. 25A-C show the effects of drift correction on the signal. When drift is not present, the optical ratio is known to have an almost linear correlation to glucose changes. However, the presence of drift masks this relationship. This is shown in FIG. 25A, which plots independently-measured glucose samples taken throughout the recording versus the optical ratio observed at the same time. FIGS. 25B and 25C demonstrate that, by applying the drift correction, the linear correlation between glucose and ratio, which was lost because of the presence of drift, is restored. FIG. 25B employs drift correction using moving average to compute ẑ(t), and FIG. 25C employs drift correction using linear regression to compute ẑ(t).

It is noted that, although the above example uses optical ratio, this method is applicable to any other signal that may be contaminated with slow time-varying drift.

Failure Detection

The state of the art in failure detection has been steadily moving towards predictive diagnostics that are designed to proactively identify sensor issues before they affect the glucose reading. The orthogonally redundant system of the present invention implements a three-tiered approach to failure detection, i.e., failure detection solely with the electrochemical electrode, solely with the optical sensor, and then with information from the combined signal.

With the electrochemical sensor, the most sophisticated failure detection uses electrochemical impedance spectroscopy (EIS). EIS offers a quick on-line method to diagnose the sensor and sensor membrane status. An important advantage to EIS is that it can be done during sensor operation, without turning the sensor off or changing the electrode state. EIS is performed by passing a small AC voltage signal at a fixed frequency along with the sensor operating voltage (Vset). The current is measured and the impedance is calculated. This measurement is repeated across a range of frequencies, and the impedance output is then examined to look for specific frequency dependent membrane characteristics.

EIS can identify poorly performing sensors and instances where the electrode has been partially pulled out of the tissue (and therefore is no longer sensing correctly). This is particularly useful as it can be difficult for a patient to know when sensor pull-out occurs when wearing miniaturized components. More importantly, EIS may be used as a predictive diagnostic tool, alerting the system to issues before the sensor signal changes drastically.

Figure 26A:
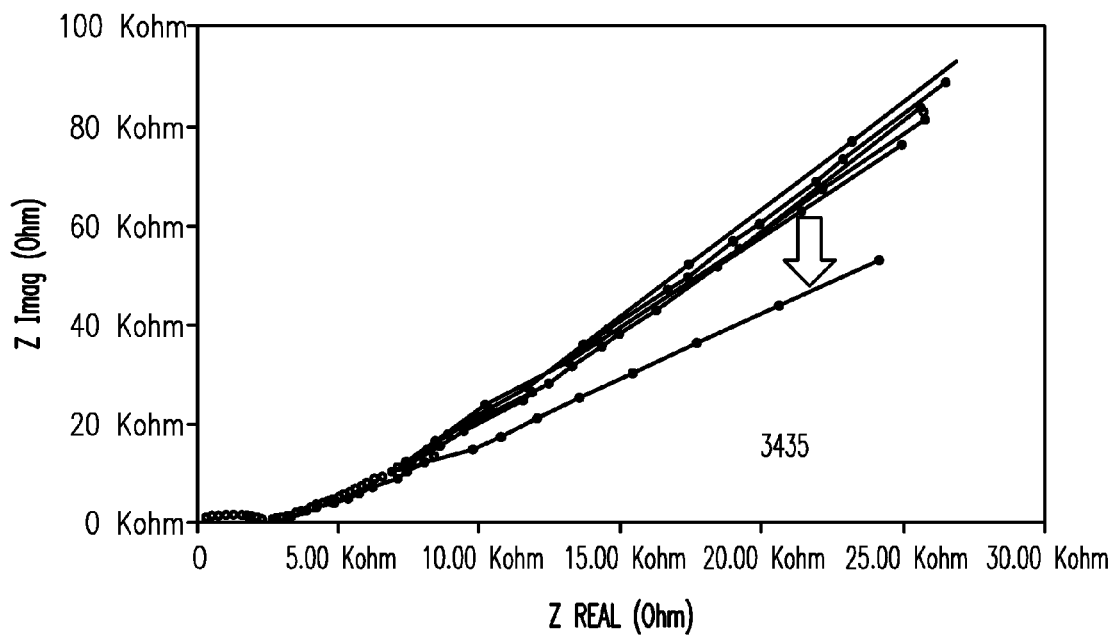
FIGS. 26A and 26B show the use of electrochemical impedance spectroscopy in detecting a drop in low frequency Nyquist slope (a), which predicts a drift in sensor signal (b), in accordance with embodiments of the invention.
Figure 26B:
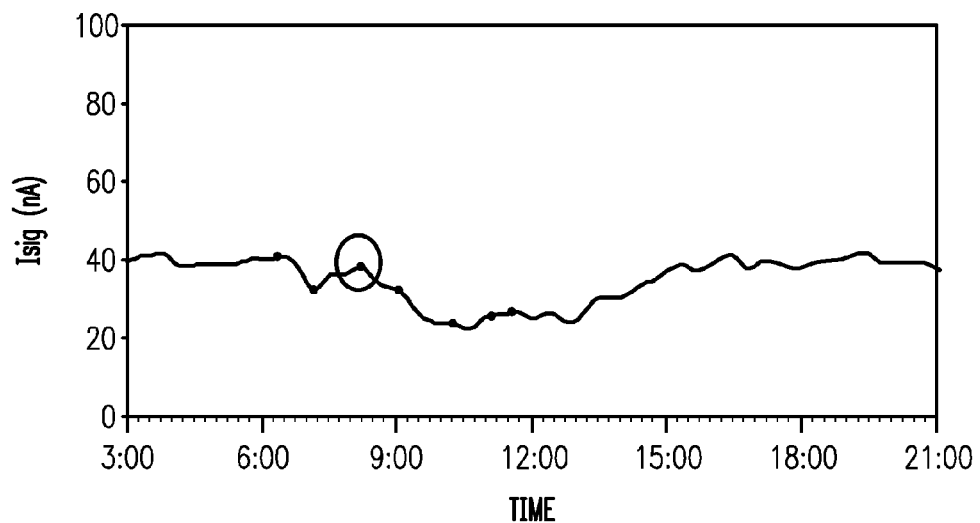
Figure 26C:
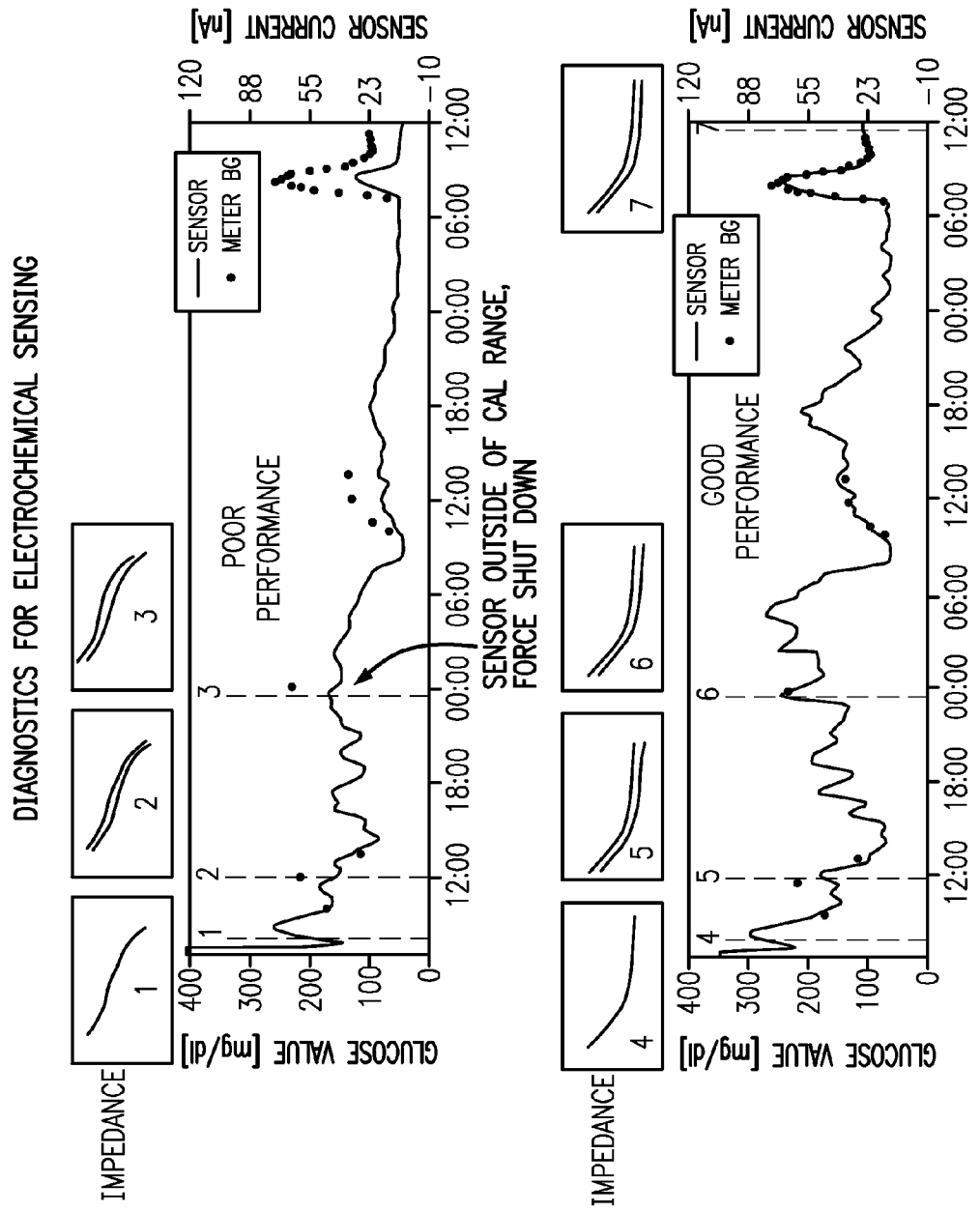
FIG. 26C illustrates predictive diagnostics proactively identifying sensor anomalies for improved reliability in accordance with embodiments of the invention.

In the example shown in FIGS. 26A and 26B, e.g., EIS detects a drop in low frequency Nyquist slope (FIG. 26A), which predicts a drift in sensor signal (sensor anomaly) shown in FIG. 26B. In FIG. 26C, electrochemical sensors are periodically interrogated and analyzed using EIS, and the response is used to proactively identify potential faults or failures, such that the sensor may be recalibrated or shut down before it results in inaccurate glucose measurements. In short, such predictive diagnosis provides the system the opportunity to mitigate the issue through suspended data or calibration request, thereby minimizing the effect(s) on the patient.

Other methods—not involving EIS measurements—for detecting signal anomalies include short periods where the calculated glucose would not be correct, periods where the signal needs stronger filtering, or instances where the sensor's glucose sensitivity has changed (in this case, require a new calibration).

For the optical sensors, the glucose value is calculated from the ratio between the assay signal and the reference signal, as detailed previously. These two signals are independently interrogated and are used to detect failures during use. Both the reference and the assay signal must be within a certain interval (dynamic range), and if outside these intervals, the sensor's performance is not to be trusted. Additionally, if the rate of change exhibited by either the reference or the assay signal is outside the given limits, then this behavior will cause a failure alarm. An example is detecting a misalignment between the reader and the sensor. This will cause both signals to drop to a very low value in a very short period of time and hence cause an alarm based on the signal gradient control function.

The orthogonally redundant system allows comparison of signals. Based on the signal characteristics of each sensor, a reliability index is created for each signal. Comparing the reliability index of each sensor and the signals themselves allows confirmation of suspected faults, or provides assurance for the algorithm that both signals are accurate. For situations when the reliability of the combined signal is under a threshold, a finger-stick confirmation may be necessary. In other regions, the system could give a range of values, such as an expected minimum glucose value to be used for blousing purposes. Micro-environmental aspects, such as drugs or temperature changes, have the potential to influence the system, but the optical sensor does not necessarily respond in the same way as the electrochemical sensor. For example, electro-active species can cause an increased current in the electrochemical sensor, but the optical sensor is not affected the same way or possibly unaffected due to this.

Failure detection in the system of the instant invention is quite robust, as a multi-sensor system has an added benefit of being able to confirm failures. Orthogonally redundant sensors increase this benefit, since the optical sensor and electrochemical sensor have different failure modes and different responses to interfering compounds.

Returning to the electrochemical sensor, it is often challenging to detect certain failure modes of this sensor due to the lack of reference information, as well as the serious consequences of false positive (failure) detection, i.e., incorrectly disregarding real hypoglycemic or hyperglycemic events. One such failure mode that is common to electrochemical sensors and has a relatively large impact on sensor accuracy is sensitivity loss—both temporary and permanent. In this regard, the independent confirmation that is available via the optical sensor of the inventive orthogonally redundant system provides an opportunity for various algorithms to include failure detection logic with respect to the electrochemical sensor. Sensitivity-loss analysis and noise detection may be used in implementing such failure detection logic.

In-Line Sensitivity Loss Analysis

It is noted that, within the context of sensitivity loss analysis, temporary sensitivity loss events may be defined as those events that are recovered, while permanent sensitivity loss events may be defined as those that are non-recoverable. In embodiments of the invention, (electrochemical) sensor failure detection through sensitivity loss analysis may be implemented by separating each sensitivity loss event into three stages: downhill, trough, and uphill, with the third stage (uphill) being optional.

Figure 27:
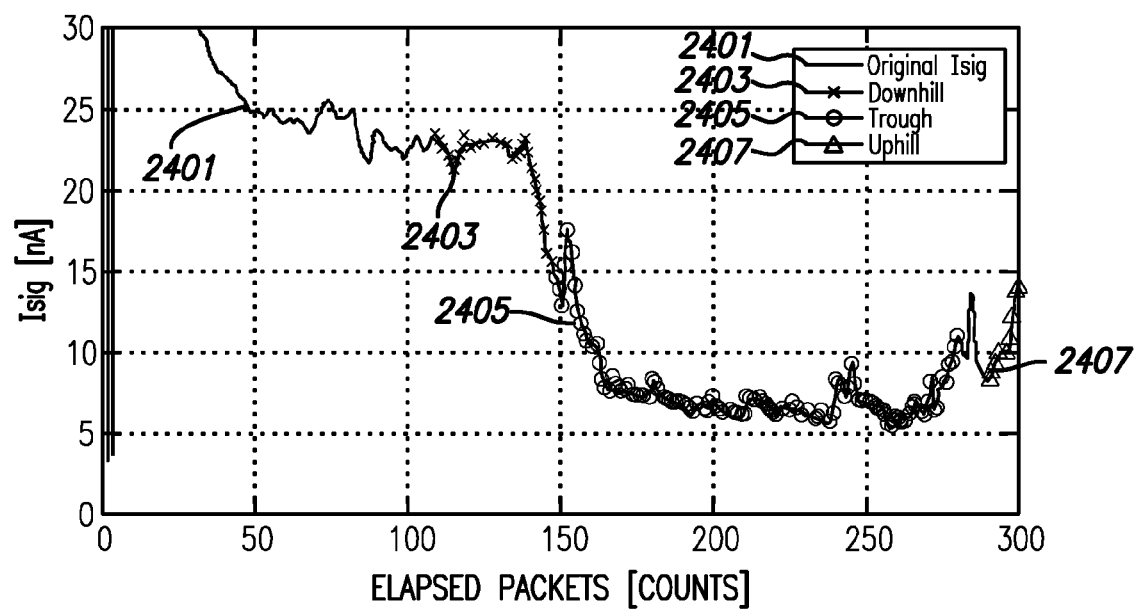
FIG. 27 shows different stages of in-line sensitivity loss detection by visual inspection in accordance with embodiments of the invention.

As shown in FIG. 27 by way of illustration, the downhill stage 2403 may generally be defined as a period of time during which the signal (Isig) 2401 from the electrochemical sensor tends to be low, and carries a high negative rate of change. The downhill stage is followed by the trough stage 2405, which includes a period of time after the sensor has remained in the downhill stage for a given amount of time, thereby confirming that sensitivity loss has occurred. Depending on the specific sensor and environment, the sensor may stay in the trough stage 2405 anywhere from several minutes to several hours. The last stage, uphill 2407, generally covers a period of time in which the sensor signal shows a clear upwards trend and eventually passes beyond a (predetermined) threshold. As noted previously, in embodiments of the invention, the uphill stage may be an optional part of the failure-detection logic.

Figure 28:
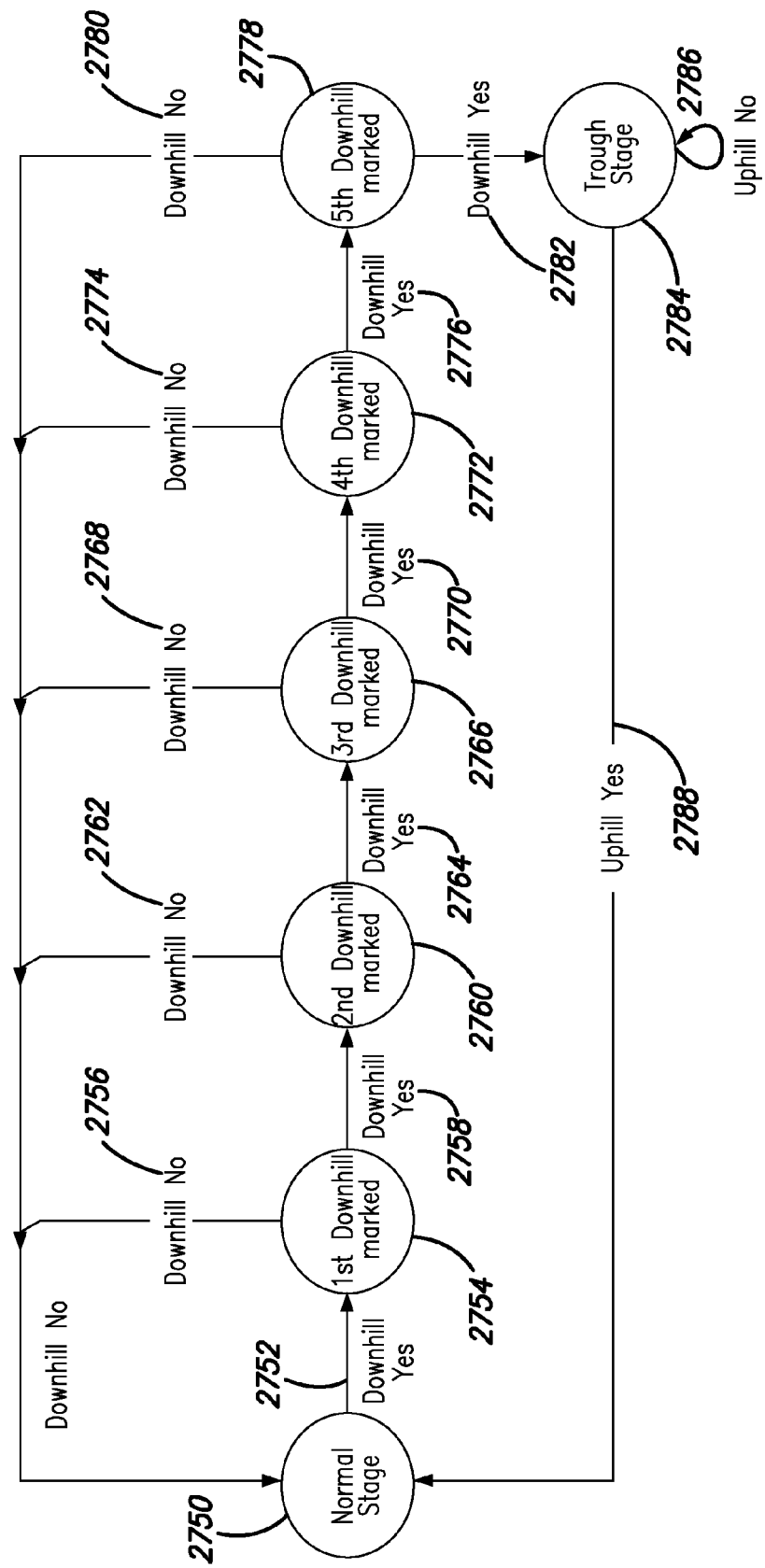
FIG. 28 shows a sensitivity loss detection flowchart in accordance with an embodiment of the invention.

FIG. 28 shows a flow diagram for failure detection based on the above-described logic. Specifically, a sensor signal starts at the normal stage 2750, and then is continuously (or, in embodiments, periodically) monitored to determine whether it remains in the normal stage, or goes downhill (2752). If the signal is going downhill, then, after a predetermined period of time, the (data) packet is marked as having reached a first downhill point 2754. The signal then continues to be monitored such that, if it is no longer going downhill 2756, the packet (and, therefore, the sensor) is determined to have returned to the normal stage 2750. If, on the other hand, the signal is determined to still be going downhill (2758), then, after a predetermined period of time, the (data) packet is marked as having reached a second downhill point 2760.

As shown in FIG. 28, the same logic continues, with lines 2762, 2768, 2774, and 2780 leading back to the normal stage 2750, and each of the lines 2764, 2770, and 2776 leading to a next successive downhill marker. In this example, a determination is made that, if, after the $5^{th}$ marker 2778, the signal is still going downhill (2782), then the signal will be considered to have reached the trough stage 2784. Once at this stage, the monitoring continues, this time checking continuously (or, in embodiments, periodically) to determine whether the signal has started an uphill trend. As long as an uphill trend is not detected (2786), the signal is assumed to remain in the trough 2784. However, once an uphill trend is detected (2788), the signal is monitored for a predetermined period of time or interval, such that, at the end of the interval, if the signal is still trending uphill, it (and, therefore, the sensor) is determined to have returned to the normal stage 2750.

It is noted that, in an embodiment of the invention, once the signal is marked with the first downhill marker 2754, the associated packet is discarded, and continues to remain unused until an uphill trend is detected. In addition, the number of downhill markers to reach the trough stage, as well as the signal monitoring intervals, may be customized as required by, e.g., a specific sensor or a particular application. Moreover, downhill and uphill detection may be based, e.g., on an Isig threshold, or a combination of an Isig threshold and an Isig rate-of-chance threshold. Thus, in embodiments of the invention, and with reference to FIG. 27, the sensor signal may be considered to be trending downhill if the Isig (current) goes below, or is less than, a lower threshold. In other embodiments, the sensor signal may be considered to be trending downhill if the Isig is less than a lower threshold, plus about 10 nA, and the Isig rate of change is less than, or equal to, about −0.1 nA/min. Similarly, in embodiments of the invention, the sensor signal may be considered to be trending uphill once the Isig exceeds a threshold (current), plus about 5 nA.

The above thresholds and offsets are based on empirical data for the electrochemical sensor of the orthogonally redundant sensor system. Specifically, for the ORS sensor, it has been observed that Isig packets below about 10-15 nA tend to display little to no sensitivity and, as such, may not be useful for glucose tracking purposes. As a result, the threshold may vary from 10 nA to 15 nA, depending on the sensor type, as well as the tradeoff between percentage of sensor packet to display and sensor accuracy.

The above-mentioned (5 nA and 10 nA) offsets may also be tailored to specific sensor performance. Examples, in this regard, include: (a) The distribution of all Isig values and cut off at the lowest 2-5% Isig values; (b) Average Isig values when system accuracy indicator (Mean Absolute Relative Difference) MARD exceeds a certain percentage; (c) Set from the combination of the sensor's historical data including Isig range, accuracy, and sensor life time; (d) Set from the user's historical data; and (e) Set from the system's historical data.

Sensor Dip Detection

Figure 29:
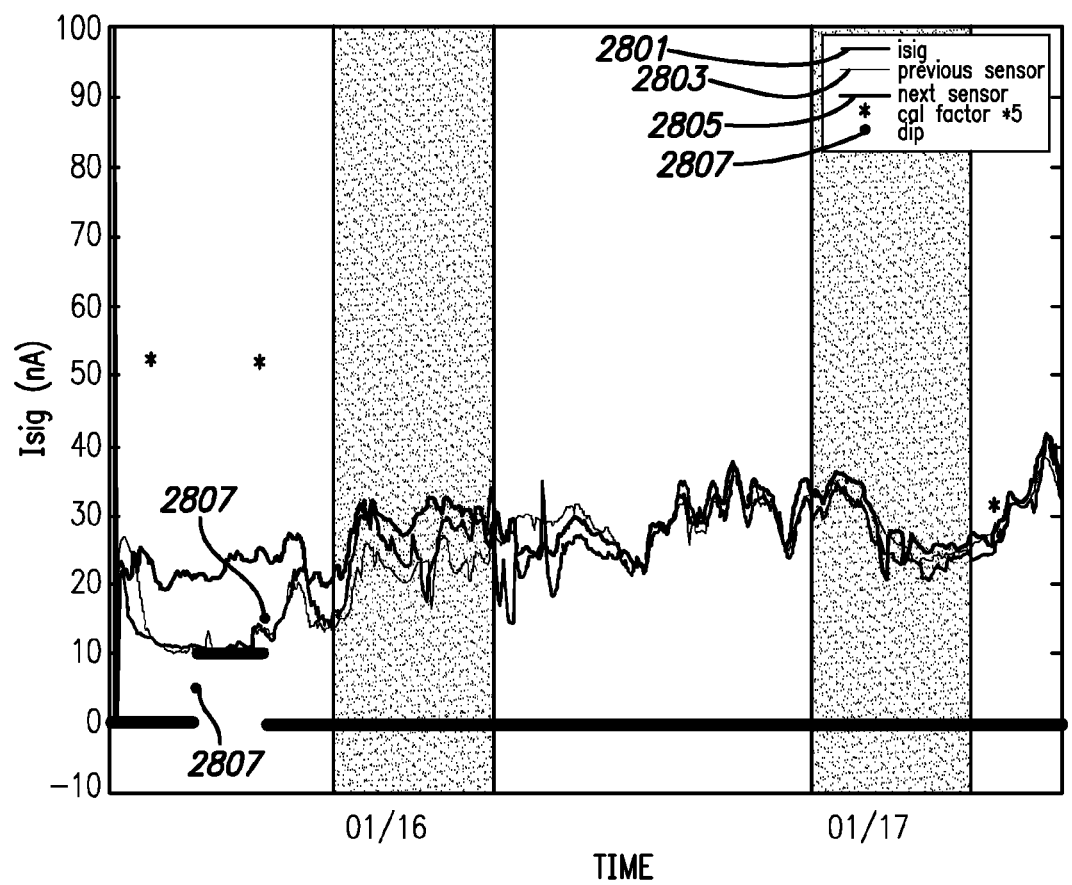
FIG. 29 shows an example of temporary sensitivity loss, or dip, detection using a combination of an electrochemical sensor output (Isig) and the variance of the rate of change of the Isig, in accordance with an embodiment of the invention.

Temporary sensitivity loss—i.e., a sensor "dip"—can also be detected using a combination of the Isig and variance of the rate of change (ROC) of the Isig. In general, this method may be used advantageously when the Isig buffer size is equal to, or larger than, 2 hours. In one embodiment, therefore, the logic proceeds by first creating an Isig buffer of two hours. Next, the mean value and variance of the ROC of the buffer are calculated. Then, every time the mean value is below a first threshold, and the ratio of the ROC variance between the current buffer and the buffer 2 hours ago is below a second threshold, a dip is considered to have started. The dip is considered to end when the mean value of the Isig buffer rises to an upper threshold. This is shown illustratively in FIG. 29, where the "previous sensor" 2803 and the "next sensor" 2805 are companion sensors on the same subject, and the dip starts when the dip indicator 2807 is equal to 5 (nA) and ends when the dip indicator 2807 is at 15 (nA).

Noise Detection for Electrochemical Sensor

A noise metric calculation, similar to that described for the optical sensor and in connection with FIG. 22, may also be used for the raw Isig of the electrochemical sensor, with a different input and scaling factor. Specifically, for echem noise calculation, both Isig (i.e., the signal) and SG (i.e., the sensor glucose value) can be used as inputs. In either case, the Isig and/or the SG must be scaled. In an embodiment of the invention, the scaling factor may be empirically determined to be 9. In addition, when the Isig is being used, the absolute second derivative results also need to be multiplied by the current Cal Factor before scaling. A threshold value can then be calculated based on the distribution of the noise value to determine if the packet can be considered as noisy. In embodiments of the invention, a typical threshold for noise detection can be, e.g., between 3 and 4. The threshold may also be determined based on empirical data, user specific data, and sensor specific data.

Figure 30A:
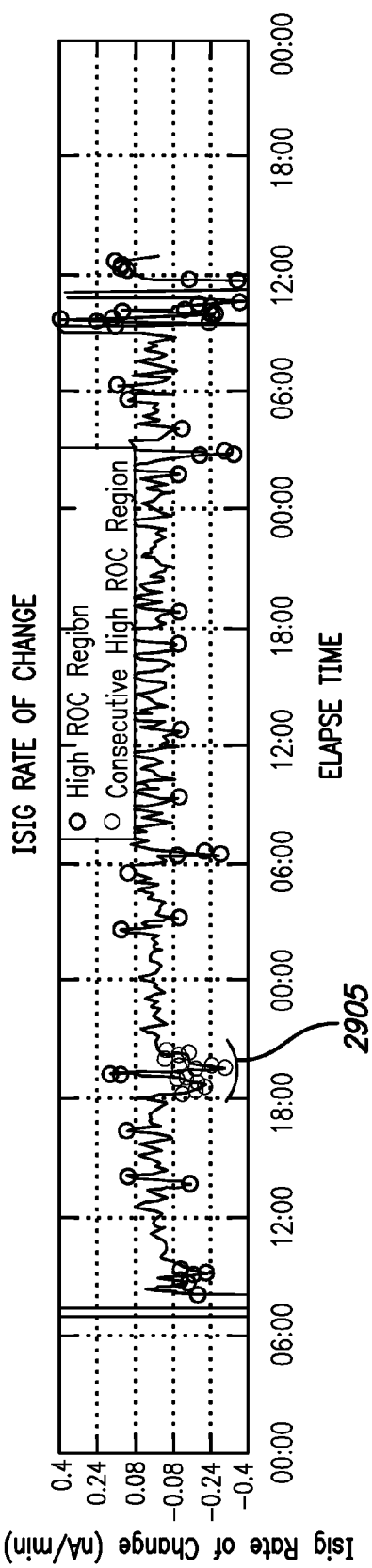
Figure 30B:
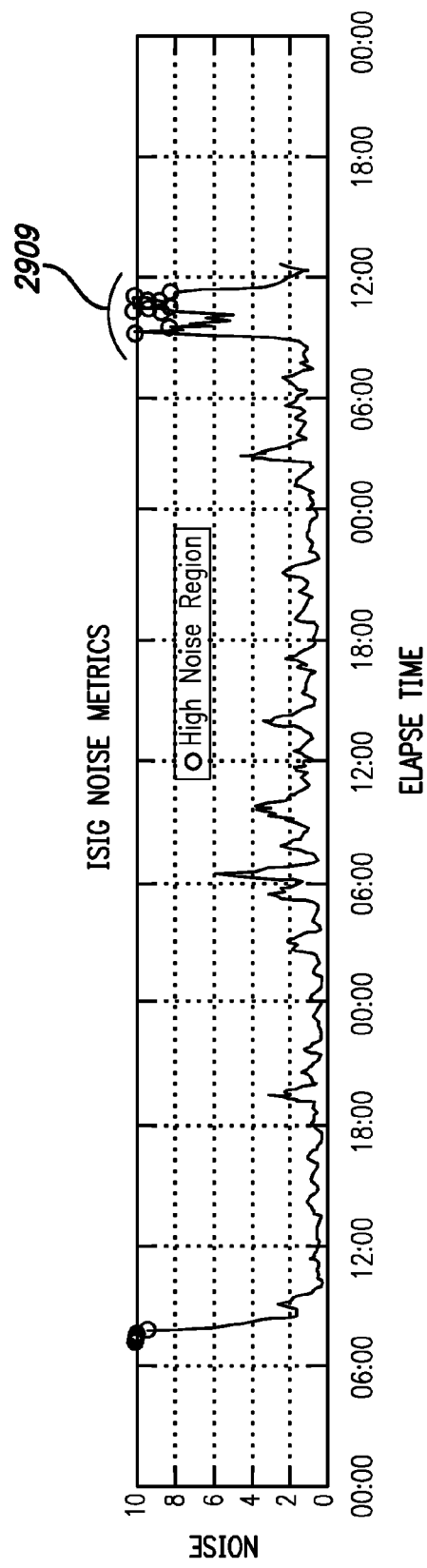

FIGS. 30A-30D show failure mode detection results, wherein a temporary sensitivity loss is present between 19:00 pm (2901) and 8:00 am (2903), starting towards the end of the first day. The sensitivity loss event comprises two periods: (1) a consecutive high-ROC period, as shown in FIG. 30A (2905); and (2) a low-Isig period, shown in FIG. 30C (2907). In addition, a noisy period is detected towards the end of the sensor's life, as shown in FIG. 30B (2909).

In contrast to FIGS. 30A-30D, FIGS. 31A and 31B show a permanent sensitivity loss event that, in this example, started at about 14:00 pm of the first day, towards the end of the sensor's life. This is shown at 3001 on the Isig profile diagram of FIG. 31A. FIG. 31B shows the detection results using the algorithm discussed herein. In FIG. 31B, the sensitivity loss event is detected at about 16:00 pm (3003), about 2 hours after the event started, with all succeeding packets being identified as part of the sensitivity loss.

Calibration

As has been noted, the orthogonally redundant system includes several features which result in a reduction in calibration frequency using an "on-demand" protocol to limit calibrations to 2-4/week (down from, e.g., 2 calibrations per day). These features include: (1) Sensor accuracy/durability improvements of electrochemical glucose sensors; (2) physiological model-based calibration algorithm; (3) redundant and orthogonal sensing technology which allows for internal self-calibration after individual components have reached stable-state; and (4) "Smart" diagnostics which allow for transition from timing-based to need-based calibration requests.

Historically, CGM systems have relied on "minimum scheduled sample time" for sensor calibration as a way to adjust for inaccuracies characteristic to the sensing component. Thus, existing calibration algorithms rely on a minimum of 1 calibration point for every 12 hours of sensor operation (ES9199, ES9573, ES9966). Based on this standard, the DexCom® SEVEN® PLUS product, e.g., requires 2 at startup and every 12 hours afterward, and the FreeStyle Navigator® requires calibration at 10, 12, 24, and 72 hours post insertion.

As sensing technology has improved, sampling requirements have decreased, but at the expense of system accuracy. In contrast, the inventive orthogonally redundant sensing system allows for a significant reduction in calibration frequency compared to existing sensor technologies, while maintaining expectations of sensor accuracy throughout its lifetime.

Figure 32:
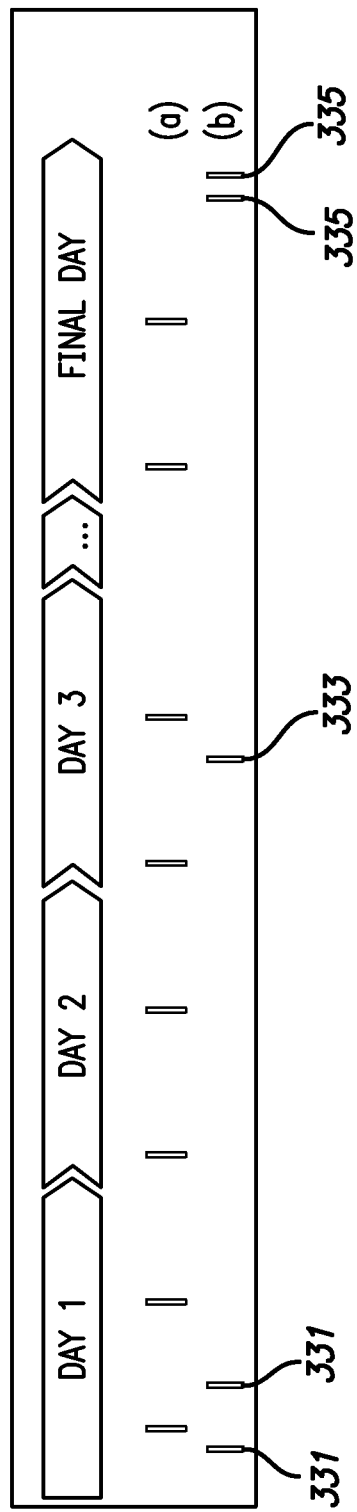
FIG. 32 shows a comparison of calibrations frequency vs. time between existing systems (a) and embodiments of the present invention (b).

The implementation of a diagnostic algorithm with the ability to verify sensor performance allows for a shift from "in-time" to "on-demand" calibration protocols. In this regard, FIG. 32(*a*) shows a simulated calibration scheme based on current generation single-sensor technology, and FIG. 32(*b*) shows an alternative made possible by measurement redundancy of the type disclosed herein. Pursuant to the latter calibration scheme, initial calibration(s) 331 are still necessary; however, the twice-daily (time-scheduled) calibration requests are no longer required as part of the calibration algorithm. Instead, a combination of infrequent scheduled requests 333 (i.e., once every 72 hours) and on-demand requests 335 ensures that sensor calibration will only be required when the system identifies a need to confirm sensor health. As system performance using this scheme relies on accurate and frequent diagnostic information, failure detection and other advanced algorithms will be critical to reducing the number of calibrations requested on a consistent basis.

It is noted that some current prototype electrochemical sensors in development have internal targets of 13% MARD with signal drift less than 10%/day. Likewise, a calibration algorithm based on a two-compartmental fluid-flow model of glucose transfer within the body will reduce the blood-to-subcutaneous concentration gradient effect (delay) as well as eliminate artifacts from the signal that are deemed to be physiologically unlikely.

Figure 33:
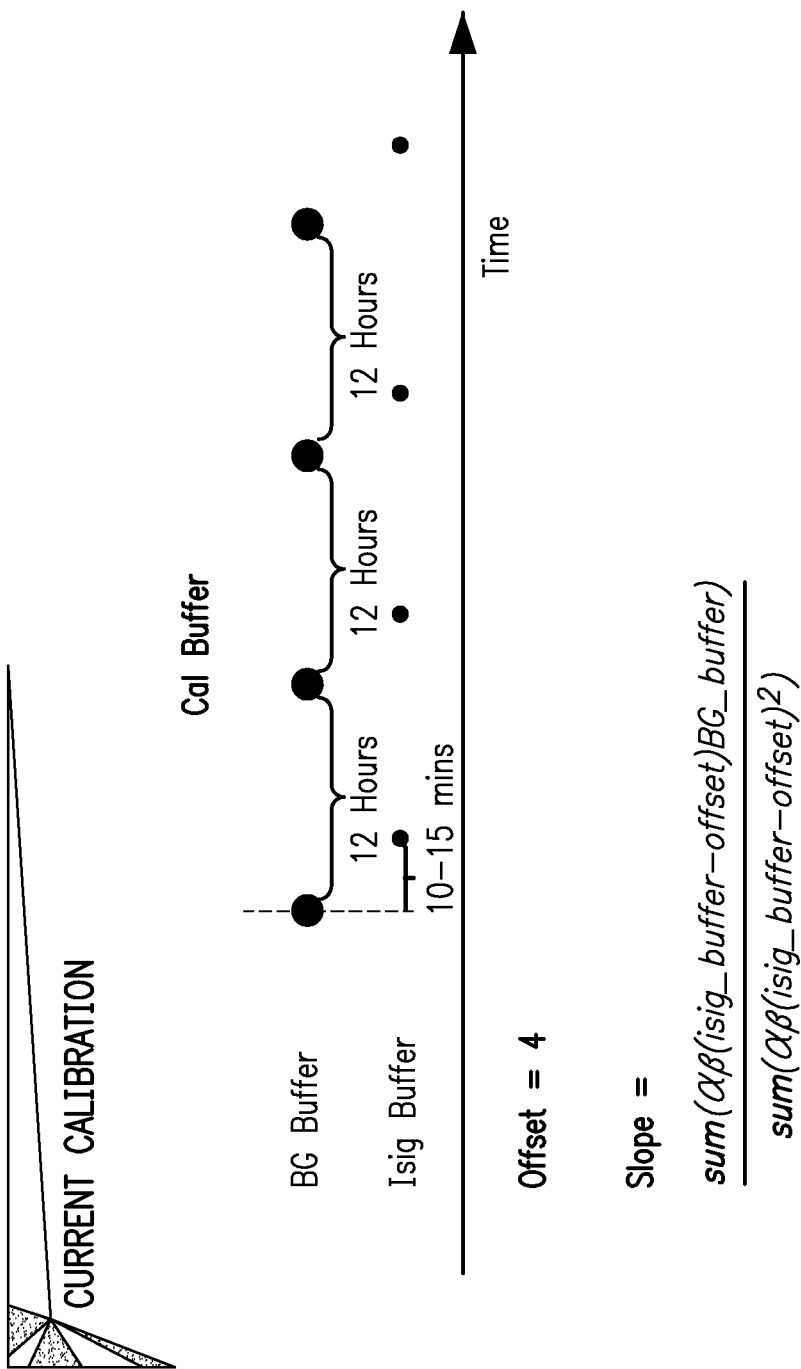
FIG. 33 shows details of a fixed-offset calibration method in accordance with embodiments of the invention.

In embodiments of the invention, when the orthogonally redundant glucose sensor is stable, and the Isig/pair correlation is high, a dynamic calibration method may be used. However, when the sensor is unsteady, a fixed-offset method may be used. FIG. 33 shows details of the fixed-offset calibration method. It is noted that the fixed-offset calibration method may be used for calibrating both the optical sensor and the echem sensor.

Some details of the dynamic regression calibration method are shown in FIG. 34, where, instead of minimizing the residual sum of squares, one minimizes the weighted sum of squares. It is noted that, while the dynamic regression calibration method may be used for calibrating both the optical sensor and the echem sensor, the parameters shown in FIG. 34 are specifically for echem sensors.

Figure 35A:
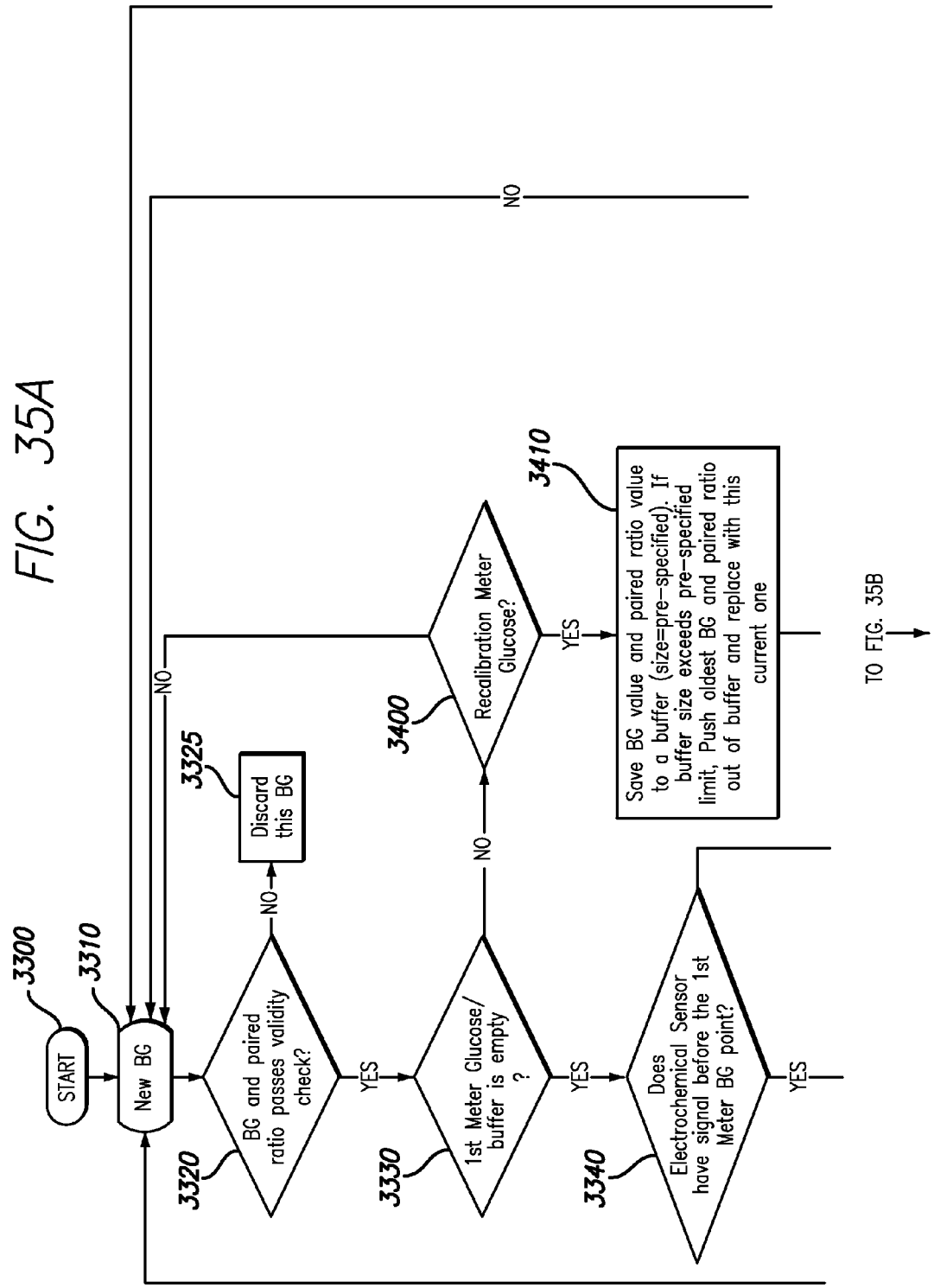
FIGS. 35A and 35B show a flowchart for a dynamic regression algorithm for optical sensor calibration in accordance with an embodiment of the invention.
Figure 35B:
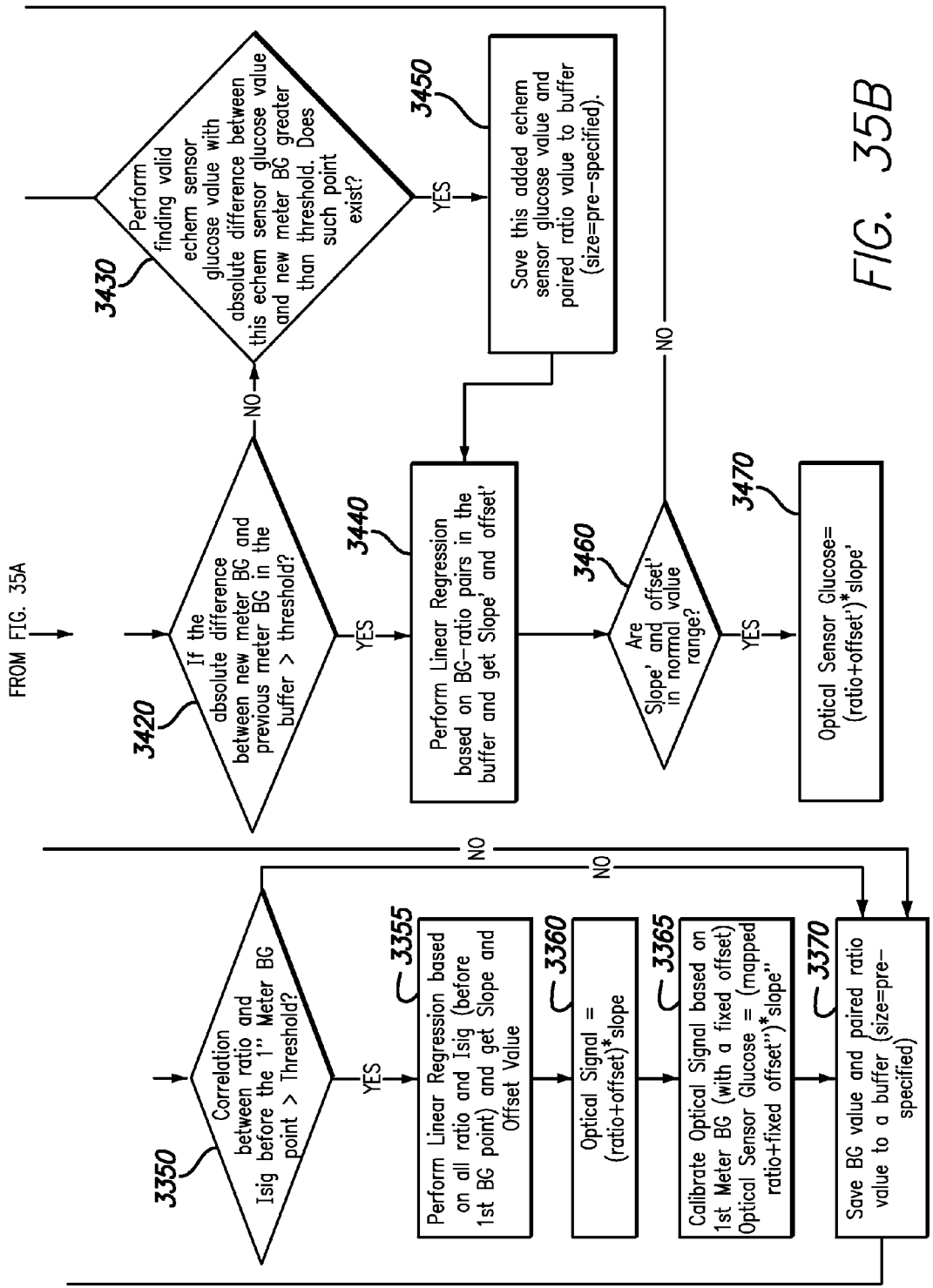

For the optical sensor, dynamic regression is based on linear regression with meter glucose values (BG) and the paired optical signal ratio inside a buffer. The paired ratio is the ratio (of the optical assay signal to the optical reference signal) that is recorded within a certain specified time of the timestamp of the BG. The BG and paired ratio points are put inside a buffer after certain conditions are met. Specifically, a dynamic regression algorithm for optical sensor calibration in accordance with an embodiment of the invention may be described with reference to the flowchart of FIGS. 35A and 35B.

The algorithm starts at block 3300, where it checks to determine whether both the optical sensor and the electrochemical sensor are not in the initialization period, followed by a determination as to whether any meter glucose value (BG)—i.e., meter glucose value of a series of one or more values to be obtained during the process—is available for calibration 3310. For the former determination, the optical signal ratio's rate of change at start-up is checked, and the optical signal is considered past the initialization period when the aforementioned rate of change is below a certain threshold. In embodiments of the invention, the threshold may be determined based on in vivo and/or in vitro data.

Figure 36:
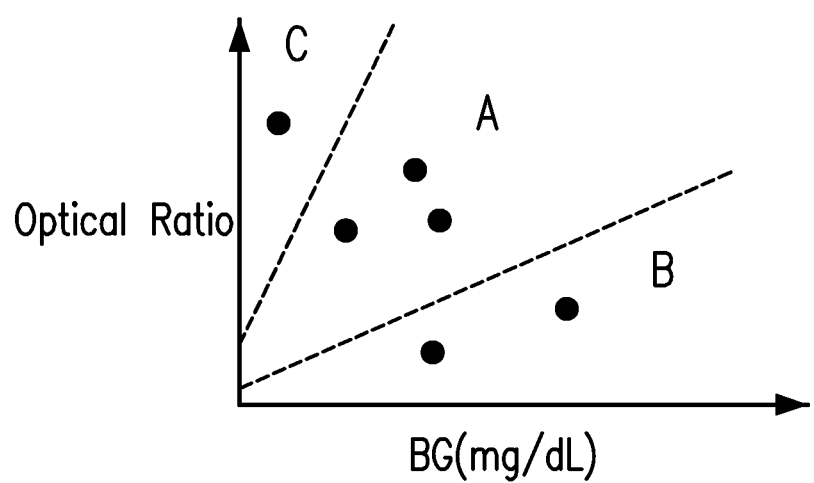
FIG. 36 shows an illustrative graph of blood glucose (BG) values vs. Optical Ratio values that may be used to perform validity checks on BG-Optical Ratio pairs in accordance with an embodiment of the invention.

Whenever there is new input meter BG for calibration, the algorithm performs a validity check on the BG and its paired ratio (3320) to ensure that linear regression using the BG and the paired ratio inside the buffer would generate reliable values for calibration. In embodiments of the invention, the validity check may be performed by determining whether the BG and its paired ratio fall within the specified region of a BG and ratio validity relationship chart. In this regard, FIG. 36 shows an illustrative graph of BG vs. Optical Ratio values, wherein points inside region A would be accepted, while points inside regions B and C would be rejected and not be put into the buffer (3325).

If there is a BG, and if it is the first BG point (3330)—of the one or more BG points to be obtained—the algorithm will attempt to "map" the optical sensor signal to the electrochemical sensor signal. Performing this mapping for this beginning period enables the dynamic regression algorithm to start generating calibrated sensor glucose values with a single BG point. The electrochemical sensor signals after the initialization period and before the first calibration BG point will be used for mapping (3340). Next, a correlation value is calculated by performing linear fitting of the optical ratio to Isig, and calculating the coefficient of determination between the optical signal and Isig. Based on the correlation calculation of the (optical) ratio and Isig, both of which are sensor signals before the first BG, the algorithm can determine if the optical sensor signal and Isig match well with each other, i.e., whether the correlation coefficient is greater than a lower threshold (3350). The threshold may be determined using data from in vitro and/or in vivo studies.

If the optical ratio and Isig do not correlate well, then, the BG value and the paired ratio value are saved to a first-in-first-out (FIFO) buffer of a pre-determined, or specified, size (3370). However, if the two signals correlate well, then a linear regression calculation is performed on the ratio and Isig (before the first BG point) so as to obtain values for the slope and offset (3355). With the latter values, at step 3360, a mapped optical sensor signal value is obtained by using the relation:

$$(\text{Mapped}) \text{optical ratio} = (\text{ratio} + \text{offset}) * (\text{slope}) \quad \text{Eqn. (8)}$$

Next, the mapped optical sensor signal is calibrated based on the first BG point with a fixed offset (3365), wherein:

$$\text{Optical sensor glucose value} = (\text{mapped optical ratio} + \text{fixed offset''}) * (\text{slope''}) \quad \text{Eqn. (9)}$$

With a fixed offset, the slope can be obtained with a single BG and ratio pair. The fixed offset may be selected based on in vivo and/or in vitro data. At block 3370, the first BG and its paired ratio value are saved to a FIFO buffer (with fixed size). In embodiments of the invention, the buffer size may be determined by using data from in vivo studies. The algorithm then loops back to block 3310.

At node 3400, when there is a new recalibration BG point, the new recalibration BG and its paired ratio undergo the validity check described previously in connection with FIG. 36. If the buffer size is below a specified limit, the new BG and its paired ratio are added to the buffer. If, on the other hand, the buffer size exceeds the limit, then the oldest pair of BG and ratio inside the buffer are pushed out of the buffer and the new recalibration BG and its corresponding paired ratio are added into the buffer (3410). Next, at 3420, a determination is made as to whether the absolute difference between the new meter BG and the previous meter BG (in the buffer) is greater than a predefined threshold (i.e., a "calibration BG difference" threshold). If it is determined that the absolute difference between the new meter BG and the previous meter BG is greater than the calibration BG difference threshold, then the BG and paired ratio are saved to the buffer, and linear regression is performed based on all BG-ratio pairs inside the buffer to obtain slope' and offset' (3440). A check is then performed to determine whether the calculated slope' and offset' values are in a normal value range which, in embodiments of the invention, may be determined by in vitro and/or in vivo data (3460).

If the slope' and offset' values are both in the normal value range, then an optical sensor glucose value is calculated as (3470):

$$\text{Optical sensor glucose value} = (\text{ratio} + \text{offset'}) * \text{slope'} \quad \text{Eqn. (10)}$$

At node 3420, if it is determined that the absolute difference between the new recalibration BG point and the previous recalibration BG is less than the pre-defined calibration BG difference threshold, then the algorithm proceeds by finding an echem sensor glucose value to provide a calibration glucose point. In this regard, it is noted that the addition of echem sensor glucose values can provide calibration glucose points that meet the calibration BG difference threshold and improve the robustness of the dynamic regression. Thus, if the absolute difference between the new BG and the previous BG is less than the pre-defined threshold (calibration BG difference threshold), then the algorithm looks for a valid echem sensor glucose value and uses that value as an additional BG point in the buffer (3430). It is noted that, if no such echem sensor glucose value exists, then the algorithm loops back to block 3310.

The echem sensor value must be within a certain time limit of the recalibration BG point's timestamp, and the absolute difference between that echem sensor glucose and the new recalibration meter BG must be greater than the calibration BG difference threshold. In addition, the echem sensor glucose value must be valid, such that it passes the BG-paired ratio validity check described hereinabove in connection with FIG. 36. The echem glucose values must also be in the functional region of the echem sensor, with the MARD in that region being below a defined limit. If such echem sensor glucose value is available, the glucose value and its paired ratio are saved to the buffer (3450), and calibration is carried out as described previously, i.e., by performing linear regression based on all BG-ratio pairs in the buffer, and calculating slope' and offset' (3460). If the slope' and offset' are both in the normal value range, then sensor glucose values will be calculated based on Equation 10 (3470).

In embodiments of the invention, the above-described addition of echem sensor glucose values can be performed whenever there is a new recalibration BG point, and the absolute difference between that recalibration BG and the previous recalibration BG point does not exceed the calibration BG difference threshold. In this regard, FIG. 37A shows a plot in which some of the calibration BGs do not meet the requirement that the absolute difference between the new recalibration BG and the previous recalibration BG be greater than a predefined calibration BG difference threshold. As such, sensor glucose values cannot be updated using dynamic regression. In FIG. 37B, however, two calibration glucose values 3510, 3520 were obtained from echem sensor glucose values, which enabled dynamic regression to have more points that meet the calibration BG difference threshold for recalibrations.

Sensor Glucose (SG) Fusion

As noted previously in connection with FIG. 16, an overall calibration methodology in accordance with embodiments of the present invention generates two sensor glucose outputs, i.e., two calibrated sensor signals: one SG for the optical sensor, and a second SG for the electrochemical sensor. In embodiments of the invention, a two-sensor SG fusion methodology is therefore used to generate a single SG from the two SGs, with the single SG having an optimum accuracy. In this regard, it is noted that a two-SG fusion methodology, or algorithm, is shown generically at block 2030 of FIG. 16.

Figure 38:
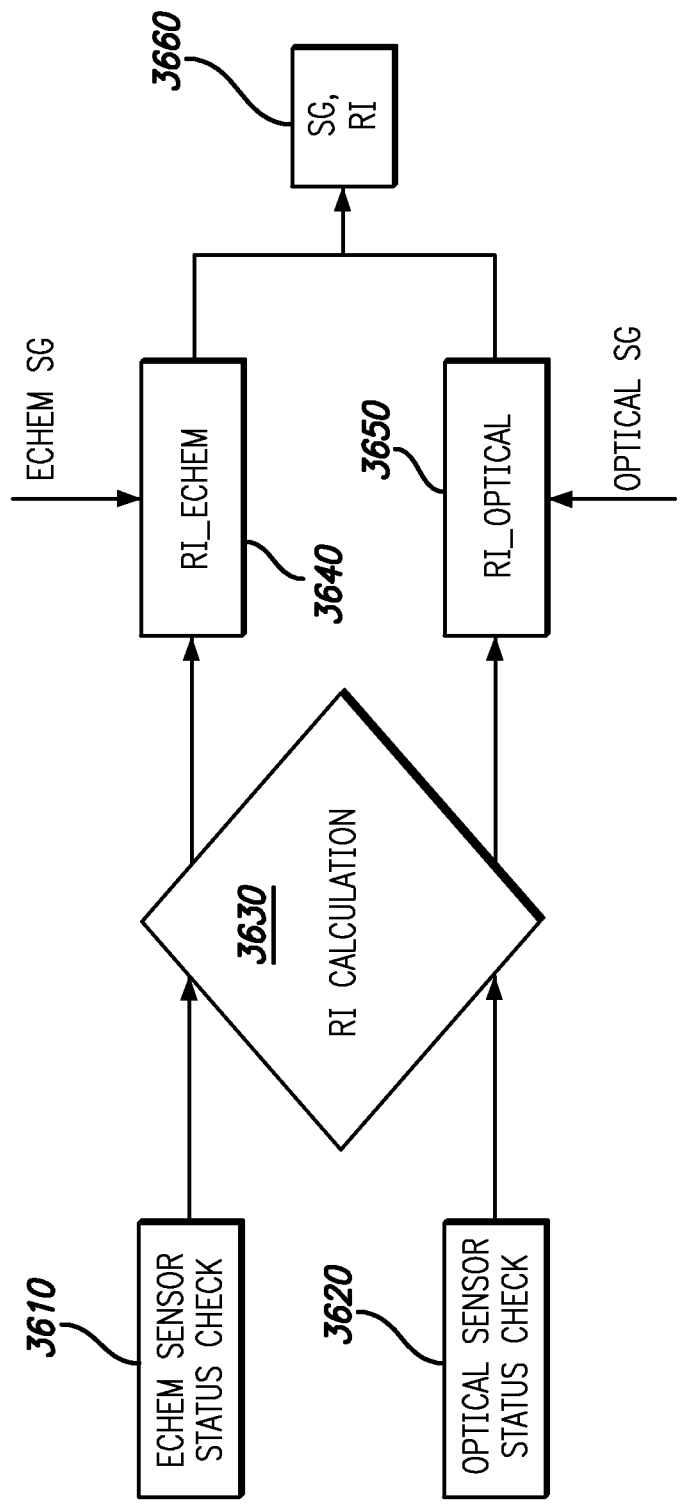
FIG. 38 shows a flowchart for a 2-sensor glucose (SG) fusion algorithm in accordance with embodiments of the invention.

FIG. 38 shows the logic of a two-SG fusion algorithm in accordance with a preferred embodiment of the present invention. As depicted in this figure, for each SG, a sensor status check 3610, 3620 is required to keep track of the reliability of the respective output. The key parameters that may be used to perform a status check for the electrochemical sensor include: (1) echem Isig value; (2) the previous cal ratio, the cal ratio being defined as BG/(Isig-offset); (3) the previous sensor accuracy (MARD); and (4) sensitivity loss/dip flag, as determined by in-line sensitivity loss/dip detection (discussed hereinabove in connection with FIGS. 27-31). For the optical sensor, the key parameters include: (1) optical ratio signal; (2) previous cal ratio, with cal ratio being defined as BG/optical signal; (3) previous sensor accuracy (MARD); and (4) sensitivity loss/dip flag, determined by in-line sensitivity loss/dip detection (discussed hereinabove in connection with FIGS. 27-31).

At 3630, a reliability index (RI) is calculated for the output from each of the electrochemical and optical sensors (3640, 3650). Specifically, in a preferred embodiment, the reliability index for each output is defined as follows:

$$RI_{echem} = RI_{dip} \times RI_{noise} \times RI_{sensitivity\ loss} \times RI_{cal} \times RI_{accuracy} \qquad \text{Eqn. (11)}$$

$$RI_{optical} = RI_{dip} \times RI_{noise} \times RI_{sensitivity\ loss} \times RI_{cal} \times RI_{accuracy} \qquad \text{Eqn. (12)}$$

Wherein $RI_{echem}$ is the reliability index for the output of the electrochemical sensor, $RI_{optical}$ is the reliability index for the output of the optical sensor, and $RI_{dip}$ and $RI_{sensitivity\ loss}$ are determined by the method(s) described previously in connection with FIGS. 27-31. It is noted that, when a sensor dip or sensitivity loss event occurs, $RI_{dip}$ or $RI_{sensitivity\ loss}$ is set to 0. Otherwise, both $RI_{dip}$ and $RI_{sensitivity\ loss}$ are set equal to 1.

In the above equations, $RI_{noise}$ is calculated by first quantifying noise via a noise metric as described hereinabove in connection with FIGS. 22, 23, 30, and 31. Once noise is quantified, $RI_{noise}$ is quantified as follows: (1) If the noise metric is higher than a pre-defined threshold, $RI_{noise}$ is set equal to 0; (2) Otherwise, $RI_{noise}$ is set equal to noise metric/threshold.

Figure 39:
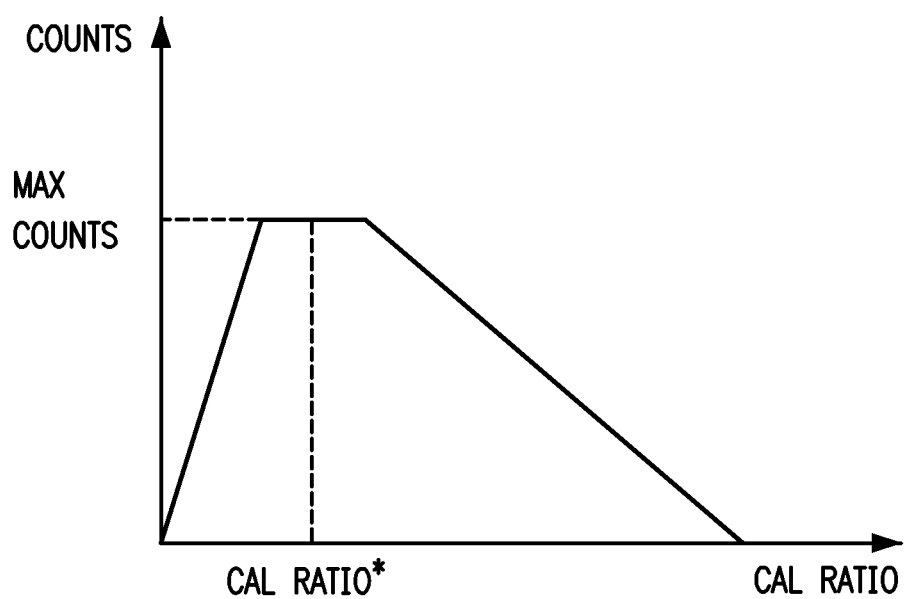
FIG. 39 shows an approximation of a log-normal distribution for Cal Ratio distribution used in calculating a Cal Ratio Reliability Index ($RI_{cal}$) in accordance with embodiments of the invention.

$RI_{cal}$ is determined by cal ratios. In general, cal ratios of both the optical sensor and the electrochemical sensor follow a log-normal distribution. An approximation of a log-normal distribution for the cal ratio distribution is shown illustratively in FIG. 39. With reference to FIG. 39, it is noted that, the closer the current cal ratio is to Cal Ratio*, the more reliable the sensor is. Thus, $RI_{cal}$ may be generated by simply following the shape of the log-normal distribution, with the maximum cal ratio reliability (max $RI_{cal}$)=1 near Cal Ratio*, and the minimum cal ratio reliability (min $RI_{cal}$)=0 when the current cal ratio is far away from Cal Ratio*. It is important to note that, although the cal ratios of the optical and electrochemical sensors follow a log-normal distribution, the value of Cal Ratio* is different for the two SGs.

Finally, $RI_{accuracy}$ is determined by the accuracy of each sensor at the last calibration point, with MARD being calculated as: MARD=abs(SG−BG)/BG. $RI_{accuracy}$ is then calculated by normalizing MARD by: (1) When MARD is higher than MARD_high_thres, setting $RI_{accuracy}$=0; (2) When MARD is lower than MARD_low_thres, setting $RI_{accuracy}$=1; and (3) When MARD is between MARD_low_thres and MARD_high_thres, setting $RI_{accuracy}$= (MARD_high_thres−MARD)/(MARD_high_thres−MARD_low_thres), wherein MARD_high_thres is a (pre-determined) upper threshold for MARD, and MARD_low_thres is a (pre-determined) lower threshold for MARD.

Once the reliability index for each of the optical and the electrochemical sensors has been calculated, the final (i.e., fused) SG is calculated by summing the weighted SG of the electrochemical sensor (i.e., the weighted, calibrated echem signal) and the weighted SG of the optical sensor (i.e., the weighted, calibrated optical sensor signal), as follows:

$$SG\_fusion = sum(Weight \times SG) \qquad \text{Eqn. (13)}$$

where (SG) weight is determined as:

$$Weight = f(RI) \qquad \text{Eqn. (14)}$$

In the above equation, function "f" may be either a linear function or a non-linear function, such as, e.g., an exponential function. Thus, where "f" is a linear function, Weight may be calculated as:

$$Weight_i = \frac{RI_i}{\Sigma RI_i} \qquad \text{Eqn. (15)}$$

On the other hand, where "f" is a non-linear function, $$Weight_i = \frac{RI\_transformed_i}{\Sigma RI\_transformed_i} \qquad \text{Eqn. (16)}$$

where $$RI\_transformed_i = -\frac{1}{\log(RI_i) + const} \qquad \text{Eqn. (17)}$$

and "const" is a constant to ensure that RI_transformed is always positive.

Figure 40A:
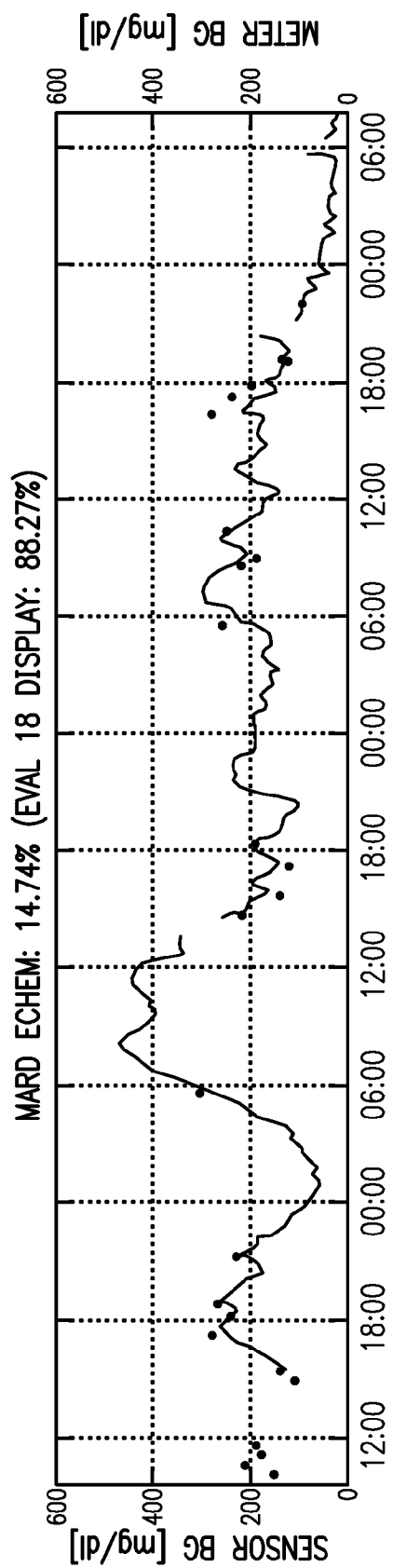
FIGS. 40A-40C illustrate an example of SG fusion and the resulting reduction in MARD in accordance with embodiments of the invention.
Figure 40B:
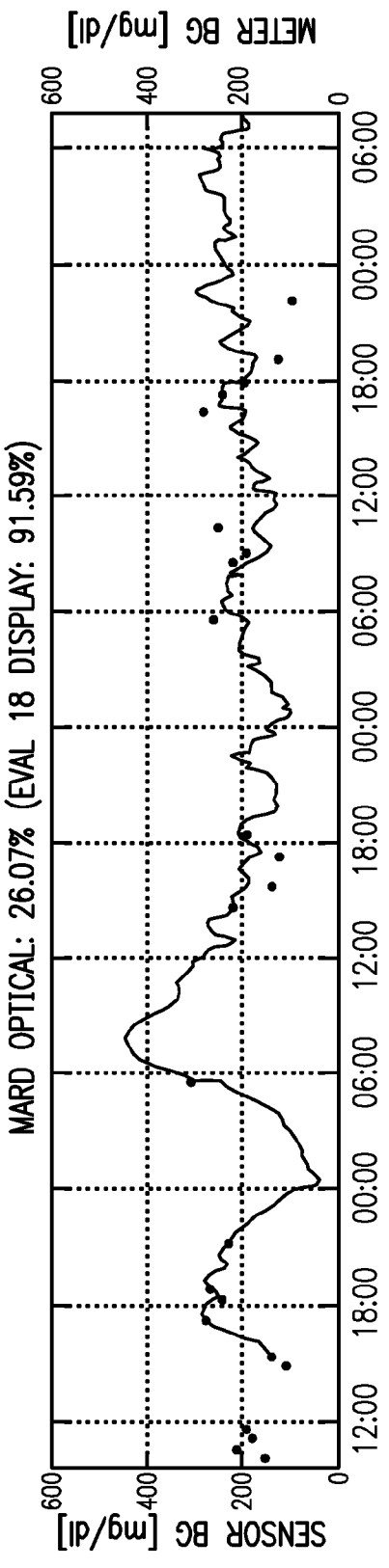
Figure 40C:
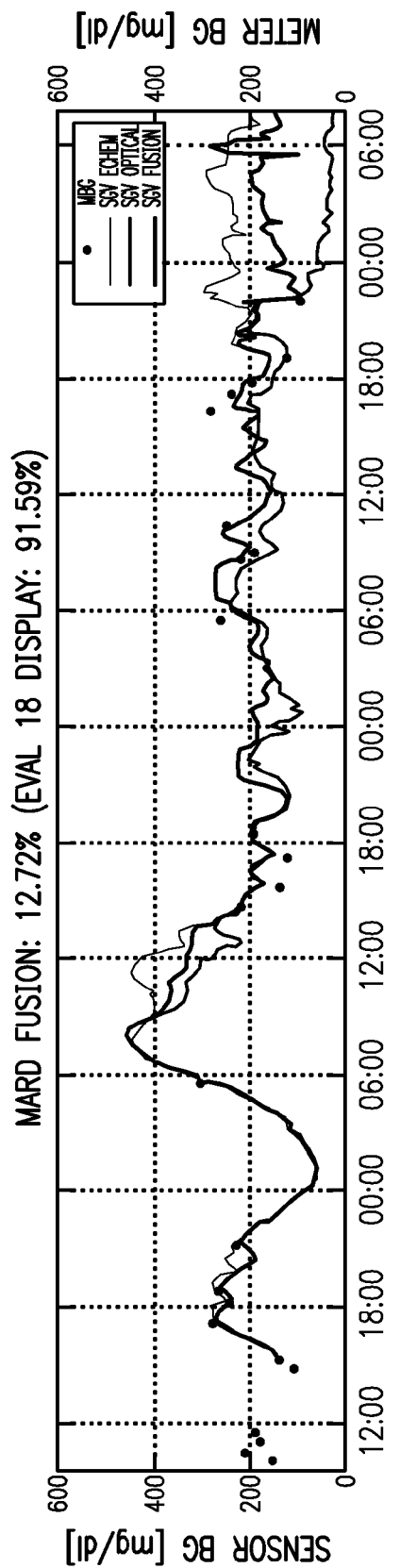

FIGS. 40A-40C illustrate an example of SG fusion. In these figures, the electrochemical sensor loses sensitivity towards the end (FIG. 40A), while the optical sensor appears to be functioning normally (FIG. 40B). The MARD for the electrochemical sensor is 14.74%, and that for the optical sensor is 26.07%. The overall fusion MARD, however, is 12.72% (FIG. 40C), which is a marked improvement over both the electrochemical sensor and the optical sensor.

Duration of Wear

The orthogonally redundant sensor system increases duration of wear and reliability of data through the use of redundancy, fault detection, and advanced algorithms to ensure at least one sensor is providing reliable measurements. In addition, the sensor lifetime is limited to the specified duration of wear to ensure reliability of data.

Duration of wear can be classified in two ways: (1) the overall lifetime of the sensor; and (2) the percent of time during wear that the sensor is displaying accurate data. The sensor lifetime is limited through loss of sensitivity and drift in-vivo that may be caused by environmental influences. The orthogonally redundant sensor system decreases the frequency of early sensor termination through the use of redundancy and dual sensing technologies, ensuring at least one sensor is providing reliable measurements for an increased duration and safeguarding against environmental influences. Additionally, body worn devices must be safeguarded against sensor pull-outs that result in early termination. As such, custom adhesives for both patch and overtape may be implemented for the combination device.

As mentioned previously (see above section on "Accuracy"), failure detection algorithms limit the inaccurate data that is visible to the patient but, as a result, may limit the data to such an extent that the continuous sensing benefits are not realized. Utilizing a redundant sensing system improves the percent of time the sensor displays data because the frequency of anomalies simultaneously in both sensors is significantly less than in a single sensor.

Additionally, sensors may also stay implanted beyond seven days. Sensors implanted beyond the labeled lifetime may be more likely to provide erroneous data. Therefore, to ensure reliability, it is important that the system limit sensor lifetime to the labeled time period. This is accomplished through the system design utilizing embedded firmware timers in the instrumentation coupled with diagnostics methods that can detect whether a sensor has been previously used. By combining embedded timers and intelligent diagnostics, the system ensures that sensors are not used beyond the period of optimal reliability and accuracy.

Form Factors

While combining two sensor systems into a single device requires more instrumentation and battery capacity, miniaturization and integration methods may be used to ensure that the transmitter device 10 is similar in size to other CGM devices.

Device size, form factor, and use model play a significant role in therapy adoption. When placing the device on the body, a larger, simply-shaped device tends to be easier to handle, whereas a smaller, organically-shaped device tends to be more preferable to wear. In preferred embodiments of the invention, a well-balanced design based on the foregoing factors is adopted.

In order to avoid unsightly distortions when the device is worn under clothing, patients generally prefer a larger device footprint over added height. Because the device in accordance with embodiments of the instant invention contains more complex and substantial internal components than other CGMS products currently available, it is understood that the footprint of the assembly is slightly larger than what is currently available. Thus, the device is as slim and sleek as possible, with minimal sacrifice in the way of volumetric efficiency.

Figure 41:
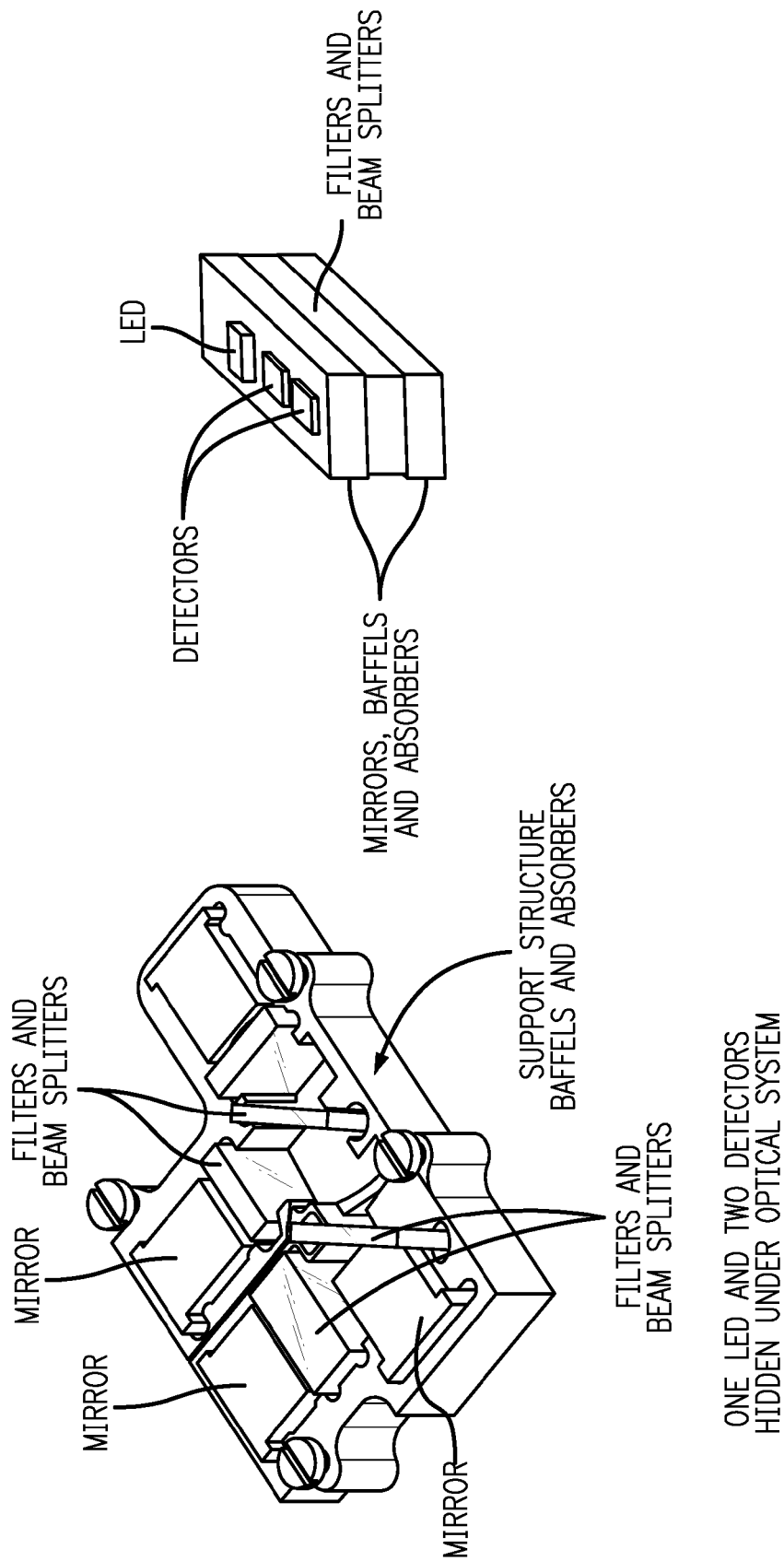
FIG. 41 shows an optical system having discrete components (left), and a stacked planar integrated optical system (right) in accordance with embodiments of the invention.

Wafer-level design and production methods are used in a novel way to minimize the size of the optoelectronic (or optical) interrogating system. A Stacked Planar Integrated Optical System (SPIOS) may be created by fixing one multi-functional filter layer between two injection molded layers of optical components. The SPIOS forms a solid block, which is self-supporting. The SPIOS is shown in the right-hand side of FIG. 41, with the left-hand side showing an example of an optical system built from discrete components.

Figure 42:
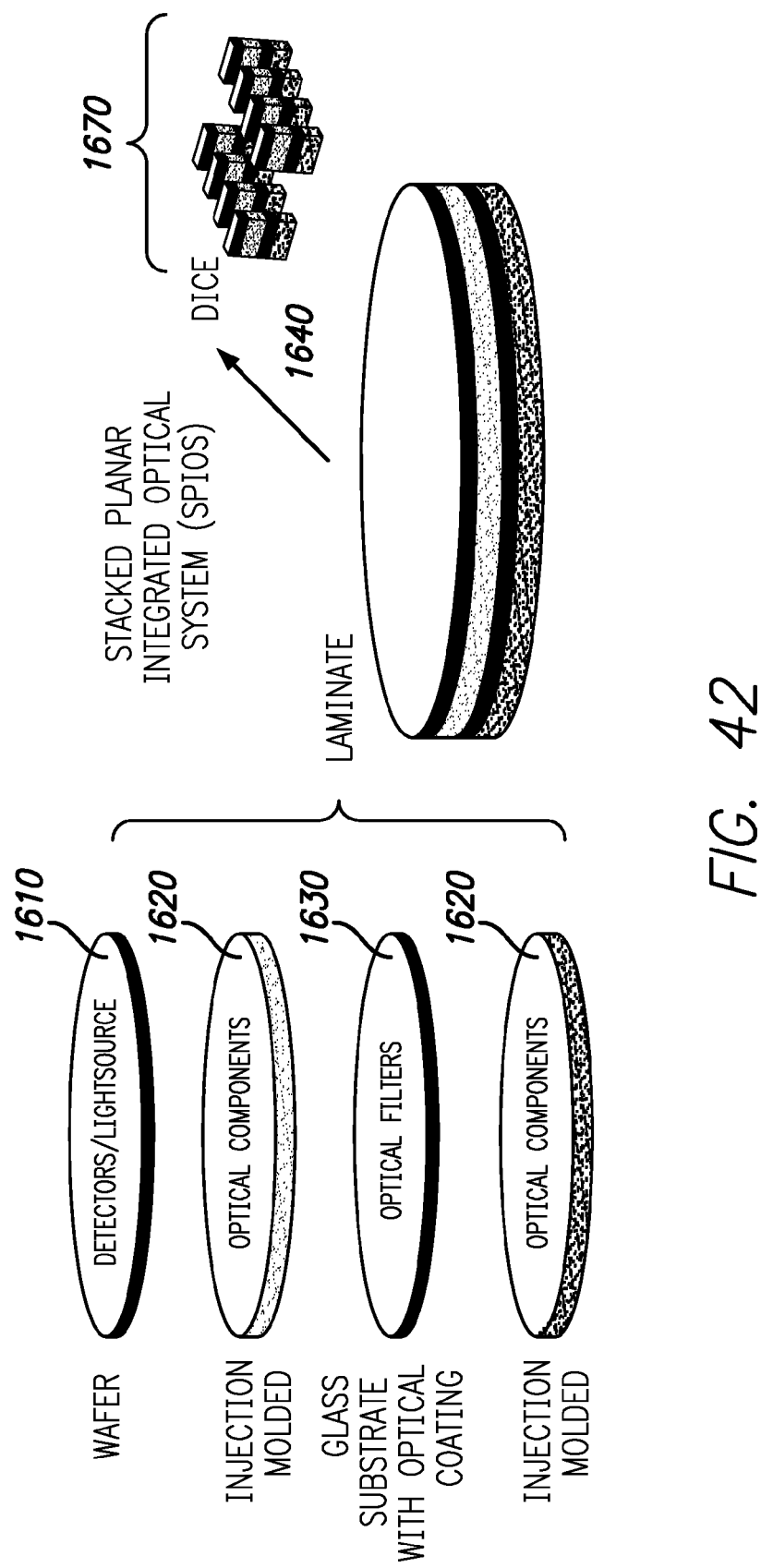
FIG. 42 shows illustrative layers of a wafer-scale stacked planar integrated optical system (SPIOS) in accordance with embodiments of the invention.

More specifically, in an embodiment of the invention shown in FIG. 42, the inventive optical interrogating system may be designed to be manufactured as a SPIOS (also referred to as a "Wafer Scale Optical System" or a "Wafer Level Optical System"). As shown in FIG. 42, the SPIOS includes various layers that are stacked and aligned. In the wafer layer 1610, one or more light sources (e.g., LEDs and photodiodes) and detectors may be laid out on a wafer. Alternatively, they may be naked chips (e.g., sold by Avago Technologies or Hamamatsu), which are individually aligned and laminated onto the SPIOS units.

One or more optical layers 1620 may include mirrors, absorbers, and/or other optical components laid out on a wafer-sized injection molded disk. Mold inserts defining optical surfaces are made by a diamond turning/milling company (e.g., Kaleido Technology in Denmark). Gold or protected silver is applied to mirror surfaces, e.g., by sputtering, while any absorbers are masked off during the process.

The optical filter layer 1630 includes a wafer-sized glass substrate with optional (e.g., dielectrical) coatings. Specifically, multilayer optical coatings may be applied on both sides of the glass substrate using ion-assisted sputtering to form durable coatings. The technique is similar to that used in manufacturing fluorescence filters by, e.g., Semrock in the United States and Delta in Denmark. Thus, in one example, dielectrical coatings applied on both sides of the substrate operate to filter excitation light, as well as the resulting fluorescence.

As shown in FIG. 42, in one embodiment, a wafer layer 1610 may be followed by an optical layer 1620, an optical filter layer 1630, and another optical layer 1620. The entire stack is then thoroughly aligned and laminated, e.g., by gluing, and the connections are bonded onto the chips. The stack is then diced 1640 using, e.g., a diamond saw to form multiple assembled SPIOS units 1670, which can then be mounted and connected to electronics.

Figure 43:
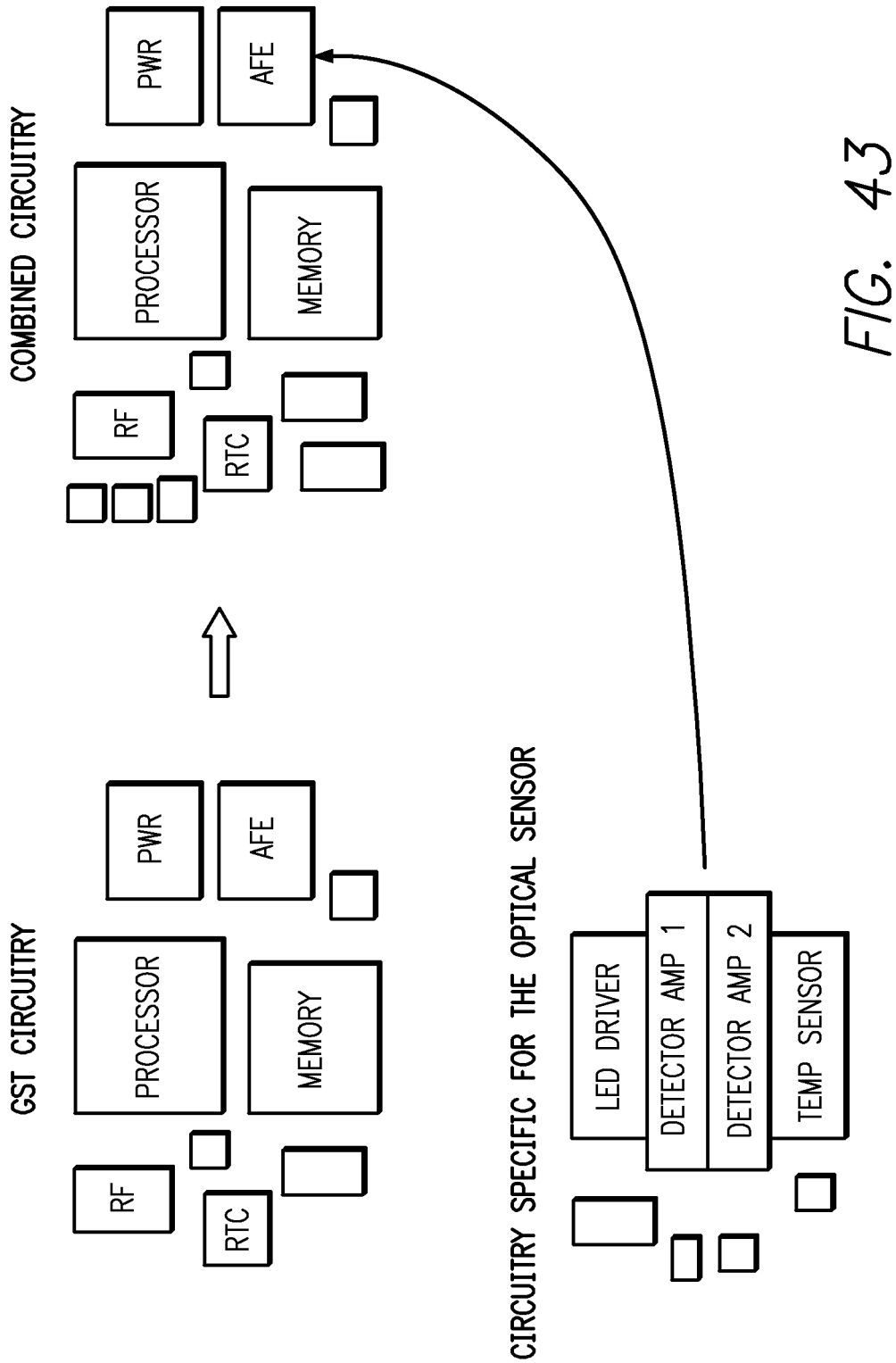
FIG. 43 illustrates the addition of key optical sensor electronic components to an analog front-end for electrochemical sensing in accordance with embodiments of the invention.

The above-described system may be made small and is suitable for large-scale production. The system may be used for interrogating a sensor in a light scattering environment, such as a sensor implanted into the skin, as well as a fiber sensor. Packaging may be used to block out ambient light. Moreover, as shown in FIG. 43, to save board space, a LED driver, two amplifier chains, and a temperature sensor specific to the optical sensor may be integrated into a custom chip and added to the analog front-end (AFE) for the electrochemical sensor, e.g., the AFE designed for use with the MiniLink® transmitter (MiniLink® available from Medtronic, Inc.).

In embodiments of the invention, the LED light source 1320 shown in FIG. 5 may be replaced with a red laser diode for illumination of the assay chemistry. The nature of a laser diode (smaller source diameter emission angle compared to an LED) provides for reduction of the size of the optical system relating to the excitation of the fiber sensor, as well as enhanced coupling efficiency from the laser diode to the fiber sensor. The latter, in turn, leads to a higher signal to noise ratio, which again leads to shorter measurement times and a smaller battery size. Battery capacity may be reduced by as much as 75%, which also significantly reduces the size of the transmitter 10.

Moreover, the higher excitation efficiency and narrower wavelength range of the laser diode reduce stray light problems, such that a lower light pickup may be accepted at the detector side. As a result, the part of the optical system relating to fluorescence detection is reduced. All in all, the use of a laser diode may reduce the size of the optical system to about 75% of the size of an optical system using LED excitation. Thus, e.g., a transmitter device 10 employing a laser diode as the illumination source of its optical interrogating system may have a volume of about 15 cm$^3$ and a weight of about 10 g.

Figure 44:
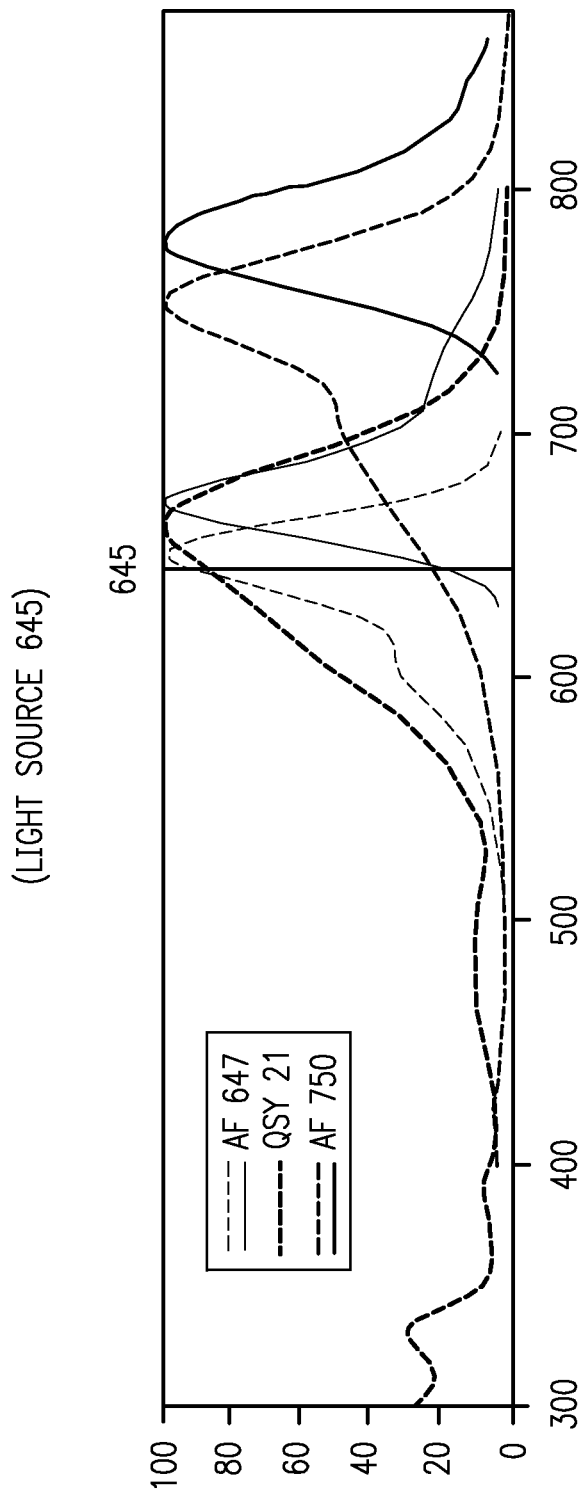
FIG. 44 shows wavelength ranges for three fluorophores which may be used with a laser diode source at 645 nm in accordance with embodiments of the invention.

To use a red laser diode, the (assay) chemistry must be red-shifted, meaning that new fluorophores operating at higher wavelengths must be used, in order to operate in a range where the laser diode is able to excite the chemistry. In this regard, it has been found that several fluorophores, including AF647, QSY 21, and AF750 may be used in conjunction with a laser diode source at 645 nm. See FIG. 44.

To further miniaturize the optical system and thus reduce the size of the transmitter 10, it is beneficial to incorporate the laser diode into the stacked planar integrated optical system (SPIOS) format discussed above. It has been found that such an implementation further decreases the transmitter size to about 11 cm$^3$.

Sterilization, Storage, and Shelf-Life Stability

A typical electrochemical sensor—e.g., the Enlite® sensor—may normally be stored at room temperature and ambient atmospheric relative humidity levels. To enable storage of the orthogonally redundant sensor (which may include such an electrochemical sensor) under these same conditions and, at the same time, maintain desired usability, embodiments of the invention include a dry version of the assay for the optical sensor. The term "dry chemistry" as used in this context refers to the dry form of the assay as compared to the original wet composition. The dry chemistry may, for example, be in the form of a freeze dried powder or suspended in a polymer, and not only enables dry packaging and dry storage, but also improves shelf life stability. The assay chemistry may, e.g., be dried via a lyophilization step, which includes freezing the assay and sublimation of liquid media through rapid vacuum drying.

Moreover, as noted previously, a typical electrochemical sensor is usually sterilized through a (e-beam) radiation sterilization process. Application of the same sterilization process to an optical sensor, or to an orthogonally redundant sensor that includes an optical sensor, however, presents practical challenges, as e-beam radiation may detrimentally affect the assay chemistry and, as such, result in loss of (optical) sensor response. In this regard, in embodiments of the invention, a protective formulation may be included in the assay to counteract the harmful effects of e-beam on, e.g., MBL and fluorescent dyes. The protective formulation includes protective chemical agents that, in addition to withstanding radiation sterilization effects, also facilitate sensor hydration and startup.

With regard to the above-described dry chemistry and protective formulation, it has also been discovered that, even without the protective formulation, optical sensors using the dry chemistry described above show little change in sensor response when exposed to e-beam radiation. In addition, the dry chemistry in fiber sensors has been shown to retain its stability in the dry state for three months at 5° C.

Connectivity and Data Warehousing

Connectivity and data warehousing are integrated with the orthogonally redundant sensor system through communication with networking products available, e.g., from Medtronic, Inc., including a handheld monitor (such as, e.g., MySentry™ Glucose Monitor) and CareLink® therapy management software.

In one embodiment, the Medtronic system provides data transfer capability between the Medtronic Patient Network (MPN) and internet-based Medtronic CareLink® therapy management software system. This system is designed to efficiently provide data downloading, warehousing, and reports for patients and their healthcare providers (HCPs). Patients and HCPs use CareLink® reports in many ways, including reviewing data, understanding behavior, and optimizing therapy. Additional reports provide decision support in a "professional" version of the CareLink® system (available to HCPs) that streamlines data analysis in the clinical setting and highlights opportunities for therapy modifications that can drive improved outcomes.

Figure 45:
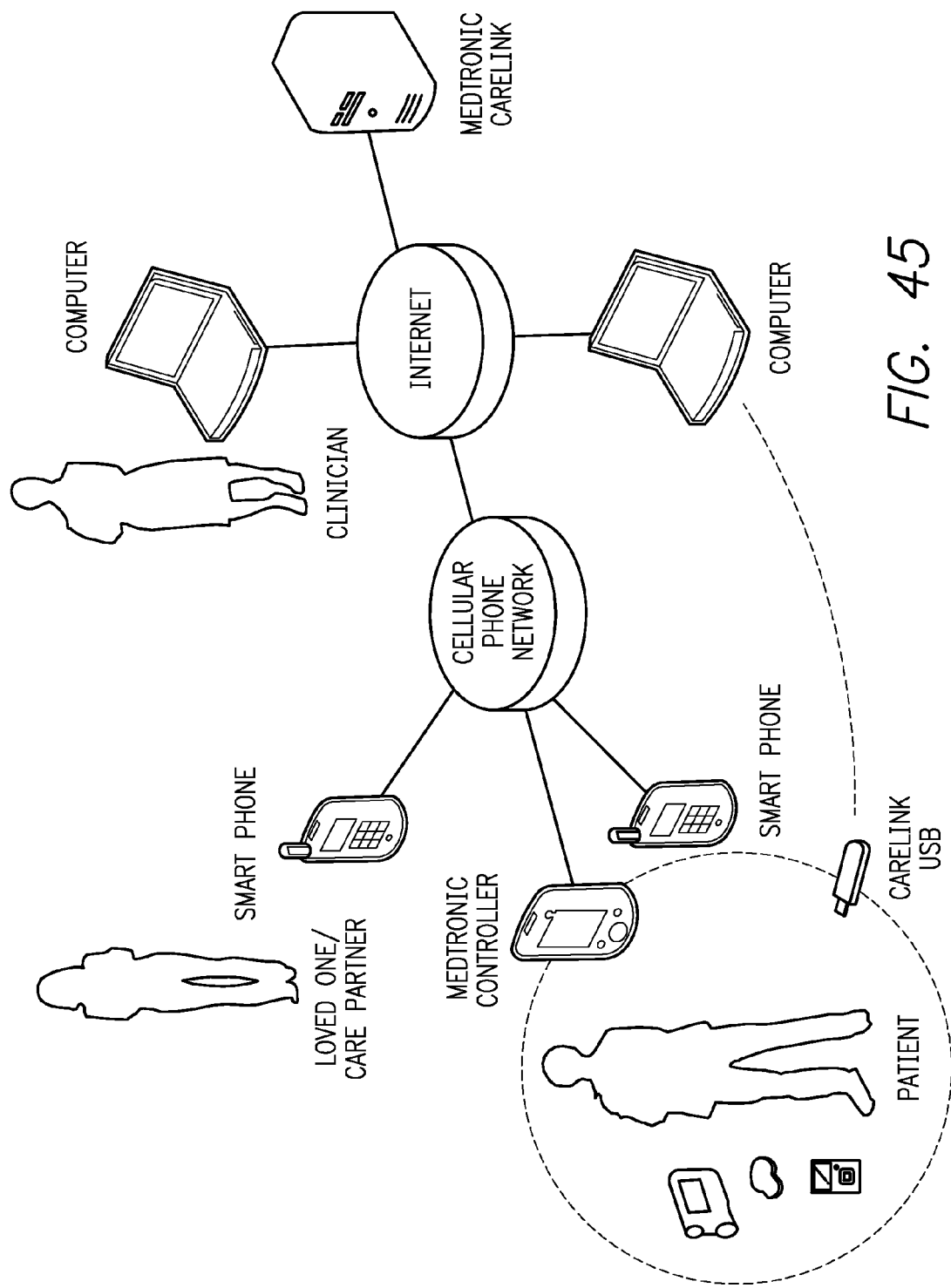
FIG. 45 shows a care network using various components and methodologies in accordance with embodiments of the invention.

In a further embodiment, a Connected Care system includes an On Body Communicator (OBC) utilizing currently available mobile networks technology. The system provides the Patient, a Loved One, and a Physician access to information from the Patient's MPN in near real-time. See FIG. 45.

The primary function of the OBC is to provide mobile ambulatory MPN connectivity and data processing. The OBC communicates with the Medtronic proprietary RF protocol to establish communications with the MPN and deliver them to "the cloud" through a cellular network capability. Data can then be retrieved from the cloud and sent to the CareLink® Personal internet-based system. When a cellular signal is unavailable, the OBC continues to maintain operations required to collect and process data from the MPN until the cellular signal is re-established.

Once data in the cloud is available in a near real-time, the CareLink® system can deliver features designed for commercially available web enabled electronics devices such as smart phones and tablets.

As noted previously in connection with FIGS. 1 and 11, in a preferred embodiment, the OBC may be in the form of a handheld controller or monitor with integrated blood glucose meter used for calibration. The handheld monitor is designed to work in conjunction with the orthogonally redundant sensor system. In addition to sending data to the cloud, the handheld monitor improves accuracy through the use of algorithms to provide an error check, ensuring that inaccurate blood glucose readings are not communicated.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, and all changes which come within the meaning and range of equivalency of the claims are therefore intended to be embraced therein.

What is claimed is:

1. A continuous glucose monitoring system comprising:
    an orthogonally redundant glucose sensor device for determining the concentration of glucose in a body of a user, said sensor device comprising an optical glucose sensor and an electrochemical glucose sensor; and
    an external transmitter operatively coupled to said electrochemical and optical glucose sensors and having a housing, wherein the transmitter includes sensor electronics in said housing, said sensor electronics including at least one physical microprocessor that is configured to:
        receive a first signal from the electrochemical glucose sensor and a second signal from the optical glucose sensor;
        perform a respective integrity check on each of said first and second signals;
        determine whether the first signal can be calibrated, and whether the second signal can be calibrated, wherein said determination is made based on whether the first signal and the second signal pass or fail their respective integrity checks;
        if it is determined that the first signal can be calibrated, calibrate said first signal to generate an electrochemical sensor glucose (SG) value;
        if it is determined that the second signal can be calibrated, calibrate said second signal to generate an optical sensor glucose (SG) value; and
        fuse said electrochemical SG value and said optical SG value to calculate a single, fused sensor glucose value for the orthogonally redundant glucose sensor device,
    wherein said optical glucose sensor includes a lightguide on a first respective substrate, said electrochemical glucose sensor includes at least one electrode on a second respective substrate, and said first and second respective substrates are integrated into an integrated flex circuit; and
    wherein said lightguide is disposed in an interior of said integrated flex circuit and said at least one electrode is disposed on an external surface of said integrated flex circuit.

2. The system of claim 1, wherein said first signal is an electrical current (Isig).

3. The system of claim 1, wherein each said integrity check includes checking for sensitivity loss.

4. The system of claim 1, wherein each said integrity check includes checking for noise.

5. The system of claim 1, wherein each said integrity check includes checking for sensor drift.

6. The system of claim 1, wherein the integrity check for the electrochemical sensor includes checking for sensitivity loss, noise, and sensor drift, and wherein the microprocessor determines that the first signal passes its integrity check, and can be calibrated, if the sensitivity loss, noise, and drift fall within respective calculated limits.

7. The system of claim 6, wherein, if one or more of the sensitivity loss, noise, and drift fall outside of respective calculated limits, the microprocessor determines that the first signal fails its integrity check and cannot be calibrated.

8. The system of claim 7, wherein, if the microprocessor determines that the first signal has failed its integrity check, the microprocessor further determines whether the second signal passes its integrity check and, if the second signal passes its integrity check, uses the second signal to correct said first signal.

9. The system of claim 8, wherein the microprocessor uses the second signal to correct the first signal via in-line sensor mapping to generate a corrected first signal.

10. The system of claim 9, wherein the microprocessor calibrates the corrected first signal to generate said electrochemical SG value.

11. The system of claim 9, wherein the microprocessor performs said in-line sensor mapping by using the relation $first\_signal\_buffer_n = a \times second\_signal\_buffer_n + b$, where a and b are mapping parameters.

12. The system of claim 1, wherein the integrity check for the optical sensor includes checking for sensitivity loss, noise, and sensor drift, and wherein the microprocessor determines that the second signal passes its integrity check, and can be calibrated, if the sensitivity loss, noise, and drift fall within respective calculated limits.

13. The system of claim 12, wherein, if one or more of the sensitivity loss, noise, and drift fall outside of respective calculated limits, the microprocessor determines that the second signal fails its integrity check and cannot be calibrated.

14. The system of claim 13, wherein, if the microprocessor determines that the second signal has failed its integrity check, the microprocessor further determines whether the first signal passes its integrity check and, if the first signal passes its integrity check, uses the first signal to correct said second signal.

15. The system of claim 14, wherein the microprocessor uses the first signal to correct the second signal via in-line sensor mapping to generate a corrected second signal.

16. The system of claim 15, wherein the microprocessor calibrates the corrected second signal to generate said optical SG value.

17. The system of claim 15, wherein the microprocessor performs said in-line sensor mapping by using the relation $first\_signal\_buffer_n = a \times second\_signal\_buffer_n + b$, where a and b are mapping parameters.

18. The system of claim 1, wherein the transmitter wirelessly transmits said single, fused sensor glucose value.

19. The system of claim 1, wherein the transmitter is worn on the user's body.

20. The system of claim 1, further including a handheld monitor.

21. The system of claim 20, wherein the handheld monitor includes an integrated blood glucose meter.

22. The system of claim 21, wherein the transmitter wirelessly transmits said single, fused sensor glucose value to the hand-held monitor.

23. The system of claim 1, further including an insulin pump.

24. The system of claim 23, wherein the transmitter wirelessly transmits said single, fused sensor glucose value to the insulin pump.

25. The system of claim 24, wherein said glucose monitoring system is a closed-loop system.

26. The system of claim 1, wherein the optical glucose sensor includes an assay having a glucose receptor, a glucose analog, a first fluorophore, and a reference fluorophore different from said first fluorophore.

27. The system of claim 26, wherein said output signal of the optical glucose sensor is a ratio of the fluorescence signal from the first fluorophore to the fluorescence signal from the reference fluorophore.

28. The system of claim 1, wherein each of the electrochemical and optical sensors has a distal portion and a proximal portion, and wherein respective distal portions of the optical sensor and the electrochemical sensor are co-located within the user's body.

29. The system of claim 1, further including an insertion needle, wherein said integrated flex circuit is configured to be carried inside said needle for simultaneous insertion of said optical glucose sensor and said electrochemical glucose sensor into the user's body.

30. The system of claim 1, wherein each of said optical and electrochemical glucose sensors has a respective proximal portion that is disposed externally to the user's body and a respective distal portion configured for internal placement in the user's body.

31. The system of claim 30, wherein said lightguide is an optical fiber having said proximal portion that is disposed externally to the user's body and said distal portion configured for internal placement in the user's body.

32. The system of claim 31, wherein the optical fiber has a circular cross-section having a diameter of less than 200 μm.

33. The system of claim 30, wherein said housing of the external transmitter houses said respective proximal portions of the optical and electrochemical glucose sensors.

34. A program code storage device, comprising:
a non-transitory computer-readable medium; and
non-transitory computer-readable program code, stored on the computer-readable medium, the computer-readable program code having instructions, which when executed cause a microprocessor to:
receive a first signal from an electrochemical glucose sensor and a second signal from an optical glucose sensor of an orthogonally redundant glucose sensor device for determining the concentration of glucose in a body of a user, wherein said optical glucose sensor includes a lightguide on a first respective substrate, said electrochemical glucose sensor includes at least one electrode on a second respective substrate, and said first and second respective substrates are integrated into an integrated flex circuit, and wherein said lightguide is disposed in an interior of said integrated flex circuit and said at least one electrode is disposed on an external surface of said integrated flex circuit;
perform a respective integrity check on each of said first and second signals;

determine whether the first signal can be calibrated, and whether the second signal can be calibrated, wherein said determination is made based on whether the first signal and the second signal pass or fail their respective integrity checks;

if it is determined that the first signal can be calibrated, calibrate said first signal to generate an electrochemical sensor glucose (SG) value;

if it is determined that the second signal can be calibrated, calibrate said second signal to generate an optical sensor glucose (SG) value; and fuse said electrochemical SG value and said optical SG value to calculate a single, fused sensor glucose value for the orthogonally redundant glucose sensor device.

35. The program code storage device of claim 34, wherein said first signal is an electrical current (Isig).

36. The program code storage device of claim 34, wherein the optical glucose sensor includes an assay fluorophore and a reference fluorophore, wherein the assay fluorophore generates an assay fluorescence signal and the reference fluorophore generates a reference fluorescence signal, and wherein said second signal from the optical glucose sensor is a ratio of the assay fluorescence signal to the reference fluorescence signal.

37. The program code storage device of claim 34, wherein each said integrity check includes checking for sensitivity loss.

38. The program code storage device of claim 34, wherein each said integrity check includes checking for noise.

39. The program code storage device of claim 34, wherein each said integrity check includes checking for sensor drift.

40. The program code storage device of claim 34, wherein the integrity check for the electrochemical sensor includes checking for sensitivity loss, noise, and sensor drift, and wherein the computer-readable program code includes instructions, which when executed cause the microprocessor to determine that the first signal passes its integrity check, and can be calibrated, if the sensitivity loss, noise, and drift fall within respective calculated limits.

41. The program code storage device of claim 40, wherein, if one or more of the sensitivity loss, noise, and drift fall outside of respective calculated limits, it is determined that the first signal fails its integrity check and cannot be calibrated.

42. The program code storage device of claim 41, wherein, if it is determined that the first signal has failed its integrity check, the instructions, when executed, further cause the microprocessor to determine whether the second signal passes its integrity check and, if the second signal passes its integrity check, to use the second signal to correct said first signal.

43. The program code storage device of claim 42, the computer-readable program code including instructions, which when executed cause the microprocessor to use the second signal to correct the first signal via in-line sensor mapping to generate a corrected first signal.

44. The program code storage device of claim 43, the computer-readable program code including instructions, which when executed cause the microprocessor to calibrate the corrected first signal to generate said electrochemical SG value.

45. The program code storage device of claim 43, the computer-readable program code including instructions, which when executed cause the microprocessor to perform said in-line sensor mapping by using the relation $first\_signal\_buffer_n = a \times second\_signal\_buffer_n + b$, where a and b are mapping parameters.

46. The program code storage device of claim 34, wherein the integrity check for the optical sensor includes checking for sensitivity loss, noise, and sensor drift, and wherein the computer-readable program code includes instructions, which when executed cause the microprocessor to determine that the second signal passes its integrity check, and can be calibrated, if the sensitivity loss, noise, and drift fall within respective calculated limits.

47. The program code storage device of claim 46, wherein, if one or more of the sensitivity loss, noise, and drift fall outside of respective calculated limits, it is determined that the second signal fails its integrity check and cannot be calibrated.

48. The program code storage device of claim 47, wherein, if it is determined that the second signal has failed its integrity check, the instructions, when executed, further cause the microprocessor to determine whether the first signal passes its integrity check and, if the first signal passes its integrity check, to use the first signal to correct said second signal.

49. The program code storage device of claim 48, the computer-readable program code including instructions, which when executed cause the microprocessor to use the first signal to correct the second signal via in-line sensor mapping to generate a corrected second signal.

50. The program code storage device of claim 49, the computer-readable program code including instructions, which when executed cause the microprocessor to calibrate the corrected second signal to generate said optical SG value.

51. The program code storage device of claim 49, the computer-readable program code including instructions, which when executed cause the microprocessor to perform said in-line sensor mapping using the relation $first\_signal\_buffer_n = a \times second\_signal\_buffer_n + b$, where a and b are mapping parameters.

52. The program code storage device of claim 34, wherein said integrated flex circuit is configured to be carried inside an insertion needle for simultaneous insertion of said optical glucose sensor and said electrochemical glucose sensor into the user's body.

53. The program code storage device of claim 34, wherein each of said optical and electrochemical glucose sensors has a respective proximal portion that is disposed externally to the user's body and a respective distal portion configured for internal placement in the user's body.

54. The program code storage device of claim 53, wherein said lightguide is an optical fiber having said proximal portion that is disposed externally to the user's body and said distal portion configured for internal placement in the user's body.

55. The program code storage device of claim 54, wherein the optical fiber has a circular cross-section having a diameter of less than 200 μm.

* * * * *